(12) United States Patent
Hyun et al.

(10) Patent No.: US 12,370,818 B2
(45) Date of Patent: Jul. 29, 2025

(54) PORTABLE PRINTER

(71) Applicant: LG HOUSEHOLD & HEALTH CARE LTD., Seoul (KR)

(72) Inventors: Chang Hwan Hyun, Seoul (KR); Ji Hee Lee, Seoul (KR); Kang Ug Lee, Pyeongtaek-si (KR); Sung Hyoun Jang, Seoul (KR); Hyeon Jin Kweon, Seoul (KR); Hae Na Cheong, Seoul (KR); Ji Hee Jeong, Seoul (KR); Jung Yong Lee, Seoul (KR); Ha Young Kim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 18/270,419

(22) PCT Filed: Oct. 20, 2022

(86) PCT No.: PCT/KR2022/016085
§ 371 (c)(1),
(2) Date: Jun. 29, 2023

(87) PCT Pub. No.: WO2023/075294
PCT Pub. Date: May 4, 2023

(65) Prior Publication Data
US 2024/0109350 A1 Apr. 4, 2024

(30) Foreign Application Priority Data

Oct. 26, 2021 (KR) .......................... 10-2021-0143969
Feb. 9, 2022 (KR) .......................... 10-2022-0017075
(Continued)

(51) Int. Cl.
*B41J 25/308* (2006.01)
*A61M 35/00* (2006.01)
(Continued)

(52) U.S. Cl.
CPC .......... *B41J 25/3086* (2013.01); *A61M 35/00* (2013.01); *A61M 37/00* (2013.01);
(Continued)

(58) Field of Classification Search
CPC .......... B41J 25/3086; B41J 3/36; B41J 3/407; B41M 3/00; B41M 5/00; A61M 35/00; A61M 37/00
See application file for complete search history.

(56) References Cited

U.S. PATENT DOCUMENTS

| 5,988,900 A | 11/1999 | Bobry |
|---|---|---|
| 6,070,962 A | 6/2000 | Kinoshita |

(Continued)

FOREIGN PATENT DOCUMENTS

| CN | 216059017 U | 3/2022 |
|---|---|---|
| CN | 114794204 A | 7/2022 |

(Continued)

*Primary Examiner* — Henok D Legesse
(74) *Attorney, Agent, or Firm* — Birch, Stewart, Kolasch & Birch, LLP

(57) ABSTRACT

The present disclosure relates to a portable printer including a main body in a portable form which is capable of accommodating a cartridge having a nozzle for delivering a printing material to a target having a soft or hard surface, a seating part which is provided to be exposed to an outside from a lower portion of the main body to face the surface of the target and at least partially surrounds the nozzle, a roller provided respectively at the front and rear of the nozzle at the lower portion of the main body with respect to a direction in which the main body moves along the surface of the target to deliver the printing material to the target, and a printing adjustment unit configured to adjust a height difference between the nozzle and the roller to adjust a height difference between the nozzle and the surface of the target.

16 Claims, 67 Drawing Sheets

(30) Foreign Application Priority Data

Sep. 15, 2022 (KR) .................. 10-2022-0116407
Oct. 12, 2022 (KR) .................. 10-2022-0130679

(51) Int. Cl.

| | |
|---|---|
| *A61M 37/00* | (2006.01) |
| *B41J 3/36* | (2006.01) |
| *B41J 3/407* | (2006.01) |
| *B41M 3/00* | (2006.01) |
| *B41M 5/00* | (2006.01) |

(52) U.S. Cl.

CPC .............. *B41J 3/36* (2013.01); *B41J 3/407* (2013.01); *B41M 3/00* (2013.01); *B41M 5/00* (2013.01)

(56) References Cited

U.S. PATENT DOCUMENTS

| | | | |
|---|---|---|---|
| 6,543,893 B2 | 4/2003 | Desormeaux | |
| 9,555,645 B1 | 1/2017 | Mealy et al. | |
| 2002/0070988 A1* | 6/2002 | Desormeaux | B41J 3/36 |
| | | | 347/8 |
| 2004/0001129 A1 | 1/2004 | Lim | |
| 2004/0240923 A1 | 12/2004 | Warrin et al. | |
| 2004/0246327 A1 | 12/2004 | Elzi | |
| 2006/0001696 A1 | 1/2006 | Ha et al. | |
| 2006/0192798 A1 | 8/2006 | Kuki et al. | |
| 2008/0316290 A1* | 12/2008 | Brown | B41J 3/36 |
| | | | 347/109 |
| 2009/0035043 A1* | 2/2009 | Perez | B41J 3/36 |
| | | | 400/619 |
| 2018/0050544 A1 | 2/2018 | Suzuki et al. | |
| 2020/0101763 A1 | 4/2020 | Ishida et al. | |
| 2020/0171831 A1* | 6/2020 | Lee | B41J 3/407 |
| 2023/0036021 A1 | 2/2023 | Ohashi et al. | |

FOREIGN PATENT DOCUMENTS

| | | |
|---|---|---|
| JP | 2006-272612 A | 10/2006 |
| JP | 2006-297691 A | 11/2006 |
| JP | 2010-520822 A | 6/2010 |
| JP | 4626069 B2 | 2/2011 |
| JP | 5154839 B2 | 2/2013 |
| JP | 2020-116807 A | 8/2020 |
| JP | 2021-84312 A | 6/2021 |
| JP | 2021-151773 A | 9/2021 |
| JP | 6996195 B2 | 1/2022 |
| JP | 2023-20119 A | 2/2023 |
| KR | 10-2004-0002099 A | 1/2004 |
| KR | 10-2006-0002097 A | 1/2006 |
| KR | 10-2016-0064616 A | 6/2016 |
| KR | 10-1655978 B1 | 9/2016 |
| KR | 10-2017-0105391 A | 9/2017 |
| KR | 10-1774412 B1 | 9/2017 |
| KR | 10-1783314 B1 | 10/2017 |
| KR | 10-1789668 B1 | 10/2017 |
| KR | 10-1802662 B1 | 11/2017 |
| KR | 10-1822882 B1 | 1/2018 |
| KR | 10-1822883 B1 | 1/2018 |
| KR | 10-1827267 B1 | 2/2018 |
| KR | 10-1827268 B1 | 2/2018 |
| KR | 10-1865605 B1 | 6/2018 |
| KR | 10-1865665 B1 | 6/2018 |
| KR | 10-1874256 B1 | 7/2018 |
| KR | 10-1892202 B1 | 8/2018 |
| KR | 10-1897512 B1 | 9/2018 |
| KR | 10-1898804 B1 | 9/2018 |
| KR | 10-1917907 B1 | 11/2018 |
| KR | 10-2009520 B1 | 8/2019 |
| WO | WO 2021/169712 A1 | 9/2021 |

* cited by examiner

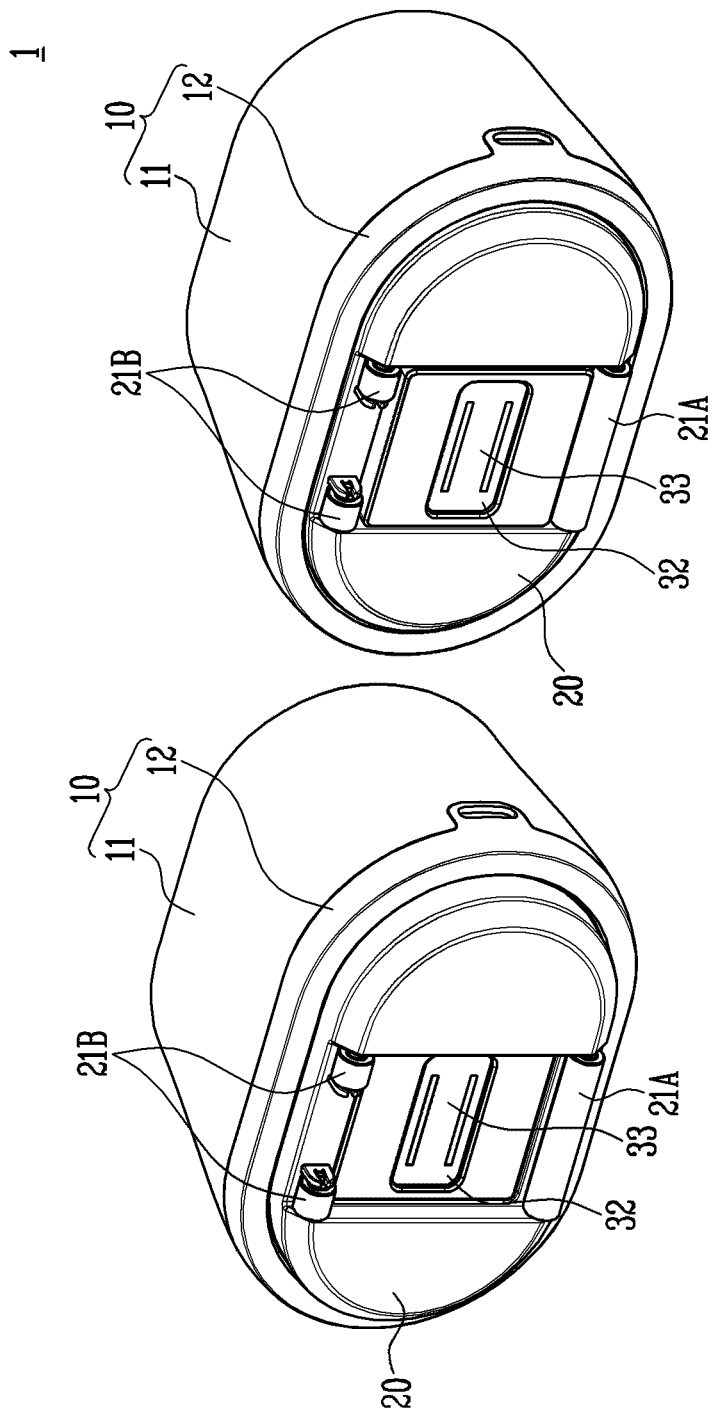

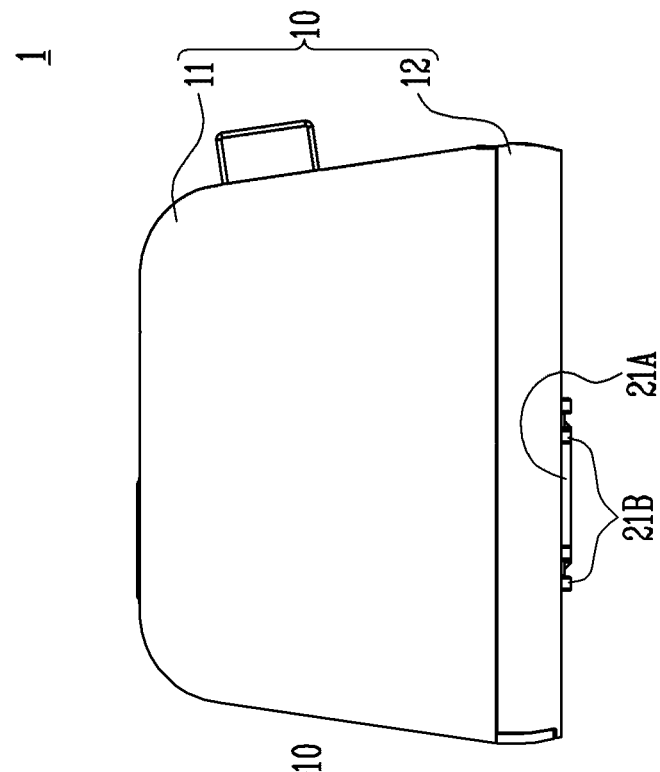
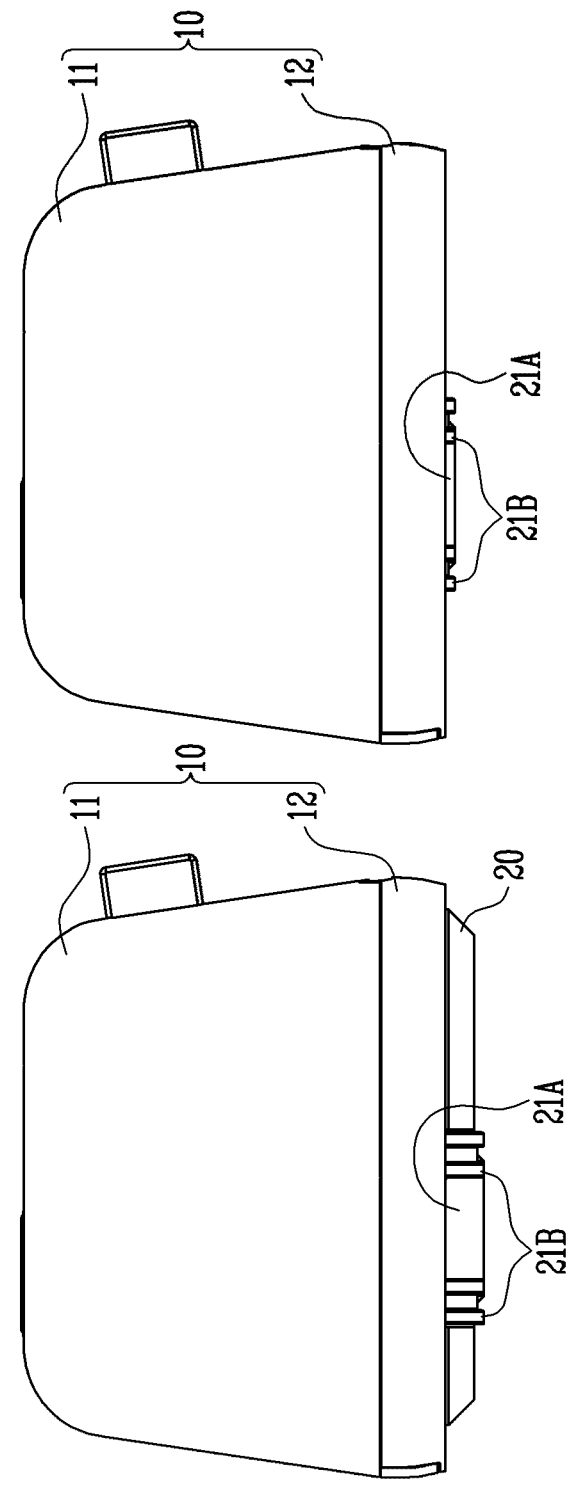

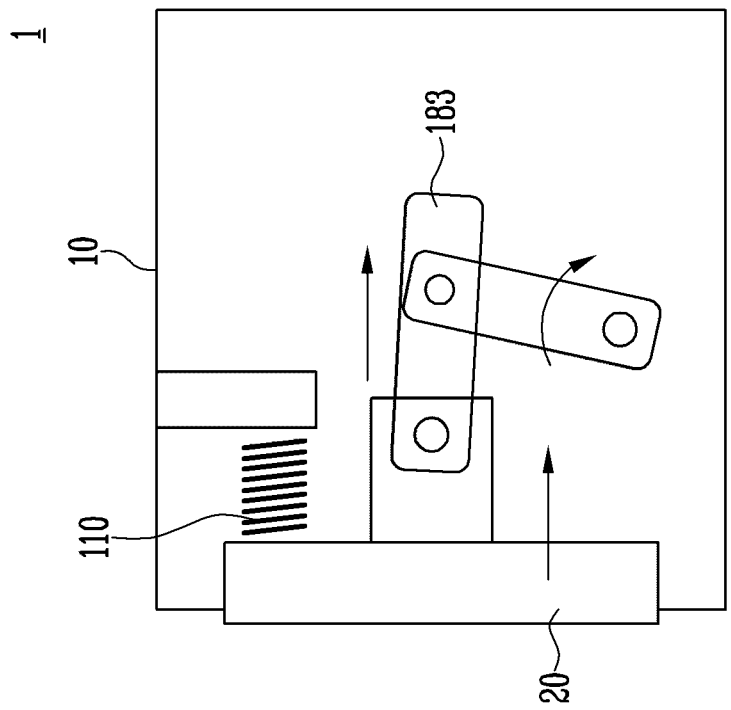
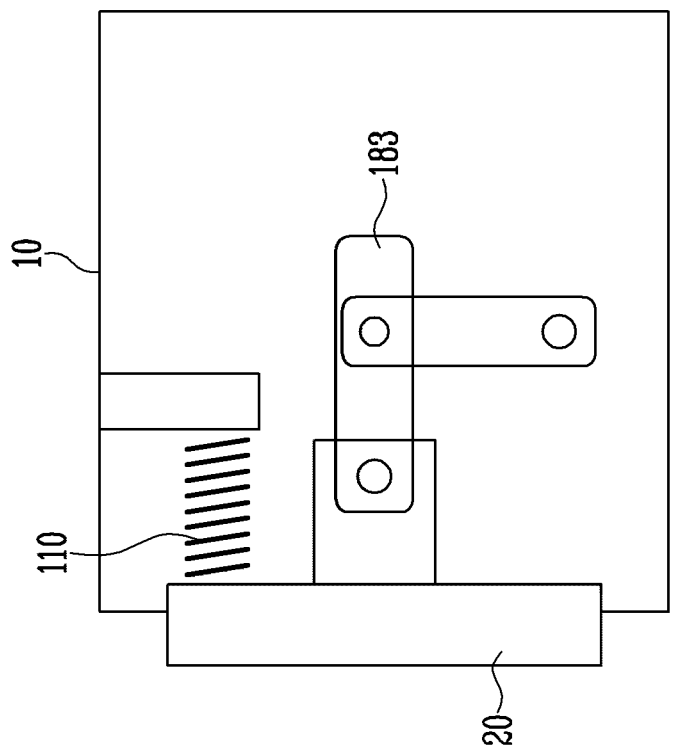

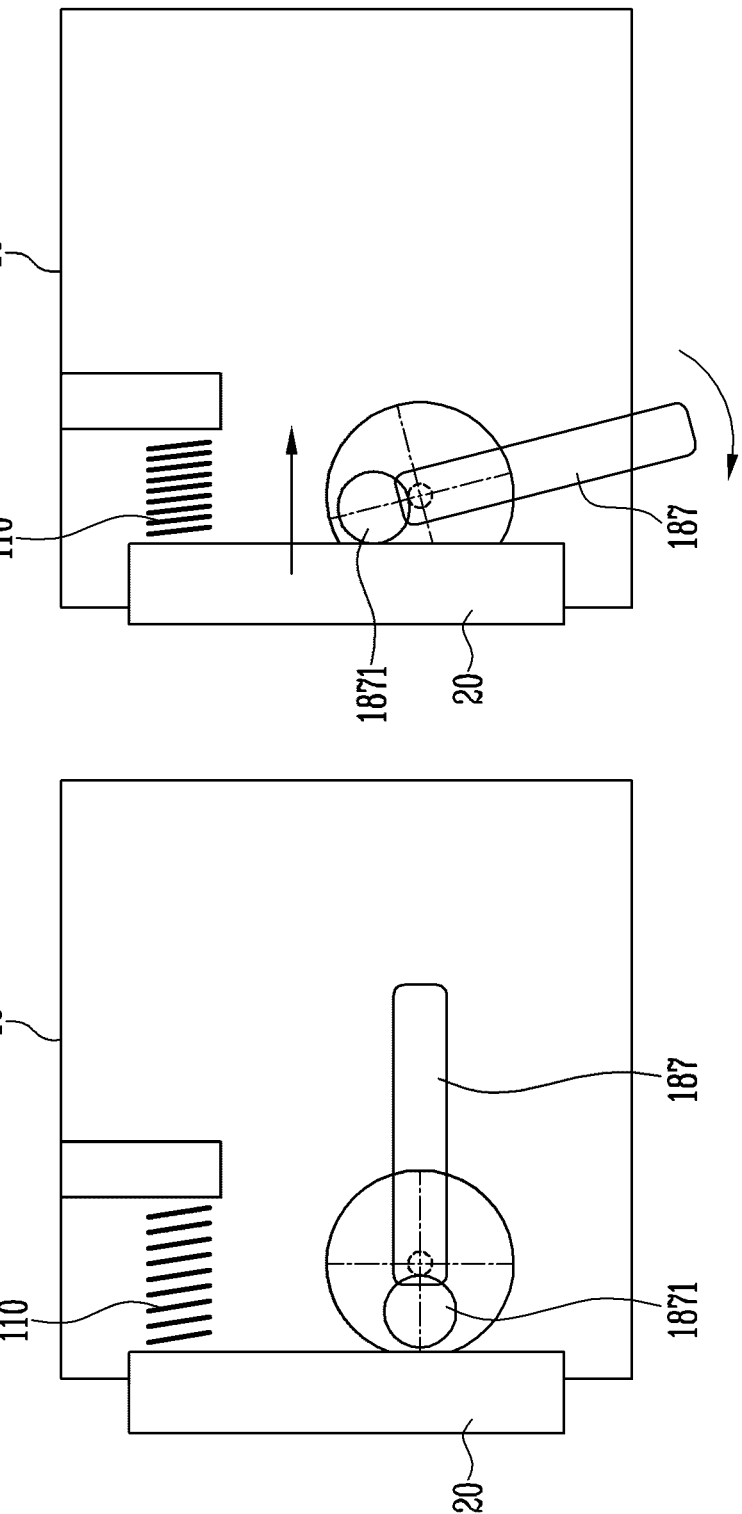

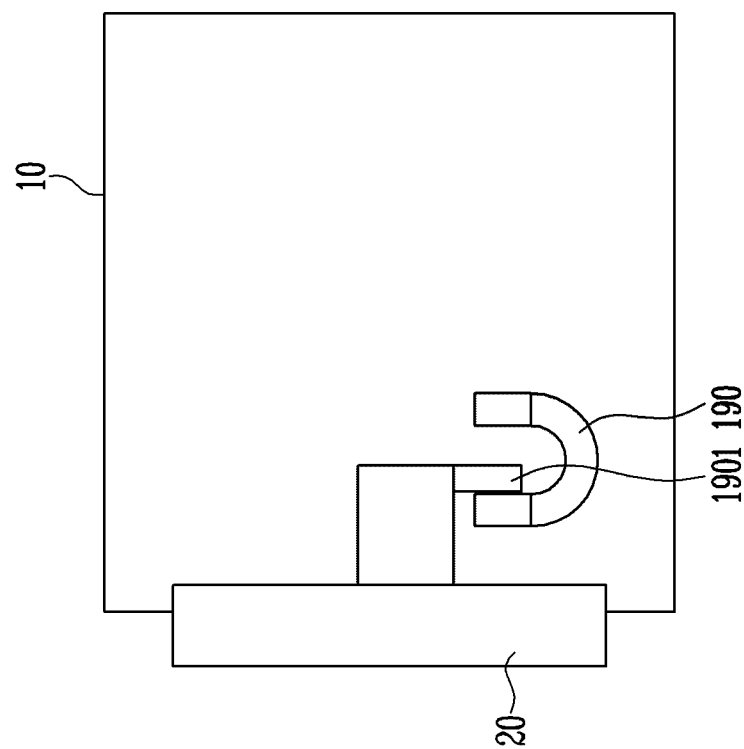
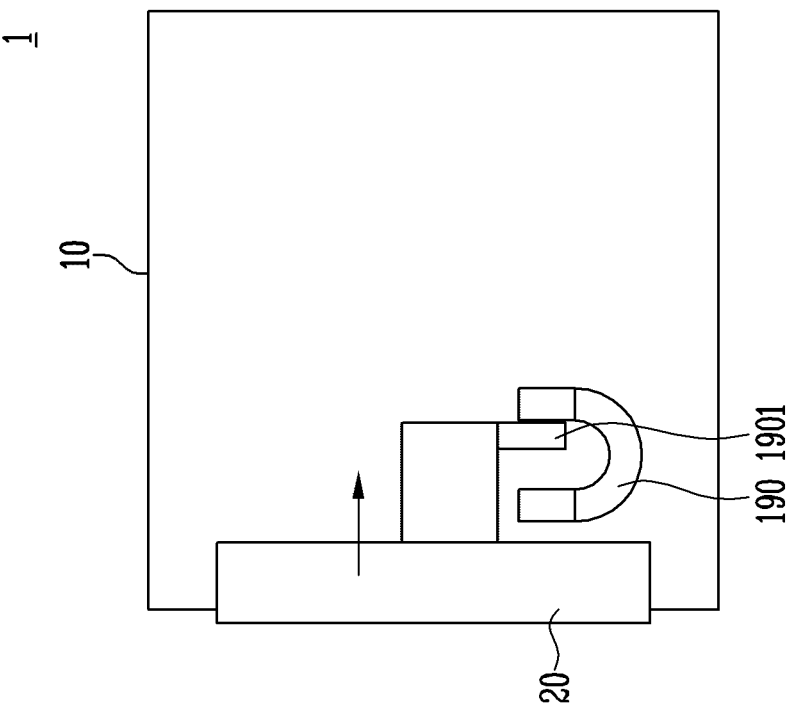
FIG. 47A
FIG. 47B

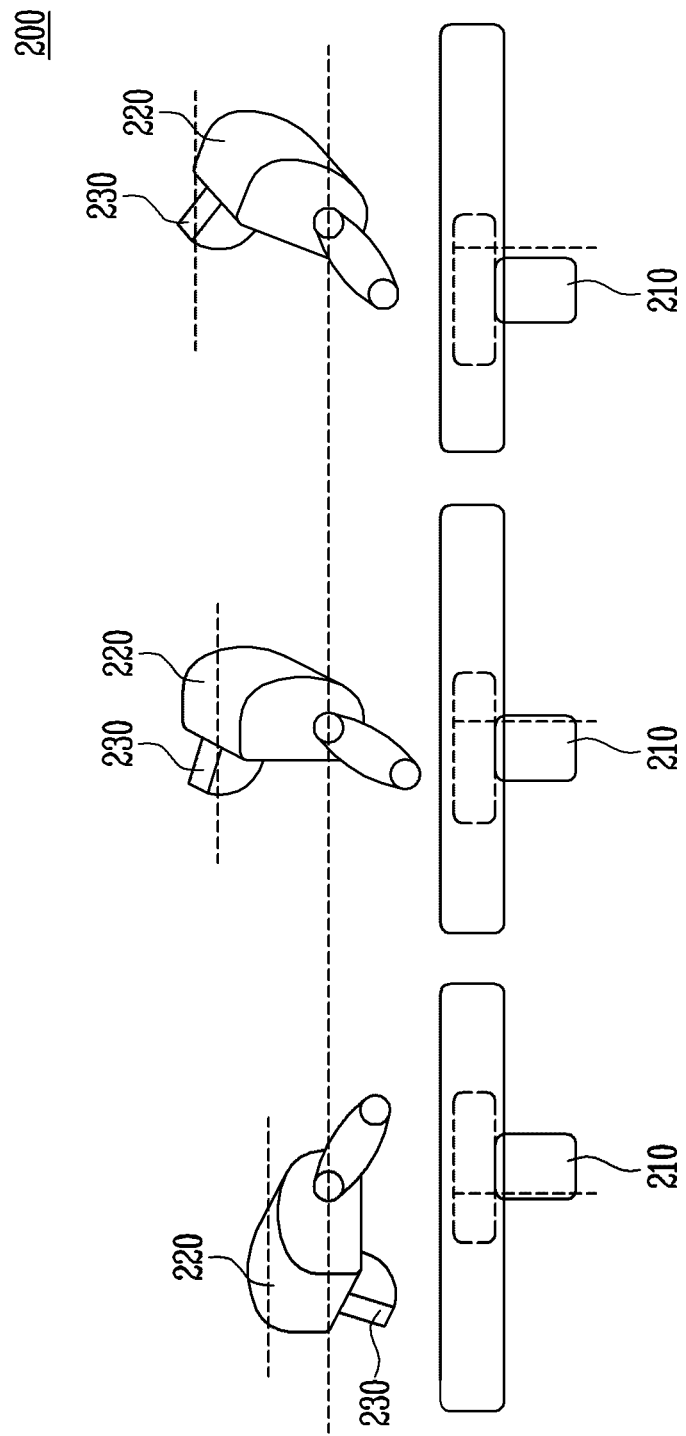

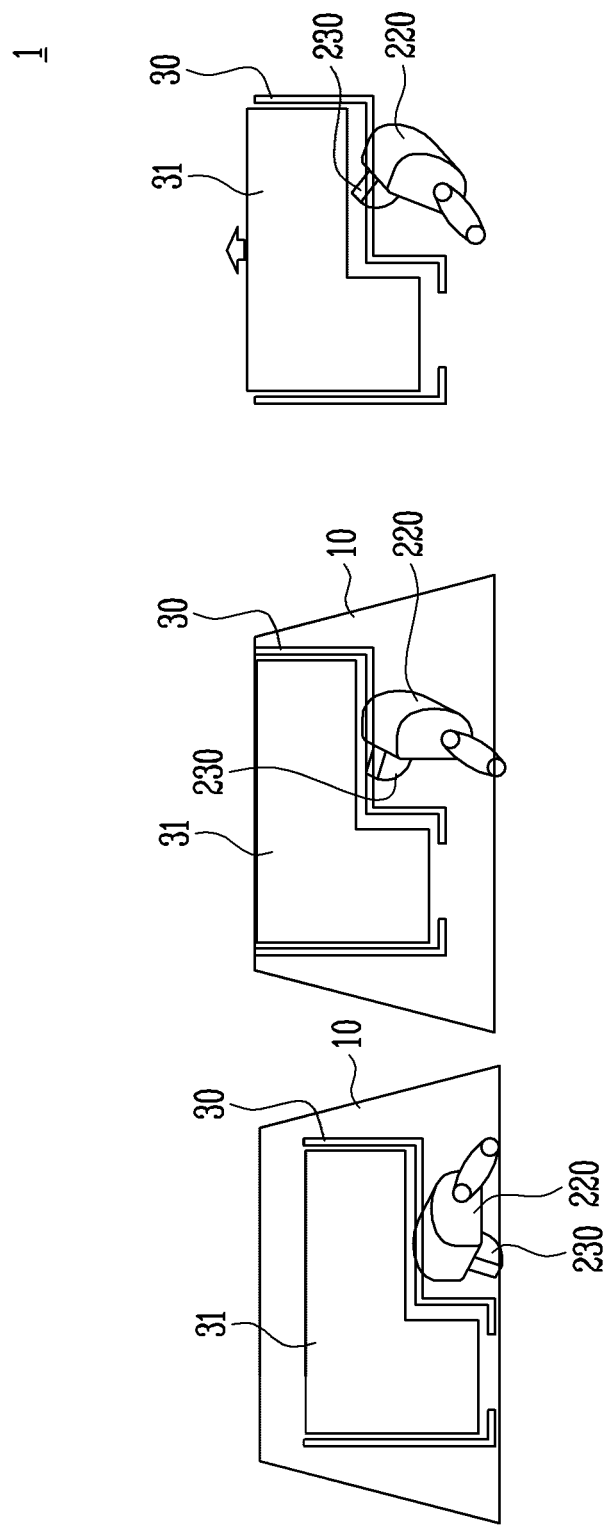

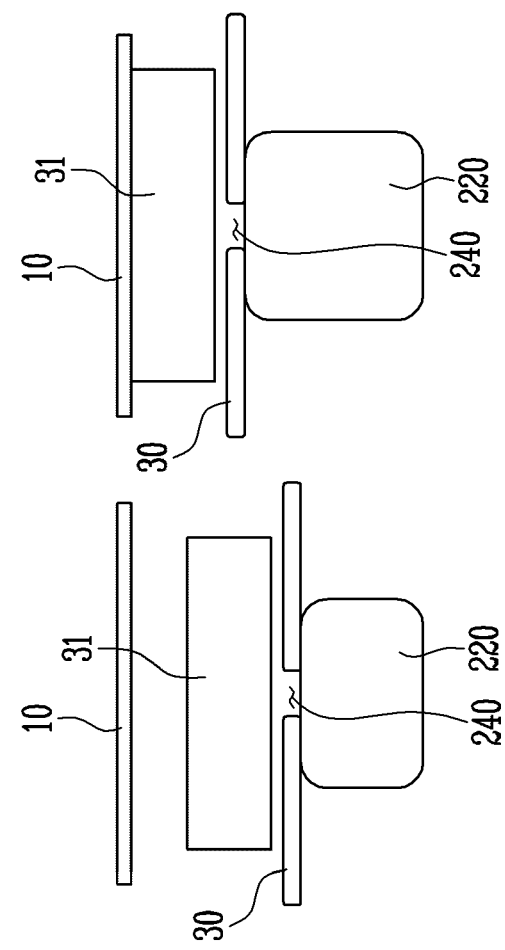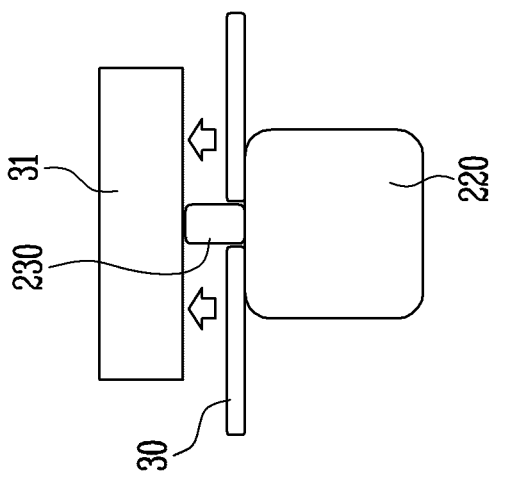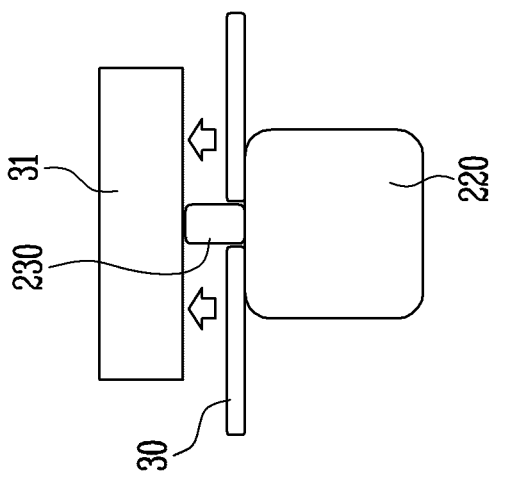

FIG. 68A
FIG. 68B
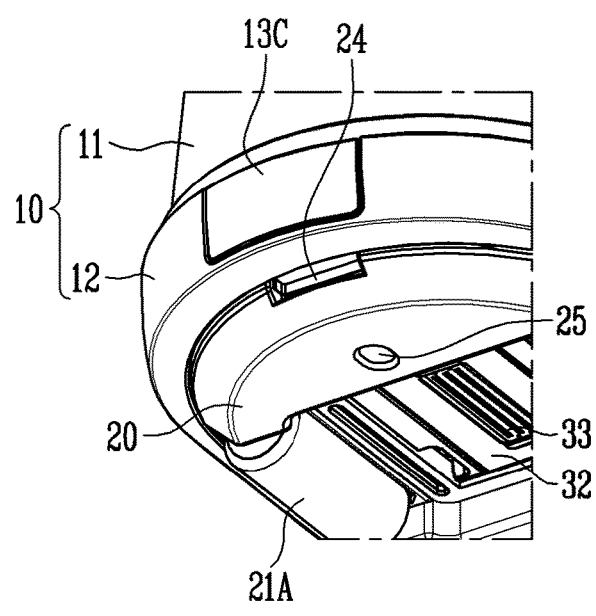
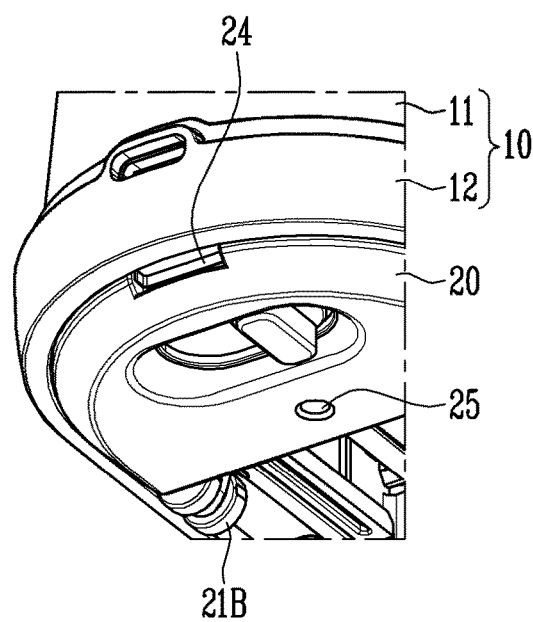

PORTABLE PRINTER

CROSS REFERENCE TO RELATED APPLICATIONS

This application is the National Phase of PCT International Application No. PCT/KR2022/016085, filed on Oct. 20, 2022, which claims priority under 35 U.S.C. 119(a) to Patent Application Nos. 10-2021-0143969, filed in the Republic of Korea on Oct. 26, 2021; 10-2022-0017075, filed in the Republic of Korea on Feb. 9, 2022; 10-2022-0116407, filed in the Republic of Korea on Sep. 15, 2022; and 10-2022-0130679, filed in the Republic of Korea on Oct. 12, 2022, all of which are hereby expressly incorporated by reference into the present application.

TECHNICAL FIELD

The present disclosure relates to a portable printer.

BACKGROUND ART

In general, skin of a person's body forms the person's appearance, and the skin may be tattooed. For example, after applying tattoo ink to a tattoo needle, a practitioner may apply a tattoo by penetrating the tattoo needle into the skin. As the practitioner repeats this process, a specific pattern is tattooed on the skin.

Since the process of applying the ink to the needle and penetrating the skin is carried out over a long time, the tattoo treatment takes a long time, which may prolong the pain of the subject. In addition, since the tattoo is performed on the dermis of the subject, it is difficult to remove the tattoo once it is engraved, and the cost of the tattoo treatment may increase as the tattoo treatment time is prolonged.

As an alternative to solving the issues of tattoos, methods such as henna, body painting, and stickers are being used, and furthermore, research and development of printer products that can print specific designs on the skin are also being carried out.

In the case of a printer product, it has the advantage in that a user's desired image can be easily printed on the skin and various images can be used. However, since the skin is not flat, a gap between a nozzle of the printer product and the skin is not kept constant, which may cause many differences between the original image that the user wants to be printed and the image printed on the skin.

On the other hand, home inkjet printers are being used to print on paper and photo paper. In general, however, the home inkjet printers should use a specified size and type of paper.

Therefore, in order to perform printing regardless of the size or type of paper such as diaries, notebooks, and stickers, a portable printer with movable nozzles and rollers is required. This portable printer has a feature similar to a portable printer used for the skin in that it moves positions of the nozzle and roller to a place where the user wants to print. However, since the skin and paper have different properties such as soft and hard, respectively, there was an issue in that it was impossible to use the same roller and nozzle structures for both purposes.

DISCLOSURE OF THE INVENTION

Technical Goals

The present disclosure has been created to solve the issues of the related art as described above, and an object of the present disclosure is to provide a portable printer capable of printing a clear image on the skin by maintaining a constant distance between the skin and the nozzle. In addition, an object of the present disclosure is to provide a portable printer capable of appropriately changing a distance between the nozzle and a surface of a target so that smooth printing is possible for both when the target on which a printing material is to be printed is soft, such as skin, and hard, such as paper.

Technical Solutions

In accordance with an aspect of the present disclosure, there is provided a portable printer including: a main body in a portable form which is capable of accommodating a cartridge having a nozzle configured to deliver a printing material to a target; a seating part which is provided to be exposed to an outside from a lower portion of the main body to face a surface of the target and at least partially surrounds the nozzle; and a roller provided respectively at the front and rear of the nozzle at the lower portion of the main body with respect to a direction in which the main body moves along the surface of the target to deliver the printing material to the target, wherein the roller includes a first roller provided at the front of the nozzle with respect to the direction of movement of the main body; and a second roller provided at the rear of the nozzle with respect to the direction of movement of the main body, and a height difference between a lower end of at least the first roller of the first roller and the second roller and the nozzle is 4.5 mm to 8.5 mm.

Specifically, the first roller may include at least one first rotation shaft provided parallel to the nozzle; and at least one first wheel provided on the first rotation shaft, and the second roller may include at least one second rotation shaft provided parallel to the nozzle; and at least one second wheel provided on the second rotation shaft.

Specifically, the portable printer may be provided for both skin and paper use by delivering the printing material to the target having a soft surface or a hard surface by the nozzle.

Specifically, the first rotation shaft and the first wheel may be provided to overlap the nozzle along the direction of movement of the main body, and a plurality of the second rotation shafts and a plurality of the second wheels may be provided and each may be provided at a position deviated from the nozzle along the direction of movement of the main body.

Specifically, the first rotation shaft and the second rotation shaft may be provided to overlap the nozzle along the direction of movement of the main body, and a plurality of the first wheels and a plurality of the second wheels may be provided and each may be provided at a position deviated from the nozzle along the direction of movement of the main body.

Specifically, the first rotation shaft and the first wheel may be provided to overlap the nozzle along the direction of movement of the main body, the second rotation shaft and the second wheel may be provided at a position deviated from the nozzle along the direction of movement of the main body, and the roller may further include a third roller provided on a side of the nozzle with respect to the direction of movement of the main body.

Specifically, at least a portion of the roller in contact with the surface of the target may be formed of a soft material.

Specifically, on a plane, a separation distance between the first roller and the nozzle may be the same as a separation distance between the second roller and the nozzle.

Specifically, on the plane, a separation distance between the roller and the nozzle may be 6.9 mm to 13.1 mm.

Specifically, an optical sensor provided in at least one of the front and rear of the seating part along the direction of movement of the main body and checking a center line of the target in correspondence with the center of the nozzle may be further included.

Specifically, the optical sensor may be provided between the plurality of second wheels with respect to the direction of movement of the main body.

Specifically, the optical sensor may be provided at the rear of the second roller with respect to the direction of movement of the main body.

Specifically, the printing material may be a printing solution having a viscosity of 4 mPa*s to 6 mPa*s.

In accordance with another aspect of the present disclosure, there is provided a portable printer including: a main body in a portable form which is capable of accommodating a cartridge having a nozzle configured to deliver a printing material to a target having a soft or hard surface; a seating part which is provided to be exposed to an outside from a lower portion of the main body to face the surface of the target and at least partially surrounds the nozzle; a roller provided respectively at the front and rear of the nozzle at the lower portion of the main body with respect to a direction in which the main body moves along the surface of the target to deliver the printing material to the target; and a printing adjustment unit configured to adjust a height difference between the nozzle and the roller to adjust a height difference between the nozzle and the surface of the target.

Specifically, the height difference between the nozzle and the roller may be adjusted by moving at least the roller of the seating part and the roller in inner and outer directions of the main body.

Specifically, the portable printer may be provided for both skin and paper use by adjusting the height difference between the nozzle and the surface of the target by the printing adjustment unit.

Specifically, the roller may be provided in the seating part and move integrally with the seating part by the printing adjustment unit.

Specifically, the nozzle may be disposed closer to an inside of the main body compared to the roller, and the printing adjustment unit may be configured to move the roller to a protruding position to adjust a height between the nozzle and the roller to 6.0 mm to 7.0 mm when delivering the printing material to soft skin, and move the roller to a retracted position to adjust the height between the nozzle and the roller to 0.5 mm to 2.5 mm when delivering the printing material to hard paper.

Specifically, the roller may include a first roller provided at the front of the nozzle with respect to the direction of movement of the main body; and a second roller provided at the rear of the nozzle with respect to the direction of movement of the main body, and the first roller and the second roller may maintain the same height difference with the nozzle when moving the roller by the printing adjustment unit.

Specifically, the printing adjustment unit may include an elastic member which is provided between the main body and the seating part and has an elastic force to maintain the seating part in a restoration position that is one of a retracted position and a protruding position with respect to the main body; and an operating member which is provided in the seating part and places the seating part in a change position of the other one of the retracted position and the protruding position with respect to the main body by external manipulation.

Specifically, the elastic member may be a tension spring to maintain the seating part in the retracted position, and the operating member may be deformed to push the main body out of the seating part while tensioning the elastic member by external manipulation so that the seating part is placed in the protruding position.

Specifically, the operating member may include an operation button exposed to the outside and movable in a horizontal direction; and a cam provided between the seating part and the main body, wherein, when one end of the cam is rotated by the operation button, a height of the other end facing the main body may be varied.

Specifically, the elastic member may be a tension spring to maintain the seating part in the retracted position, and the operating member may engage with a locking protrusion of the main body to maintain the seating part in the protruding position, or when the operating member is disengaged from the locking protrusion of the main body by external manipulation, the seating part may be moved by the elastic member to be placed in the retracted position.

Specifically, the operating member may include an operation button configured to limit movement of the seating part by the elastic member with its one end exposed to the outside and the other end in contact with the locking protrusion, and allow movement of the seating part by the elastic member when the one end of the operation button is pressed and the other end is rotated so as to be deviated from the locking protrusion.

Specifically, a plurality of the operation buttons may be provided, and one end of each of the plurality of operation buttons may protrude at a uniform height from one surface of the seating part facing the surface of the target.

Specifically, the operation button may be provided so that its one end protrudes relatively more than the roller from the seating part, and may be pressed by the target having the hard surface to be disengaged from the locking protrusion.

Specifically, the portable printer may further include a carriage provided inside the main body and in which the cartridge is detachably coupled; and a cartridge replacement unit configured to move at least the cartridge of the carriage and the cartridge within the main body.

Specifically, the cartridge replacement unit may include a replacement button exposed to the outside and movable in a horizontal direction; and a cam provided between the carriage and the main body, wherein when one end of the cam is rotated by the replacement button, a height of the other end facing the carriage is varied.

Specifically, the cartridge replacement unit may further include a pressing protrusion provided on another side of the cam, the carriage may have a slit that allows penetration of the pressing projection, and the pressing protrusion may penetrate the slit and pushes the cartridge with respect to the carriage when the cam rotates at a predetermined angle or more.

Specifically, the printing material may be a printing solution having a viscosity of 4 mPa*s to 6 mPa*s.

In accordance with another aspect of the present disclosure, there is provided a portable printer including: a main body in a portable form which is capable of accommodating a cartridge having a nozzle configured to deliver a printing material to a target having a soft or hard surface; a roller provided respectively at the front and rear of the nozzle at the lower portion of the main body with respect to a direction in which the main body moves along the surface of the target to deliver the printing material to the target; and a printing adjustment unit configured to adjust a height difference between the nozzle and the roller to adjust a height difference between the nozzle and the surface of the target, wherein the printing adjustment unit includes an elastic member having an elastic force to maintain the roller in a restoration position that is one of a retracted position and a protruding position with respect to the main body; and an operating member which is provided in the main body and places the roller in a change position of the other one of the retracted position and the protruding position with respect to the main body by external manipulation.

Specifically, the portable printer may further include a seating part which is provided to be exposed to an outside from a lower portion of the main body to face the surface of the target and at least partially surrounds the nozzle, and the roller may be provided in the seating part and may move integrally with the seating part by the printing adjustment unit.

Specifically, the printing adjustment unit may be a compression spring for maintaining the seating part in the protruding position, and the operating member may allow the seating part to be moved by the elastic member and placed in the protruding position when engagement with the seating part is released by external manipulation.

Specifically, the seating part may be provided with a locking protrusion on one side facing the operating member, and the operating member include an operation button configured to limit movement of the seating part by the elastic member with its one end operable from the outside and the other end in contact with the locking protrusion, and allow movement of the seating part by the elastic member when the one end of the operation button is manipulated and the other end is moved so as to be deviated from the locking protrusion.

In accordance with another aspect of the present disclosure, there is provided a portable printer including: a main body in a portable form which is capable of accommodating a cartridge having a nozzle configured to deliver a printing material to a target having a soft or hard surface; a roller provided respectively at the front and rear of the nozzle at the lower portion of the main body with respect to a direction in which the main body moves along the surface of the target to deliver the printing material to the target; and a printing adjustment unit configured to adjust a height difference between the nozzle and the roller to adjust a height difference between the nozzle and the surface of the target, wherein the printing adjustment unit includes an adjustment piece including a first path through which a locking pin provided in the main body moves when moving in a direction in which it is retracted into the main body, a groove which is connected to an end of the first path and in which the locking pin is seated and movement in a direction of protruding from the main body is restricted, and a second path connecting the end of the groove and one end of the first path; and an elastic member having an elastic force to maintain the roller in a restoration position, which is one of a retracted position and a protruding position with respect to the main body.

Specifically, the portable printer may further include a seating part which is provided to be exposed to an outside from a lower portion of the main body to face the surface of the target and at least partially surrounds the nozzle, and the roller may be provided in the seating part and may move integrally with the seating part by the printing adjustment unit.

Specifically, when the seating part is retracted into the main body by external manipulation, the locking pin may be seated in the groove beyond the end of the first path of the adjustment piece and the seating part may be placed in the retracted position, and when the seating part is further retracted into the main body by external manipulation, the locking pin may disengage with the groove and return to the one end of the first path along the second path and the seating part may be placed in the protruding position.

In accordance with another aspect of the present disclosure, there is provided a portable printer including: a main body in a portable form which is capable of accommodating a cartridge having a nozzle configured to deliver a printing material to a target having a soft or hard surface; a roller provided respectively at the front and rear of the nozzle at the lower portion of the main body with respect to a direction in which the main body moves along the surface of the target to deliver the printing material to the target; and a printing adjustment unit configured to adjust a height difference between the nozzle and the roller to adjust a height difference between the nozzle and the surface of the target, wherein the printing adjustment unit includes an adjustment piece which has a hole for accommodating a rotating protrusion provided in the main body and is formed to move translationally by eccentric rotation of the rotating protrusion; and an elastic member having an elastic force to maintain the roller in a restoring position, which is one of a retracted position and a protruding position with respect to the main body.

Specifically, the portable printer may further include a seating part which is provided to be exposed to an outside from a lower portion of the main body to face the surface of the target and at least partially surrounds the nozzle, and the roller may be provided in the seating part and may move integrally with the seating part by the printing adjustment unit.

Specifically, when the rotating protrusion rotates eccentrically toward the inner side of the main body, the elastic member may be compressed and the seating part may move to the retracted position by the adjustment piece, and when the rotating protrusion rotates eccentrically toward the outer side of the main body, the seating part may move to the protruding position by the adjustment piece and the elastic member.

In accordance with another aspect of the present disclosure, there is provided a portable printer including: a main body in a portable form which is capable of accommodating a cartridge having a nozzle configured to deliver a printing material to a target having a soft or hard surface; a roller provided respectively at the front and rear of the nozzle at the lower portion of the main body with respect to a direction in which the main body moves along the surface of the target to deliver the printing material to the target; a printing adjustment unit configured to adjust a height difference between the nozzle and the roller to adjust a height difference between the nozzle and the surface of the target by moving the roller to one of the retracted position and the protruding position with respect to the main body; and a printer cover that is detachable from the main body and seals the nozzle, wherein the printer cover includes an interference member that interferes with the printing adjustment unit to place the roller in the retracted position.

Specifically, the portable printer may further include a seating part which is provided to be exposed to an outside from a lower portion of the main body to face the surface of the target and at least partially surrounds the nozzle, the roller may be provided in the seating part and may move integrally with the seating part by the printing adjustment unit, and the printing adjustment unit may include an elastic member which is provided between the main body and the seating part and has an elastic force to maintain the seating part in a restoration position that is one of a retracted position and a protruding position with respect to the main body; and an operating member which is provided in the seating part and places the seating part in a change position of the other one of the retracted position and the protruding position with respect to the main body by external manipulation.

Specifically, the interference member may interfere with the operating member so that the seating part is placed in the retracted position.

Specifically, the elastic member may be a tension spring to maintain the seating part in the retracted position, and the operating member may be deformed to push the main body out of the seating part while tensioning the elastic member by external manipulation so that the seating part is placed in the protruding position.

Specifically, when the operating member is in a state where it is deformed to push the main body from the seating part while tensioning the elastic member, the interference member may move the operating member so that the seating part is restored to the retracted position by the elastic member while the printer cover seals the nozzle.

Specifically, one end of the interference member may be provided to be operable from the outside of the printer cover and the other end may be provided adjacent to the operating member, and in a state where the operating member is deformed to push the main body from the seating part while tensioning the elastic member, manipulation of one end of the interference member may allow the other end to move the operating member so that the seating part may be restored to the retracted position by the elastic member.

Specifically, the printing material may be a printing solution having a viscosity of 4 mPa*s to 6 mPa*s.

Advantageous Effects

A portable printer according to the present disclosure may print a clear image on the skin by maintaining a constant optimal distance between the skin and the nozzle.

In addition, the portable printer according to the present disclosure may be able to appropriately change the distance between the nozzle and the surface of the target by adjusting a degree of protrusion of a head part, so that printing quality can be guaranteed even if the hardness of the target is different and the portable printer can be used for both skin and paper.

BRIEF DESCRIPTION OF DRAWINGS

FIG. 13 is a perspective view of the portable printer according to the fourth embodiment of the present disclosure.

FIG. 19 is a side view of the portable printer according to the fifth embodiment of the present disclosure.

FIG. 39 is a cross-sectional view of a portable printer according to an eleventh embodiment of the present disclosure.

FIG. 42 is a cross-sectional view of a portable printer according to a fourteenth embodiment of the present disclosure.

FIG. 47 is a cross-sectional view of a portable printer according to a nineteenth embodiment of the present disclosure.

FIG. 49 is a schematic diagram of a portable printer according to a 21st embodiment of the present disclosure.

FIG. 50 is a cross-sectional view of the portable printer according to the 21st embodiment of the present disclosure.

FIG. 51 is a cross-sectional view of the portable printer according to the 21st embodiment of the present disclosure.

FIG. 68 is a partial perspective view of the portable printer according to the 25th embodiment of the present disclosure.

BEST MODE FOR CARRYING OUT THE INVENTION

Figure 1:
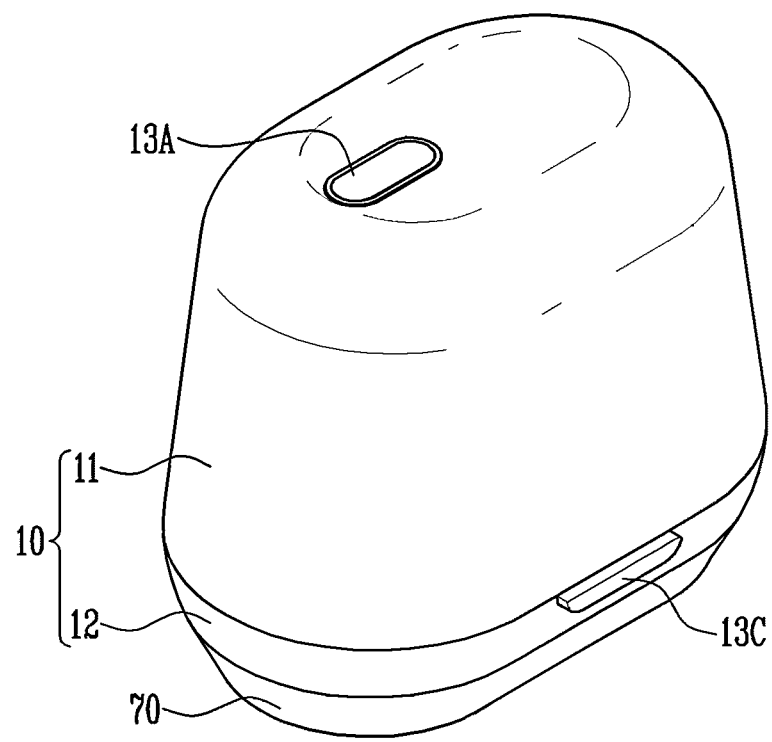
FIG. 1 is a perspective view of a portable printer according to a first embodiment of the present disclosure.

The objects, specific advantages and novel features of the present disclosure will become more apparent from the following detailed description and preferred embodiments taken in conjunction with the accompanying drawings. In the present specification, in adding reference numerals to components of each drawing, it should be noted that only the same components are given the same numeral as possible even though they are indicated on different drawings. In addition, in describing the present disclosure, if it is determined that a detailed description of a related known art may unnecessarily obscure the subject matter of the present invention, the detailed description thereof will be omitted.

For reference, a portable printer described herein may deliver a printing material to a target, and the target may have a soft or hard surface. For example, the target may be soft skin, hard paper, or the like (including base paper that can be attached to skin or nails).

In the portable printer according to the present disclosure, some components may be changed by movement or the like depending on the hardness of the target, and the meaning of soft or hard to be described later is relative. For example, in the present disclosure, a user's skin (regardless of location) may be defined as a soft target, and an object harder than the skin may be defined as a hard target. The target referred to as skin hereinafter is for convenience of description and can of course be interpreted as an target such as paper.

In addition, in the present disclosure, an image includes a letter, number, figure, pattern, or the like, or is a combination thereof and its shape, form, color, and the like are not limited. In addition, the image does not include only one consisting of colors identifiable with the naked eye, but also includes one consisting of colors identifiable only through special equipment.

Hereinafter, with reference to the accompanying drawings, preferred embodiments of the present disclosure will be described in detail.

Figure 2:
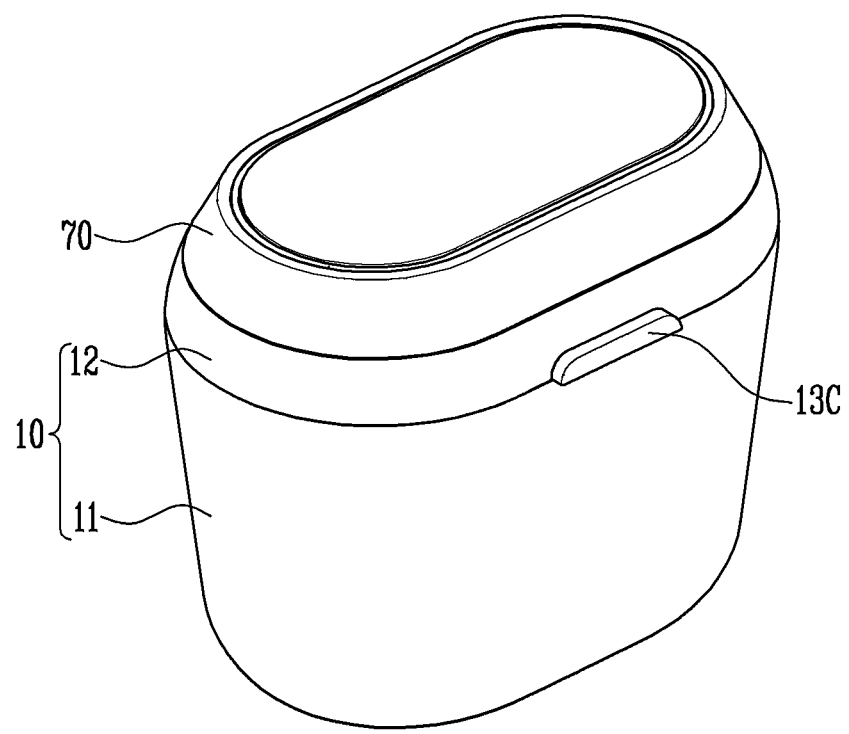
FIG. 2 is a perspective view of the portable printer according to the first embodiment of the present disclosure.
Figure 3:
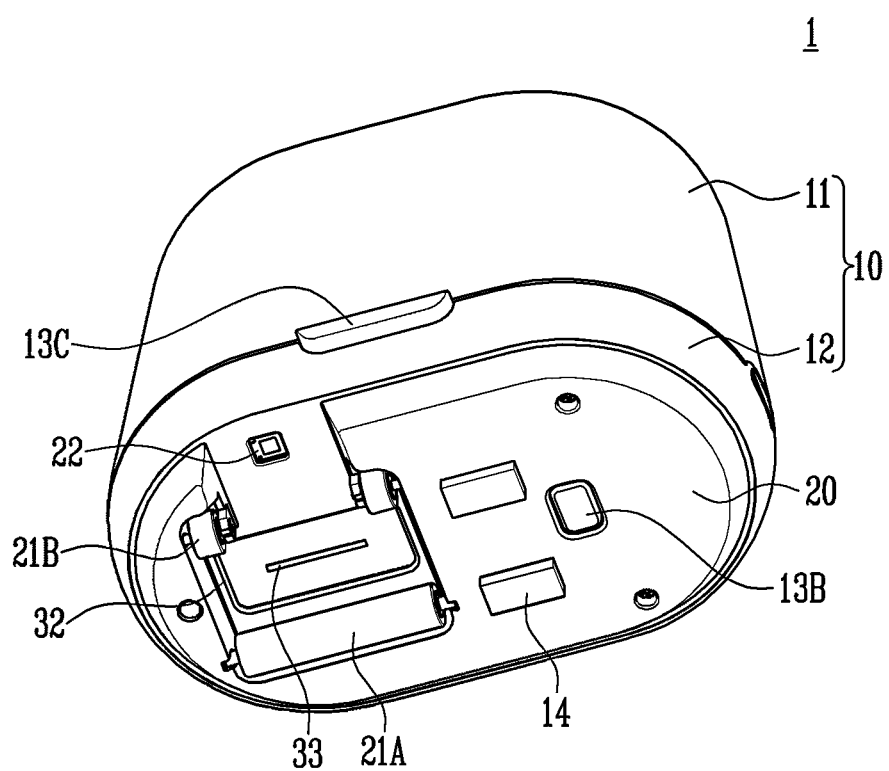
FIG. 3 is a perspective view of the portable printer according to the first embodiment of the present disclosure.

FIGS. 1 to 3 are perspective views of a portable printer according to a first embodiment of the present disclosure.

FIGS. 1 and 2 illustrate a state in which a printer cover 70 is provided and FIG. 3 illustrates a state in which the printer cover 70 is removed.

Figure 4:
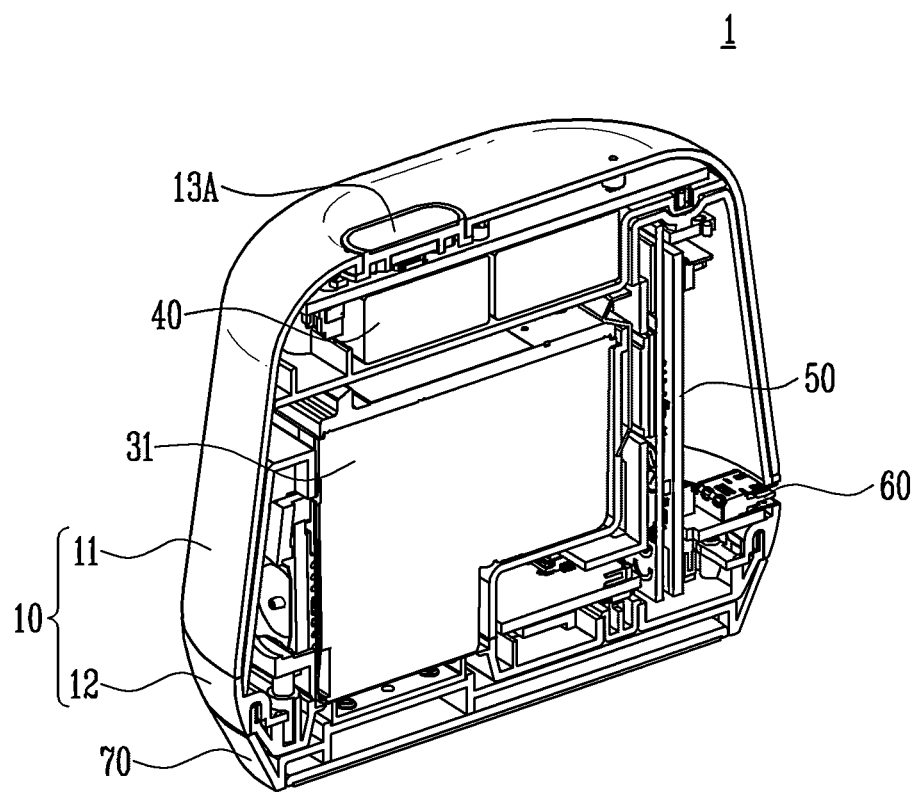
FIG. 4 is a cutaway perspective view of the portable printer according to the first embodiment of the present disclosure.
Figure 5:
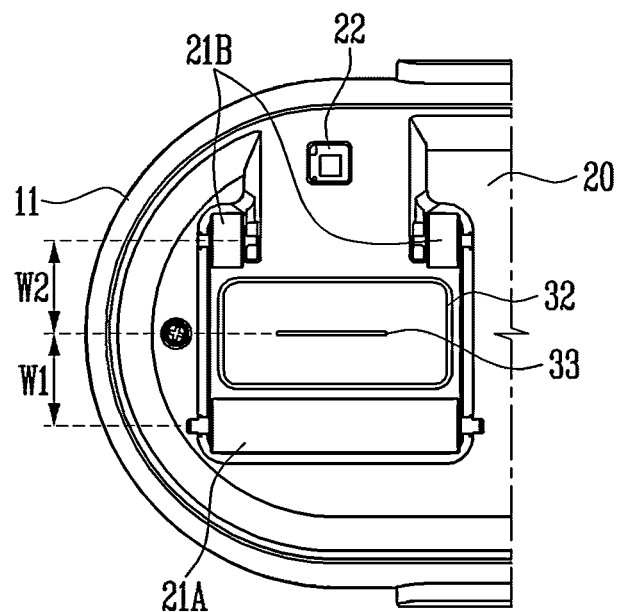
FIG. 5 is a bottom plan view of the portable printer according to the first embodiment of the present disclosure.
Figure 6:
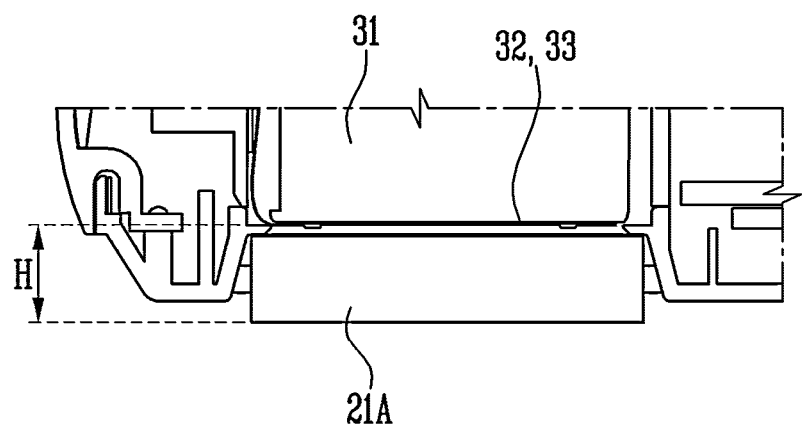
FIG. 6 is a partial cross-sectional view of the portable printer according to the first embodiment of the present disclosure.

In addition, FIG. 4 is cutaway perspective view of the portable printer according to the first embodiment of the present disclosure, FIG. 5 is a bottom plan view of the portable printer according to the first embodiment of the present disclosure, and FIG. 6 is a partial cross-sectional view of the portable printer according to the first embodiment of the present disclosure.

Figure 7:
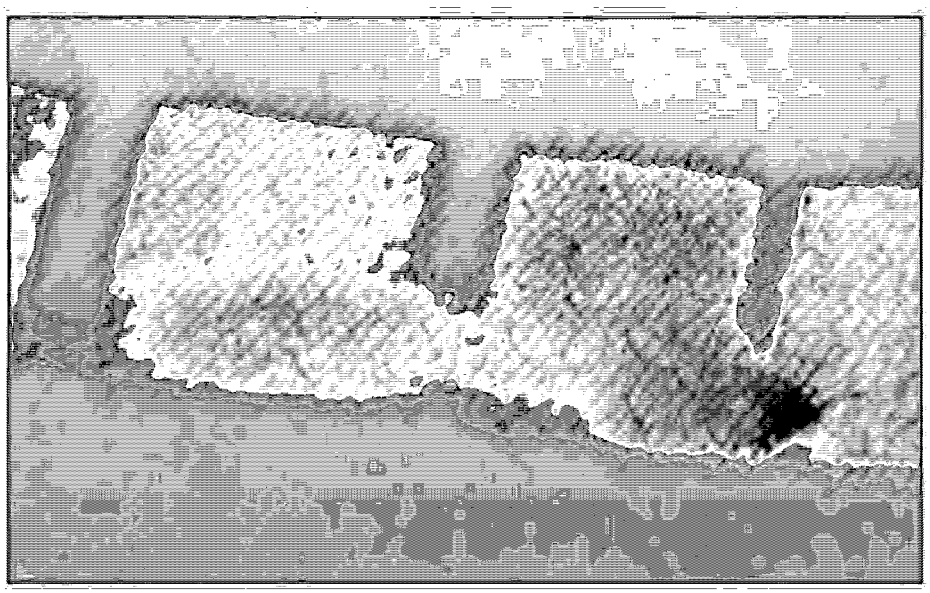
FIG. 7 is a diagram illustrating a printing image of a first height of the portable printer according to the first embodiment of the present disclosure.
Figure 8:
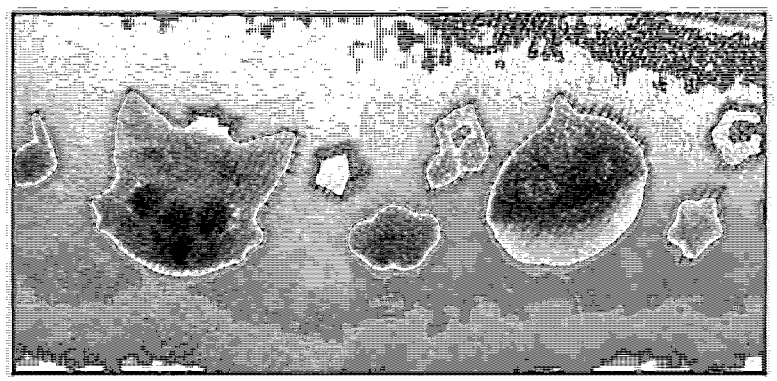
FIG. 8 is a diagram illustrating a printing image of a second height of the portable printer according to the first embodiment of the present disclosure.
Figure 9:
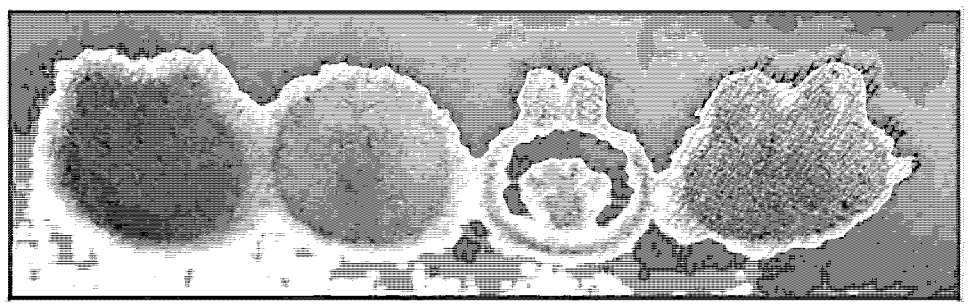
FIG. 9 is a diagram illustrating a printing image of a third height of the portable printer according to the first embodiment of the present disclosure.

FIG. 7 is a diagram illustrating a printing image of a first height of the portable printer according to the first embodiment of the present disclosure, FIG. 8 is a diagram illustrating a printing image of a second height of the portable printer according to the first embodiment of the present disclosure, and FIG. 9 is a diagram illustrating a printing image of a third height of the portable printer according to the first embodiment of the present disclosure.

In this case, the first to third heights are heights between a roller 21 and a nozzle 33, and the first height is less than 4.5 mm, the second height is 4.5 mm to 8.5 mm, and the third height is more than 8.5 mm.

Referring to FIGS. 1 to 9, a portable printer 1 according to the first embodiment of the present disclosure includes a main body 10, a seating part 20, the roller 21, and the printer cover 70.

The main body 10 accommodates a cartridge 31 having the nozzle 33. The nozzle 33 may be a part that delivers a printing material to a target having a soft or hard surface. The main body 10 may have a portable shape, which means that its size, weight, and the like are generally recognized for portability.

The main body 10 may form the appearance of the portable printer 1. The main body 10 may have various shapes that the user can grasp. For example, the main body 10 may have a box shape, and an edge portion may be curved to improve portability.

The main body 10 may include an upper body 11 and a lower body 12. The upper body 11 and the lower body 12 may be detachable by a separation button 13C provided on one side.

At this time, the separation button 13C may be provided only on one side of the main body 10. The separation button 13C may guide a movement direction of the main body 10. In other words, the separation button 13C is disposed forward based on the direction in which the main body 10 moves for printing, and when the user senses the separation button 13C by touch or the like, a printing start position by the main body 10 may be visually identified.

In addition, the separation button 13C is provided with a structure capable of emitting light or transmitting light by an LED or the like. When printing starts, the separation button 13C may light up through a light source to increase user convenience.

The upper body 11 provides an internal space in which various components for operation of the portable printer 1 can be accommodated. In other words, the upper body 11 may have a structure in which a lower portion may be opened so that various components for operation of the portable printer 1 can be put in and out.

In this embodiment, the structure in which the lower portion of the upper body 11 is opened is described as an example, but is not limited thereto. For example, the upper body 11 has a structure in which an upper portion is opened, and various components for operation of the portable printer 1 may be put in and out. In this case, the lower body 12 may be detachably coupled to the upper portion of the upper body 11.

The lower body 12 may be coupled to the open lower portion of the upper body 11 to prevent various components for operation of the portable printer 1 from being exposed to the outside. Of course, the lower body 12 may have an open lower portion so that the seating part 20, the roller 21, and the nozzle 33, which are components for printing of the portable printer 1, may be exposed to the outside.

The exterior of the main body 10 may be provided with at least one operation button for operation of the portable printer 1. The operation button may include a printing button 13A and a power button 13B.

The printing button 13A may be provided on the upper portion of the upper body 11. The printing button 13A may cause the nozzle 33 to discharge the printing material by the user's operation. The printing button 13A is provided on the upper portion of the upper body 11 in FIG. 2, but is not limited thereto. For example, the printing button 13A may be provided on one side of the exterior of the upper body 11 and may be variously disposed at a position convenient for the user.

The power button 13B may be provided in the lower portion of the lower body 12. The power button 13B may turn on/off the power of the portable printer 1.

FIG. 3 illustrates an example in which the power button 13B is provided in the lower portion of the lower body 12, but the present disclosure is not limited thereto. For example, the power button 13B may be provided on one side of the lower body 12 and may be variously disposed at a position convenient for the user.

At least one lamp 14 may be provided on a part of the exterior of the lower body 12. The lamp 14 may display an operating state of the portable printer 1. FIG. 3 illustrates an example in which the lamp 14 is provided in the lower portion of the lower body 12, but the present disclosure is not limited thereto. For example, the lamp 14 may be provided on one side of the lower housing and may be variously disposed at a position where the user can easily recognize the operating state of the portable printer 1.

In addition, in the internal space of the upper body 11, various components for operation of the portable printer 1 may be provided. For example, in the internal space of the upper body 11, a cartridge 31, a battery 40, a controller 50, and the like may be provided.

The battery 40 may be implemented as a secondary battery such as a lithium battery capable of charging and discharging, and at least one battery 40 may be provided. The battery 40 may provide power necessary for operation of the portable printer 1.

The controller 50 may control the operation of the portable printer 1. For example, the controller 50 may turn on/off the power of the portable printer 1 by the user's manipulation of the power button 13B.

The controller 50 may allow the printing material accommodated in the cartridge 31 to be discharged through the nozzle 33 through a signal by the user's manipulation of the printing button 13A to print an image on human skin.

The controller 50 may receive and store an image to be printed from the outside using a communication unit 60. Here, the communication unit 60 may be implemented with a USB terminal, a Bluetooth module, or a WIFI transceiver module. In other words, the communication unit 60 may receive an image to be printed on a target from an external device through wired or wireless communication.

The cartridge 31 may accommodate the printing material necessary for printing, and may be provided with the nozzle 33 configured to discharge the printing material in its lower portion. The nozzle 33 may have a shape of a slit 240 extending in a direction perpendicular to the movement direction of the main body 10, and a periphery of the nozzle 33 may be defined as a head 32.

The printing material may be a printing solution having a viscosity of 4 mPa*s to 6 mPa*s, but is not limited thereto. The printing material may include at least one of at least a liquid and a solid (powder, etc.), and may include a gaseous component. It should be noted that even if it is described below as a printing solution, it does not necessarily mean that it is made of 100% liquid components.

At least one cartridge 31 may be provided. For example, one cartridge 31 may be provided by accommodating a printing material of single color. If the cartridge 31 accommodates the printing material of single color, the portable printer 1 may print an image consisting of the single color on the target.

In addition, the cartridge 31 may have a plurality of accommodating parts (not shown) that accommodate printing materials of different colors, and may discharge the printing materials through the nozzle 33. Therefore, when the cartridge 31 has the plurality of accommodating parts that accommodate the printing materials of different colors, the portable printer 1 may print a color image on the target.

Further, a plurality of the cartridges 31 may be provided, and each cartridge 31 may accommodate the printing materials of different colors. In addition, when the plurality of cartridges 31 are provided, the plurality of cartridges 31 may be configured as one module.

The cartridge 31 may be accommodated in a carriage 30 provided in the main body 10, the carriage 30 has a configuration in which the cartridge 31 is detachably seated, and the carriage 30 may have a shape in which at least a portion thereof is opened such that the head 32 and the nozzle 33 of the cartridge 31 are downwardly exposed through the open lower portion of the lower body 12.

The carriage 30 may have a shape corresponding to the shape of the cartridge 31, and one or more cartridges 31 may be seated in one carriage 30. Of course, the carriage 30 may have a partially partitioned structure so that the plurality of cartridges 31 may be seated individually.

The printing solution according to the present disclosure may have a viscosity of 4 mPa*s to 6 mPa*s. If the viscosity of the printing solution is less than 4 mPa*s, the printing solution may leak from the nozzle 33 or flow on the skin after being discharged onto the skin. In addition, if the viscosity of the printing solution exceeds 6 mPa*s, it may take a long time to dry after the printing solution is discharged onto the skin. In particular, when the viscosity of the printing solution exceeds 10 mPa*s, the printing solution may not be discharged from the nozzle 33, or the printing solution may be adsorbed on the nozzle 33 and the nozzle 33 may be closed.

The printing solution may include a pigment or dye and a solvent to disperse the pigment or dye. The solvent may include purified water and an organic solvent, and the organic solvent may determine the viscosity of the printing solution.

Here, the organic solvent may be a nonvolatile organic solvent and be a substance that is not easily separated when mixed with water because its molecular structure includes a hydrophilic group. For example, the organic solvent may include at least one of PEG-8, glycerin, dipropylene glycol, butylene glycol, propylene glycol, and propanediol.

When the content of the organic solvent in the printing solution is 10 wt % or less, the viscosity of the printing solution may be less than 4 mPa*s, and thus the printing solution may leak from the nozzle 33 or flow on the skin after being discharged to the skin. In addition, when the content of the organic solvent in the printing solution is 40 wt % or more, the viscosity of the printing solution may exceed 6 mPa*s, and thus the printing solution is not discharged from the nozzle 33, or it may take a long time to dry the printing solution. In addition, when the content of a single organic solvent in the printing solution exceeds 20 wt %, the printing solution may not settle on the skin, and may flow on the skin or increase stickiness.

Table 1 below is a table showing the composition of the printing solution of each of Examples 1 to 4 and Comparative Examples 1 to 10, and Table 2 is a table explaining characteristic evaluation results of Examples 1 to 4 and Comparative Examples 1 to 10.

TABLE 1

Composition of printing solution of each of Examples 1 to 4 and Comparative Examples 1 to 10

| Category Name of ingredient | Purified water | Organic solvent PEG-8 | Organic solvent Glycerin | Surfactant Polysorbate 20 | Dye CI 17200 |
| --- | --- | --- | --- | --- | --- |
| Example 1 | to 100 | 20 | — | 0.2 | 4 |
| Example 2 | to 100 | — | 20 | 0.2 | 4 |
| Example 3 | to 100 | 10 | 10 | 0.2 | 4 |
| Example 4 | to 100 | 15 | 10 | 0.2 | 4 |
| Comparative Example 1 | to 100 | 5 | — | 0.2 | 4 |
| Comparative Example 2 | to 100 | 10 | — | 0.2 | 4 |
| Comparative Example 3 | to 100 | 30 | — | 0.2 | 4 |
| Comparative Example 4 | to 100 | 40 | — | 0.2 | 4 |
| Comparative Example 5 | to 100 | — | 5 | 0.2 | 4 |
| Comparative Example 6 | to 100 | — | 10 | 0.2 | 4 |
| Comparative Example 7 | to 100 | — | 30 | 0.2 | 4 |
| Comparative Example 8 | to 100 | — | 40 | 0.2 | 4 |
| Comparative Example 9 | to 100 | 5 | 5 | 0.2 | 4 |
| Comparative example10 | to 100 | 20 | 20 | 0.2 | 4 |

In Table 1, Examples 1 to 4 and Comparative Examples 1 to are printing solutions prepared by weighing according to the components and contents listed in Table 1, stirring at 300 rpm for 20 minutes, defoaming, and filtering with a filter having a pore size of 0.45 μm.

TABLE 2

Characteristic evaluation results of Examples 1 to 4 and Comparative Examples 1 to 10

| | Viscosity (mPa*s) | Leakage | Discharge | Smear when printing | Smear after drying |
| --- | --- | --- | --- | --- | --- |
| Example 1 | 4.5 | X | ○ | X | X |
| Example 2 | 4 | X | ○ | X | X |
| Example 3 | 4 | X | ○ | X | X |

TABLE 2-continued

Characteristic evaluation results of Examples
1 to 4 and Comparative Examples 1 to 10

| | Viscosity (mPa*s) | Leakage | Discharge | Smear when printing | Smear after drying |
|---|---|---|---|---|---|
| Example 4 | 4.5 | X | ○ | X | X |
| Comparative Example 1 | 3 | ○ | ○ | ○ | X |
| Comparative Example 2 | 3.5 | ○ | ○ | ○ | X |
| Comparative Example 3 | 5 | X | Δ | X | ○ |
| Comparative Example 4 | 6.5 | X | X | X | ○ |
| Comparative Example 5 | 3 | ○ | ○ | ○ | X |
| Comparative Example 6 | 3.5 | ○ | ○ | ○ | X |
| Comparative Example 7 | 4.5 | X | Δ | X | ○ |
| Comparative Example 8 | 5.5 | X | X | X | ○ |
| Comparative Example 9 | 3.5 | ○ | ○ | ○ | X |
| Comparative example10 | 6.5 | X | X | X | ○ |

In Table 2, the viscosity evaluation of the printing solution is measured with a Brookfield DV-E viscometer at Spindle Number 1, 60 rpm, and room temperature conditions, and is expressed in mPa*s. The evaluation of leakage of the printing solution is carried out by filling the HP62 cartridge 31 with 5 ml of the printing solution and leaving the nozzle 33 facing down at room temperature for 3 days, and in Table 2, 'O' is marked when leakage occurs, and 'X' is marked when no leakage occurs.

The discharge evaluation of the printing solution is carried out by mounting the cartridge 31 filled with the printing solution to the apparatus and performing image printing. In particular, printing is repeated 10 times to check the number of clearly printed images, and when the clear image exceeds 75%, 'O' is marked, when the clear image is 50% to 75%, 'A' is marked, and when the clear image is less than 50%, 'X' is marked.

The smear evaluation during printing of the printing solution checks the clarity of the image immediately after printing the image on a forearm part using the portable printer 1 filled with the printing solution. When smear occurs in the printed image, 'O' is marked, and when no smear occurs, 'X' is marked.

The smear evaluation after drying of the printing solution checks a drying state and smearing of the printing solution by printing an image, drying it for 1 minute, and rubbing it three times. When smear occurs in the image dried for one (1) minute, 'O' is marked, and when no smear occurs, 'X' is marked.

Referring to Table 1 and Table 2 described above, it can be seen that leakage occurs in Comparative Example 1, Comparative Example 2, Comparative Example 5, Comparative Example 6, and Comparative Example 9 in which the content of organic solvent is 10 wt % or less in the entire printing solution.

In addition, it can be seen that discharge of the printing solution from the cartridge 31 is not smooth in Comparative Example 4, Comparative Example 8, and Comparative Example 10 in which the content of organic solvent is 40 wt % or more in the entire printing solution.

It can be seen that image smearing occurs due to flow on the skin after the printing solution is discharged onto the skin in Comparative Example 1, Comparative Example 2, Comparative Example, Comparative Example 6, and Comparative Example 9 in which the content of organic solvent is 10 wt % or less in the entire printing solution.

In Comparative Example 3, Comparative Example 4, Comparative Example 7, and Comparative Example 8 in which the content of a single organic solvent exceeds 20 wt % in the entire printing solution, it can be seen that smearing occurs when rubbed due to insufficient drying.

The seating part 20 is provided to be exposed to the outside from a lower portion of the main body 10 and faces the surface of the target. The seating part 20 may be exposed or protruding downward from the lower portion of the lower body 12 and may be provided to at least partially surround the nozzle 33.

The cartridge 31 may be able to move up and down together with the seating part 20. When the cartridge 31 is capable of moving up and down together with the seating part 20, even if the user presses it during use of the portable printer 1, a distance between the skin and the nozzle 33 may be maintained to print a clear image.

In addition, a distance sensor may be provided on one side of the cartridge 31 for measuring the distance between the skin and the nozzle 33. The distance sensor may measure the distance between the skin and the nozzle 33 and transmit the measured distance value to the controller 50.

In addition, the controller 50 may adjust the distance between the skin and the nozzle 33 by using the distance between the skin and the nozzle 33 transmitted from the distance sensor provided on one side of the cartridge 31. In other words, when the distance between the skin and the nozzle 33 measured by the distance sensor deviates from an appropriate value, the controller 50 may adjust the distance between the skin and the nozzle 33 by moving up and down the cartridge 31 and the seating part 20.

The seating part 20 may be provided in the lower portion of the lower body 12, in other words, on a surface facing the skin in the lower body 12 during image printing of the portable printer 1. The seating part 20 may expose the nozzle 33 provided in the lower portion of the cartridge 31.

In addition, the seating part 20 may be able to move up and down together with the cartridge 31. Here, the seating part 20 may have a rack and pinion structure to move up and down. In particular, the seating part 20 may be connected to the rack and may be possible to move up and down by rotation of the pinion. When the seating part 20 is capable of moving up and down with the cartridge 31, even if the user presses it during the use of the portable printer 1, the distance between the skin and the nozzle 33 may be maintained to ensure printing of a clear image.

The rollers 21 are provided at the front and rear of the nozzle 33 at the lower portion of the main body 10, respectively. Herein, the front and rear are based on the direction in which the main body 10 moves along the surface of the target to deliver the printing material to the target. In other words, based on the direction in which the main body 10 is sliding on the surface of the target, the rollers 21 are provided at the front and rear of the nozzle 33.

A portion of the roller 21 in contact with the target may be made of a soft material to smoothly guide the movement of the main body 10 without causing discomfort to the target while closely contacting the surface of the target. In other words, the roller 21 may be made of a soft material, or may be provided in a form in which a soft material is coated on a hard plastic material.

The roller 21 includes a first roller 21A and a second roller 21B. The first roller 21A may be rotatably coupled to the lower portion of the lower body 12. The first roller 21A is provided at the front of the nozzle 33 based on the movement direction of the main body 10, and may space the nozzle 33 from the skin on which the image is printed. For example, the first roller 21A includes at least one first rotation shaft (symbol not shown) provided parallel to the nozzle 33 and at least one first wheel (symbol not shown) provided on the first rotation shaft. Here, the first wheel may be provided to overlap with the nozzle 33 along the movement direction of the main body 10.

On the other hand, when printing an image using the portable printer 1, the user may apply pressure to bring the portable printer 1 into close contact with the skin. In this case, a vertical distance spaced between the skin and the nozzle 33 of the cartridge 31 may be decreased according to the pressure applied by the user.

However, for clear printing of the image, it is preferable that the distance spaced between the skin and the nozzle 33 of the cartridge 31 is maintained at 0.5 mm to 2.5 mm. More preferably, the distance spaced between the skin and the nozzle 33 of the cartridge 31 may be 1.0 mm to 2.0 mm.

When the vertical distance between the skin and the nozzle 33 is less than 0.5 mm or more than 2.5 mm, damage may occur to the image printed using the portable printer 1. In other words, a difference may occur between the image desired by the user and the image printed on the skin.

In particular, when the vertical distance spaced between the skin and the nozzle 33 is less than 0.5 mm, there is a possibility that the nozzle 33 may come into contact with the skin. When the nozzle 33 is in contact with the skin, the rear end of the nozzle 33 and the head 32 may be in contact with the skin. Here, the printing solution discharged from the nozzle 33 may be damaged by the rear end of the nozzle 33 and the head 32.

When the vertical distance spaced between the skin and the nozzle 33 is greater than 2.5 mm, a low-resolution image may be formed on the skin because the distance between the skin and the nozzle 33 is long and the printing solution discharged from the nozzle 33 is dispersed over a wide range.

In addition, in order to maintain a distance of 0.5 mm to 2.5 mm between the skin and the nozzle 33 of the cartridge 31, a height difference H between a lower end of the first roller 21A and the nozzle 33 on a cross-section of the portable printer 1 may range from 4.5 mm to 8.5 mm. Preferably, the height difference H between the lower end of the first roller 21A and the nozzle 33 may range from 5.5 mm to 7.5 mm. If the height difference H between the lower end of the first roller 21A and the nozzle 33 is maintained at 4.5 mm to 8.5 mm, a clear image as shown in FIG. 8 may be printed on the skin.

When the height difference H between the lower end of the first roller 21A and the nozzle 33 is less than 4.5 mm or more than 8.5 mm, damage may occur to the image printed using the portable printer 1. In other words, a difference may occur between the image desired by the user and the image printed on the skin.

In particular, when the height difference H between the lower end of the first roller 21A and the nozzle 33 is less than 4.5 mm, the distance between the skin and the nozzle 33 is close as shown in FIG. 7, and thus damage to the image printed on the skin may occur due to aggregation of the printing material discharged from the nozzle 33. This is because when the height difference H between the lower end of the first roller 21A and the nozzle 33 is less than 4.5 mm, the nozzle 33 or the head 32 is in contact with the skin and the image printed on the skin is damaged when the portable printer 1 is moved.

In addition, when the height difference H between the lower end of the first roller 21A and the nozzle 33 is greater than 8.5 mm, the distance between the skin and the nozzle 33 is large as shown in FIG. 9 and the printing solution discharged from the nozzle 33 is dispersed in a wide range so that a low resolution image may be formed on the skin. In other words, an unclear image may be formed on the skin.

The first roller 21A may guide a printing direction of the portable printer 1. In other words, the first roller 21A may guide the movement of the main body 10.

The first roller 21A may have a shape extended parallel to the nozzle 33. For example, the first roller 21A has a roll shape of a predetermined length and may be provided at the front of the head 32 (the nozzle 33) in the movement direction of the main body 10. Here, the length of the first roller 21A may be the same as the extended length of the nozzle 33 or larger than the extended length of the nozzle 33.

In addition, a separation distance W1 between the first roller 21A and the nozzle 33 on a plane of the portable printer 1 may be a distance enough that the first roller 21A is not contaminated by the printing solution sprayed from the nozzle 33. For example, the separation distance W1 between the first roller 21A and the nozzle 33 may be 6.9 mm to 13.1 mm. Preferably, the separation distance W1 between the first roller 21A and the nozzle 33 may be 8.5 mm to 11.5 mm.

When the separation distance W1 between the first roller 21A and the nozzle 33 is less than 6.9 mm, the first roller 21A may be contaminated by the printing solution sprayed from the nozzle 33. In addition, when the separation distance W1 between the first roller 21A and the nozzle 33 exceeds 13.1 mm, even if the skin is pressed by the first roller 21A, the skin in an area corresponding to the nozzle 33 may be recovered by skin elasticity, and the distance between the nozzle 33 and the skin may be less than 0.5 mm. Therefore, when the separation distance W1 between the first roller 21A and the nozzle 33 is greater than 13.1 mm, the nozzle 33 or the head 32 may be in contact with the skin, and the printed images may be damaged when the portable printer 1 is moved.

The second roller 21B may be rotatably coupled to the lower portion of the lower body 12. The second roller 21B may be provided at the rear of the head 32 (the nozzle 33) based on the movement direction of the main body 10. The second roller 21B may separate the skin on which the image is printed and a lower surface of the lower body 12, and may roll along the skin together with the first roller 21A.

The second roller 21B may be provided in the shape of a wheel to decrease a contact area with the skin. For example, a plurality of the second rollers 21B may include a plurality of second rotation shafts (symbol not shown) provided parallel to the nozzle 33 and a plurality of second wheels (symbol not shown) provided on each of the plurality of second rotation shafts. Here, the plurality of second wheels are provided to be deviated from the nozzle 33 along the movement direction of the main body 10. In other words, the second roller 21B may be spaced apart from a moving line of the nozzle 33.

Two second rollers 21B may be provided, for example. The two second rollers 21B may be spaced apart from each other. For example, the two second rollers 21B may be spaced apart from each other by at least the extended length of the nozzle 33.

Therefore, while the second rollers 21B move along a printing path of the portable printer 1, they may not come into contact with the discharged printing solution. By not contacting the discharged printing solution and the second roller 21B, an image similar to the original image may be printed on the skin without smearing.

In addition, since the second roller 21B does not contact the discharged printing solution, it is possible to prevent the printing solution from being transferred to the skin by the second roller 21B after being migrated to the second roller 21B.

On a plane of the portable printer 1, a distance W2 between the second roller 21B and the nozzle 33 may be substantially the same as the distance W1 between the first roller 21A and the nozzle 33. For example, the separation distance W2 between the second roller 21B and the nozzle 33 on the plane of the portable printer 1 may be 6.9 mm to 13.1 mm. Preferably, the separation distance W2 between the second roller 21B and the nozzle 33 may be 8.5 mm to 11.5 mm.

When the separation distance W2 between the second roller 21B and the nozzle 33 is less than 6.9 mm, the second roller 21B may be contaminated by the printing material sprayed from the nozzle 33. In addition, when the separation distance W2 between the second roller 21B and the nozzle 33 exceeds 13.1 mm, even if the skin is pressed by the second roller 21B, the skin in the area corresponding to the nozzle 33 may be recovered by skin elasticity, and the distance between the nozzle 33 and the skin may be less than 0.5 mm. Therefore, when the separation distance W2 between the second roller 21B and the nozzle 33 exceeds 13.1 mm, the nozzle 33 or the head 32 may be in contact with the skin, and the printed image may be damaged when the portable printer 1 is moved.

Meanwhile, in this embodiment, as an example, the second roller 21B is provided at the rear of the head 32 in the moving direction of the main body 10, and the two second rollers 21B disposed spaced apart from the moving line of the nozzle 33 are provided, but the present disclosure is not limited thereto.

In addition, the first roller 21A and the second roller 21B may have a structure capable of moving up and down. If the first roller 21A and the second roller 21B are capable of moving up and down, even if the portable printer 1 is pressed by the user during use, the distance between the skin and the nozzle 33 may be maintained enough to ensure clear image printing.

The roller 21 such as the first roller 21A may be provided to limit the movement direction of the main body 10 in one direction. In other words, the roller 21 may lead the printing direction of the main body 10 to one side in association with prior guidance of a printing start position by the separation button 13C.

For example, the roller 21 may be structurally provided with a structure capable of rotating only in a forward direction. However, in preparation for the case where the user forcibly rotates the roller 21 in a reverse direction, instead of forcibly restricting the reverse rotation of the roller 21, it may have a structure for guiding by sound or the like so that the user clearly recognizes that the rotation of the roller 21 is in the reverse direction. For example, the roller 21 may roll effortlessly when rotating in the forward direction, while a certain jamming may occur and noise may be generated when rotating in the reverse direction.

In the lower portion of the lower body 12, an optical sensor 22 may be provided. In addition, in the printing direction of the portable printer 1, the optical sensor 22 may be provided to correspond to the center of the nozzle 33 at the rear of the head 32. When the portable printer 1 prints the image on the skin, the optical sensor 22 may check a center line of the moving line of the nozzle 33.

The printer cover 70 is detached to at least one of the main body 10 and the seating part 20 and seals the nozzle 33. The printer cover 70 may be detachably coupled to the lower portion of the lower body 12 to cover the lower portion of the lower body 12. In other words, the printer cover 70 may cover the head 32, the first roller 21A, the second roller 21B, and the optical sensor 22 exposed or protruding from the lower portion of the lower body 12.

Therefore, the printer cover 70 may prevent contamination of the head 32, the first roller 21A, the second roller 21B, and the optical sensor 22, suppress the printing solution from being applied to unnecessary places, and protect the head 32 and the nozzle 33 from external impact.

The following describes operation of the above-described portable printer 1.

First, the user may apply a primer for skin flattening on the skin before printing an image on the skin using the portable printer 1. The above-described primer may flatten the skin to make the image printed on the skin more clear by the portable printer 1. Here, the primer may be a liquid primer or a solid primer.

The liquid primer may include a large amount of volatile solvent, such as ethanol and a film component, for quick drying. However, since ethanol is a volatile solvent in the liquid primer, it may irritate the skin. In addition, the film component is highly irritating to the skin and may cause difficulty in cleansing.

On the other hand, the solid primer may have a significantly lower content of volatile solvent than the liquid primer, resulting in low skin irritation. In addition, the solid primer has a low content of volatile solvent, so the skin may be flattened in a short time. Since the solid primer does not contain the film component, it can be easy to cleanse.

Therefore, it may be preferable to use the solid primer as the primer.

After applying the primer to the skin, the user may print the image on the skin using the portable printer 1.

The user removes the printer cover 70 of the portable printer 1. The user may then switch the portable printer 1 to an On state using the power button 13B.

When the portable printer 1 is turned on, the battery 40 may provide power to each part of the portable printer 1 that requires power so that the portable printer 1 can perform printing operation.

This will be described in detail as follows. When the portable printer 1 is turned on, the user may select an image to be printed on the skin using an external device wired or wirelessly connected to the communication unit 60, for example, a smartphone, a tablet, or a computer.

Here, the image may be any one of images previously stored in the portable printer 1. In addition, the image may be stored in the external device or may be an image obtainable from a site connected to the external device. The image stored in the external device or of the site connected to the external device may be transmitted to the controller 50 of the portable printer 1 through the communication unit 60.

If the image to be printed on the skin is selected by the user, the user may place the portable printer 1 on the skin.

When the portable printer 1 is seated on the skin, the user may start printing of the selected image by manipulating the printing button 13A.

When printing of the selected image starts, the user may move the portable printer 1 at a constant speed to cause the portable printer 1 to print the selected image. Here, the portable printer 1 may move while being guided by the first roller 21A. In addition, while the portable printer 1 is moving, the nozzle 33 for discharging the printing solution onto the skin may be spaced apart from the skin at a predetermined interval by the first roller 21A.

In other words, while the portable printer 1 moves on the skin surface while being carried by the user, the distance between the skin and the nozzle 33 may be maintained at 0.5 mm to 2.5 mm by the first roller 21A so that the image can be clearly printed on the skin.

After the image is printed by the portable printer 1, an adhesive coating to protect the image may be performed. The adhesive coating may be performed using a spray method.

As described above, the portable printer 1 of the present disclosure may print a clear image on the skin because the distance between the skin and the nozzle 33 is maintained at 0.5 mm to 2.5 mm while printing the image.

In addition, if the skin is flattened using the primer before printing the image, a clearer image may be printed on the skin.

Figure 10:
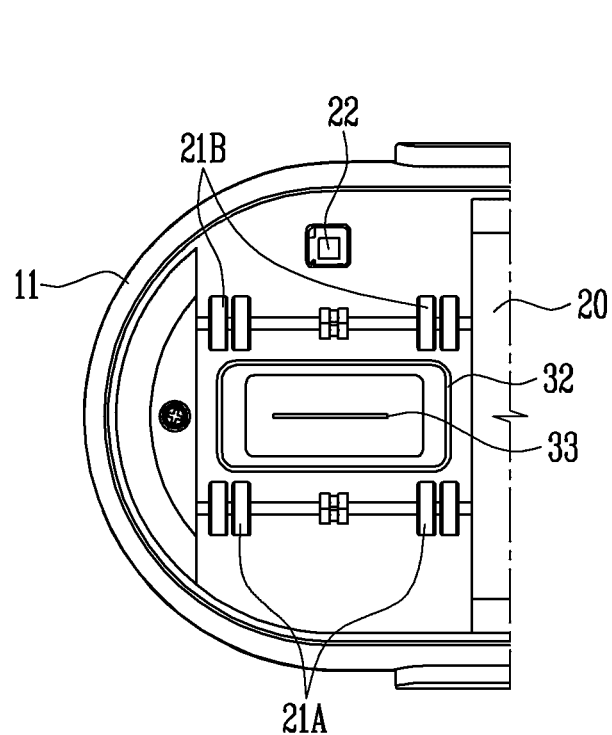
FIG. 10 is a bottom plan view of a portable printer according to a second embodiment of the present disclosure.

FIG. 10 is a bottom plan view of a portable printer according to a second embodiment of the present disclosure.

Hereinafter, the present embodiment will be described mainly in terms of differences compared to other embodiments, and parts omitted from description are replaced by content in other embodiments. This applies to all embodiments herein.

The present disclosure describes by example the shape in which the first roller 21A is provided at the front of the head 32 in the movement direction of the main body 10 and extends parallel to the nozzle 33 in the first embodiment, but is not limited thereto. As shown in FIG. 10, the second embodiment of the present disclosure may be implemented as a structure in which the first roller 21A includes one first rotation shaft (symbol not shown) extending parallel to the nozzle 33, and at least one wheel (symbol not shown) connected to each of both ends of the first rotation shaft.

In addition, unlike in the first embodiment, the second embodiment may be implemented as a structure in which the second roller 21B also includes a second rotation shaft (symbol not shown) extending parallel to the nozzle 33, and at least one second wheel (symbol not shown) connected to each of both ends of the second rotation shaft.

Here, the second rotation shaft of the second roller 21B may overlap with a moving line of the nozzle 33, but the second wheels at both ends of the second rotation shaft may not overlap with the moving line of the nozzle 33.

Figure 11:
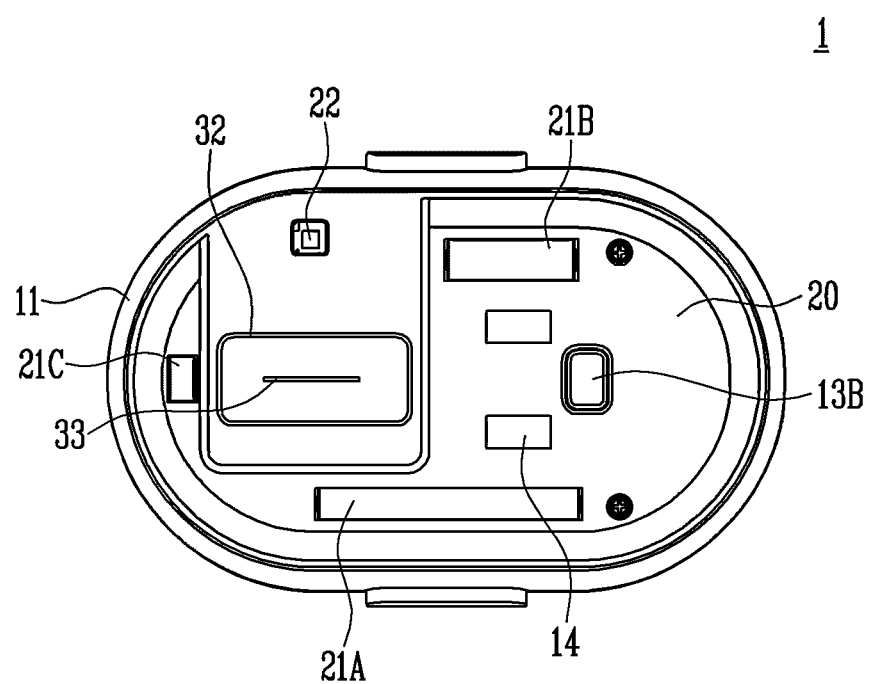
FIG. 11 is a bottom plan view of a portable printer according to a third embodiment of the present disclosure.

FIG. 11 is a bottom plan view of a portable printer according to a third embodiment of the present disclosure.

As shown in FIG. 11, in the third embodiment of the present disclosure, the first roller 21A is provided at the front of the head 32 in a movement direction of the main body 10, while the second roller 21B may be provided at a position that does not overlap with the head 32 in the rear of the head 32 in the moving direction of the main body 10.

In this case, the roller 21 may further include a third roller 21C provided on one side of the head 32 based on the movement direction of the main body 10. In other words, the first to third rollers 21A, 21B, and 21C may be arranged in a substantially triangular shape.

As described above, in the present disclosure, the position of the roller 21 including the first roller 21A and the second roller 21B is not limited to the front or rear of the head 32 along the movement direction of the main body 10. In the present disclosure, in addition to the arrangement of the first roller 21A and the second roller 21B described above, various arrangements of the rollers 21 may be used as long as contamination by the printing solution can be prevented while maintaining an appropriate vertical height between the nozzle 33 and the skin.

FIG. 12 is a side view of a portable printer according to a fourth embodiment of the present disclosure, FIG. 13 is a perspective view of the portable printer according to the fourth embodiment of the present disclosure, and FIG. 14 is a partial cross-sectional view of the portable printer according to the fourth embodiment of the present disclosure.

Figure 12A:
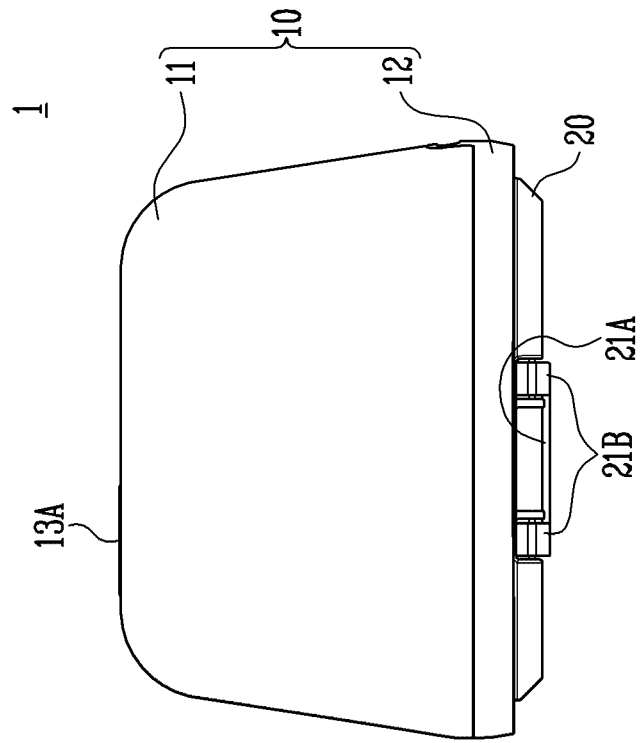
FIG. 12 is a side view of a portable printer according to a fourth embodiment of the present disclosure.
Figure 12B:
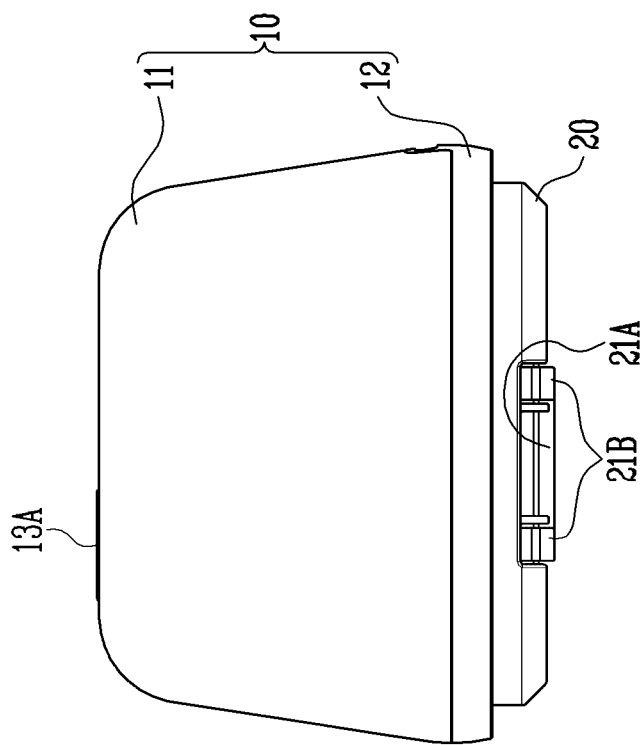
Figure 14A:
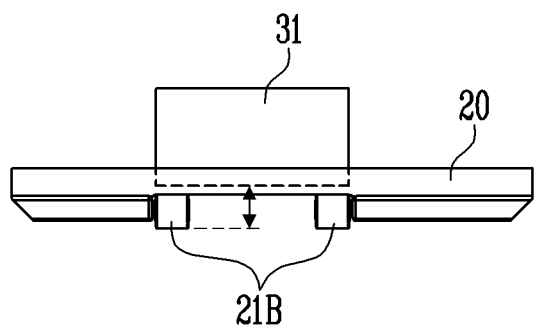
FIG. 14 is a partial cross-sectional view of the portable printer according to the fourth embodiment of the present disclosure.
Figure 14B:
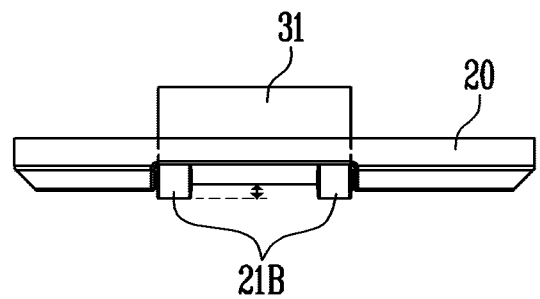

Here, FIG. 12(A), FIG. 13(A), and FIG. 14(A) show a state in which the seating part 20 is placed in a protruding position, and in FIG. 12(B), FIG. 13(B), and FIG. 14(B) show a state in which the seating part is placed in a retracted position.

Previously, in the first embodiment, etc., the case where the distance between the skin and the nozzle 33 is adjusted by moving up and down the cartridge 31 has been described. On the other hand, in the portable printer 1 according to the fourth embodiment of the present disclosure, as the height of the roller 21 or the seating part 20 is changed based on the nozzle 33 of the cartridge 31, the vertical height between the nozzle 33 and the surface of the target may be adjusted.

Specifically, this embodiment includes a printing adjustment unit 100. The printing adjustment unit 100 moves at least the roller 21 among the seating part 20 and the roller 21 in the inner and outer directions of the main body 10. However, since the rotation shaft of the roller 21 may be provided in the seating part 20, the roller 21 may be moved integrally with the seating part 20 by the printing adjustment unit 100.

The printing adjustment unit 100 may move the seating part so that the seating part 20 and the roller 21 are moved in the inner and outer directions of the main body 10. At this time, the movement by the printing adjustment unit 100 may be in any one direction of the inner direction and the outer direction of the main body 10, and the other direction may be manually made by the user.

The printing adjustment unit 100 moves the seating part 20 or the like in the inner and outer directions of the main body 10 to adjust the height difference between the nozzle 33 and the roller 21. This allows the present embodiment to adjust the height difference between the nozzle 33 and the surface of the target.

As mentioned at the outset, the present disclosure may be used in combination with soft skin or hard paper. However, between the first roller 21A and the second roller 21B, the skin is convexly deformed toward the nozzle 33 by skin elasticity, whereas the paper is not.

Considering the characteristic that when a soft target is pressurized by the first roller 21A and the second roller 21B, it is convexly deformed toward the nozzle 33 between the first roller 21A and the second roller 21B, it is possible to adjust a vertical height of the nozzle 33 according to the hardness of the target using the printing adjustment unit 100 according to the present disclosure.

For example, the nozzle 33 may be disposed closer to an inside of the main body 10 compared to the roller 21, and when the printing material is delivered to the soft skin, the printing adjustment unit 100 may move the roller 21 to the protruding position to adjust the height between the nozzle 33 and the roller 21 to 6.0 mm to 7.0 mm.

Alternatively, when the printing adjustment unit 100 delivers the printing material to the hard paper, the roller 21 may be moved to the retracted position to adjust the height between the nozzle 33 and the roller 21 to 0.5 mm to 2.5 mm.

As mentioned above, the printing adjustment unit 100 may have a configuration that assists the movement of the roller 21 by external pressure instead of automatically realizing the movement of the roller 21.

When the nozzle 33 intends to print an image on a soft target such as the skin, the printing adjustment unit 100 may cause the vertical height of the head 32 and the lower end of the roller 21 to preferably be maintained at about 6.5 mm. Through this, an appropriate gap is formed between the nozzle 33 and the skin, preventing the printing material from smearing or clumping.

On the other hand, when the nozzle 33 is a hard object including paper (base paper for nail stickers, etc.), the printing adjustment unit 100 may preferably maintain the vertical height of the head 32 and the lower end of the roller 21 at about 2.0 mm. As an appropriate gap is formed between the nozzle 33 and the paper, clarity of the printing material may be guaranteed.

In other words, in this embodiment, the vertical distance between the nozzle 33 and the surface of the target, precisely the roller 21 pressurizing the target and the nozzle 33 delivering the printing material to the target, is changed according to the hardness of the target. Through this, the present embodiment may sufficiently guarantee the quality of printing even if the hardness of the target is different.

Changing the vertical height of the head 32 and the lower end of the roller 21 as described above is in consideration of the fact that the target may be convexly deformed toward the head 32 between the first roller 21A and the second roller 21B when the target is soft. Since the present disclosure utilizes the printing adjustment unit 100, the vertical height between the surface of the target and the nozzle 33 may be formed to be the same regardless of whether the target is hard or soft.

For reference, both the nozzle 33 and the head 32 are configured at the lower end of the cartridge 31, and the head 32 refers to the periphery of the nozzle 33, and in this specification, the nozzle 33 and the head 32 are disposed at the same vertical height. Therefore, when the vertical height of the head 32 and the roller 21 is changed, the vertical height of the nozzle 33 and the roller 21 is also changed. As mentioned above, the vertical height to the surface of the target relative to the nozzle 33 and the head 32 is adjusted relatively constant as the roller 21 moves according to the hardness of the target.

Hereinafter, a method in which the user uses the printing adjustment unit 100 of the present disclosure to switch to a state where the seating part 20 protrudes downward from the lower body 12 and a state where the seating part 20 protrudes relatively less downward from the lower body 12 is described in detail.

First, when the user selects the skin as the target for printing the image, the user may use it in a state where the seating part and the roller 21 are placed in the protruding position, as shown in FIG. 12(A). In this case, the first roller 21A and the second roller 21B are provided at the front and rear of the head 32, respectively, and the first roller 21A and the second roller 21B maintain the same height difference from the nozzle 33 when the roller 21 is moved in and out by the printing adjustment unit 100.

In FIG. 14(A), the vertical height between the first roller 21A and the nozzle 33 and the vertical height between the second roller 21B and the nozzle 33 may be about 6.5 mm. Therefore, even if the skin has a characteristic of being convexly deformed by skin elasticity, the distance between the nozzle 33 and the skin is spaced at an appropriate level between the first roller 21A and the second roller 21B.

The user adheres the portable printer 1 as shown in FIG. 12(A), etc. to the skin and slides the main body 10 on the skin using the first roller 21A. Here, since the distance between the nozzle 33 and the skin is properly spaced at about 2.0 mm, a clear image may be printed on the skin.

On the other hand, when the user selects a hard object such as paper as the target for printing an image, the user may use it in a state where the seating part 20 and the roller 21 are placed in the retracted position as shown in FIG. 12(B) and the like. In this case, the first roller 21A and the second roller 21B provided at the front and rear of the head 32 maintain the same height difference from the nozzle 33 when the seating part 20 is moved in and out by the printing adjustment unit 100.

In FIG. 14(B), the vertical height between the first roller 21A and the nozzle 33 and the vertical height between the second roller 21B and the nozzle 33 may be about 2.0 mm. Therefore, for paper that does not deform convexly between the first roller 21A and the second roller 21B, the vertical distance from the nozzle 33 is spaced to an appropriate level.

The user adheres the portable printer 1 shown in FIG. 12(B) and the like to the paper, and slides the main body 10 on the paper using the first roller 21A or the like. At this time, since the distance between the nozzle 33 and the paper is appropriately spaced to 2.0 mm or less, a clear image may be printed on the paper.

In this embodiment, the inward and outward movement of the seating part 20 and the roller 21 implemented by the printing adjustment unit 100 may use a rack, a rack gear, or the like. Alternatively, various other means capable of changing and maintaining the vertical height of the seating part 20 to two or more values may be used. Hereinafter, a specific structure that the printing adjustment unit 100 of the present disclosure may have is exemplarily illustrated as another embodiment.

Figure 15:
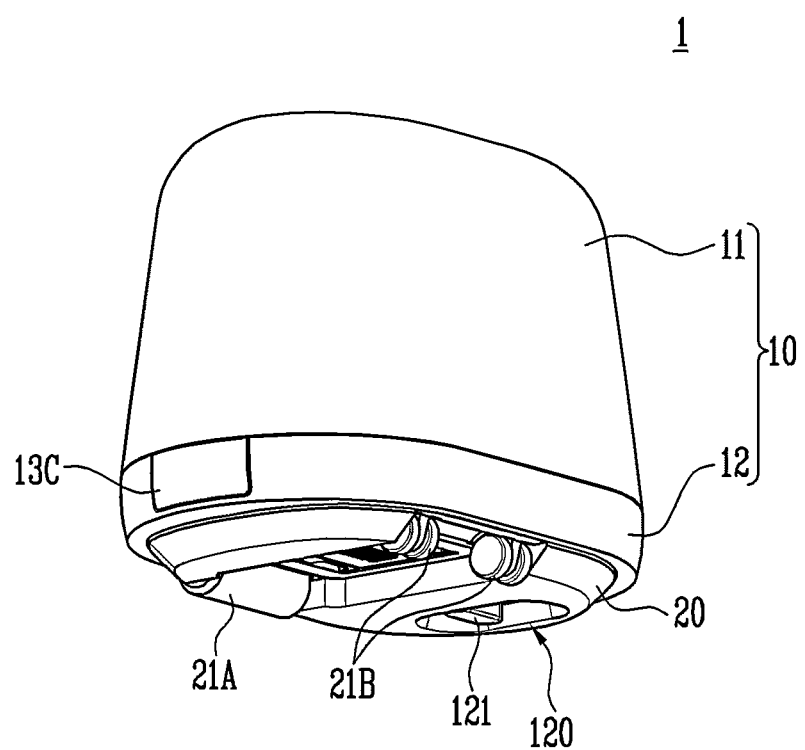
FIG. 15 is a perspective view of a portable printer according to a fifth embodiment of the present disclosure.
Figure 16:
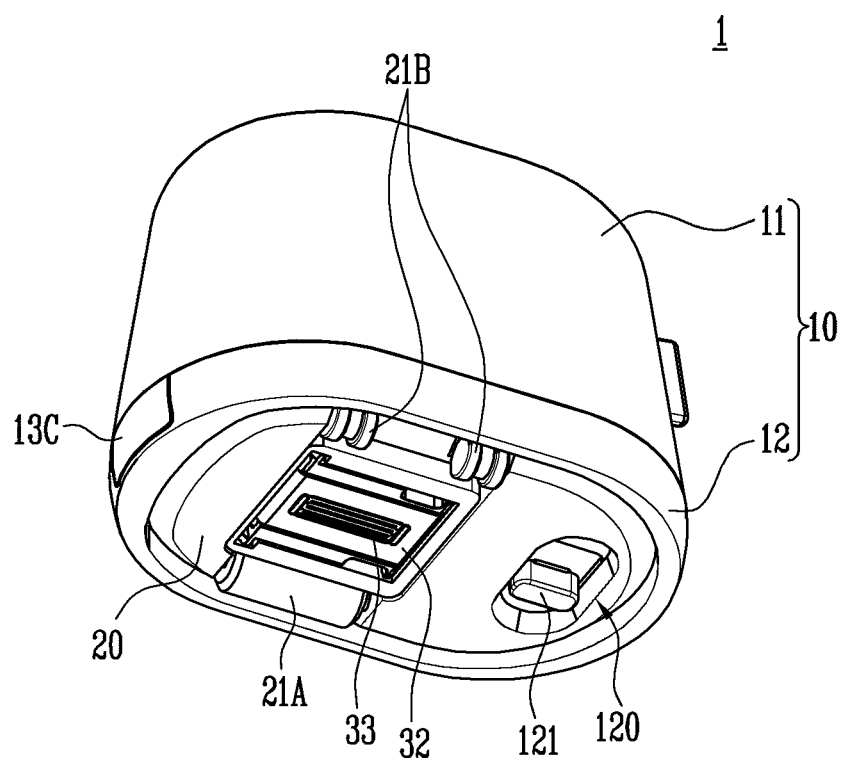
FIG. 16 is a perspective view of the portable printer according to the fifth embodiment of the present disclosure.
Figure 17:
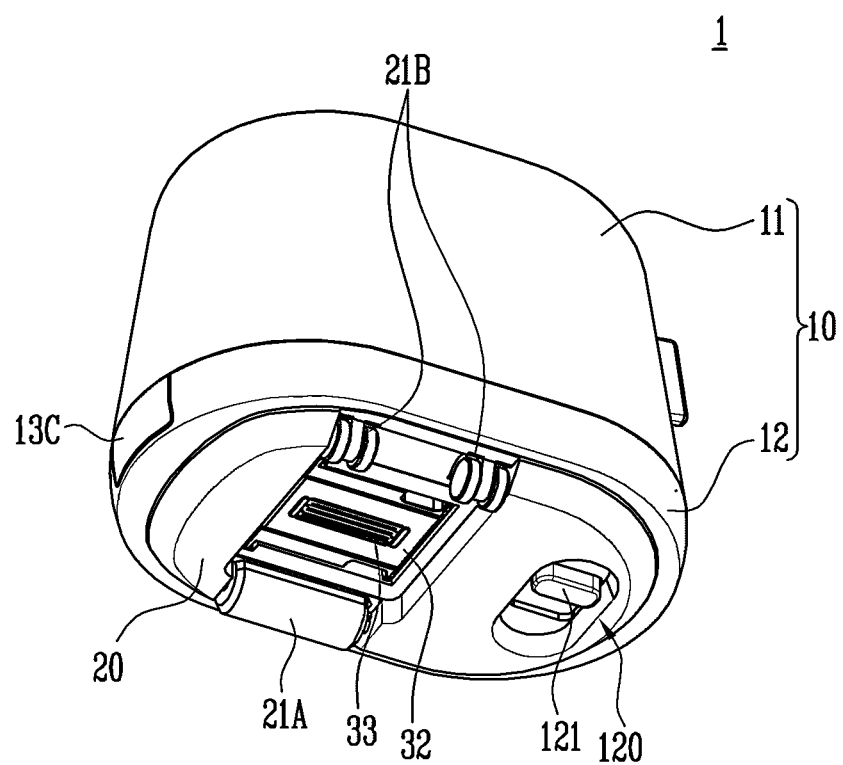
FIG. 17 is a perspective view of the portable printer according to the fifth embodiment of the present disclosure.
Figure 18:
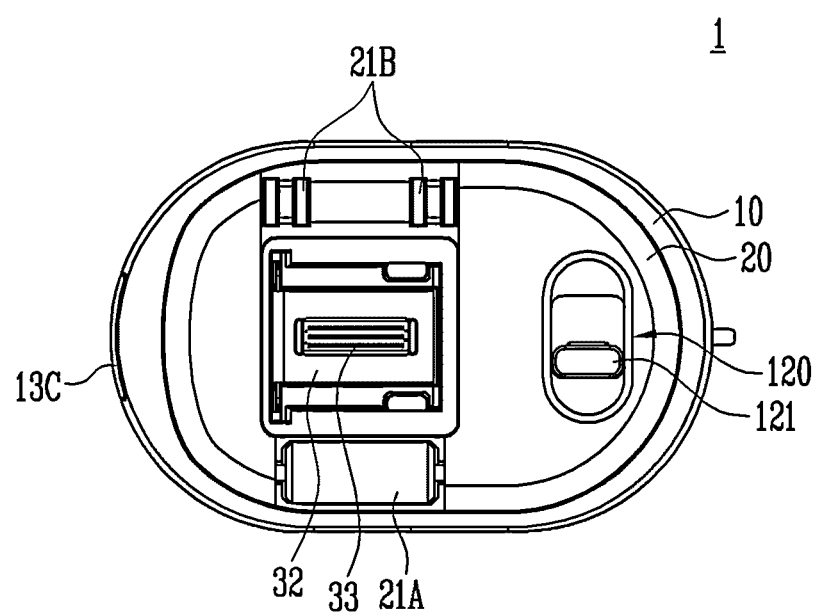
FIG. 18 is a bottom plan view of the portable printer according to the fifth embodiment of the present disclosure.

FIGS. 15 to 17 are perspective views of a portable printer according to a fifth embodiment of the present disclosure, FIG. 18 is a bottom plan view of the portable printer according to the fifth embodiment of the present disclosure, and FIG. 19 is a side view of the portable printer according to the fifth embodiment of the present disclosure.

Figure 20:
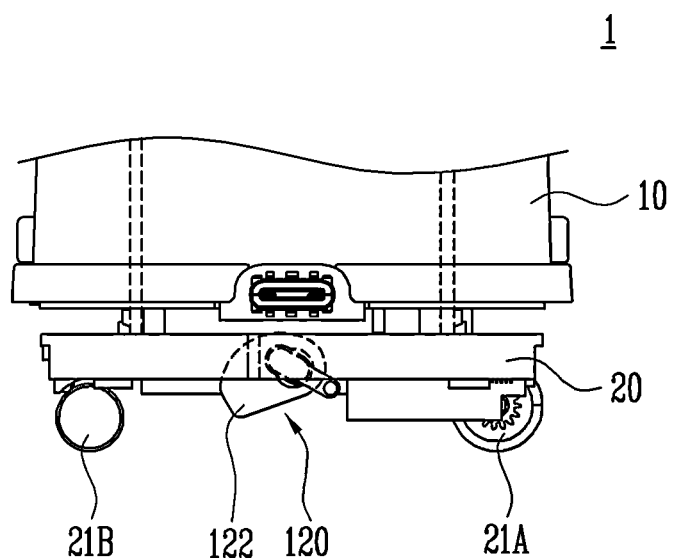
FIG. 20 is a side view of the portable printer according to the fifth embodiment of the present disclosure.
Figures 21A, 21B:
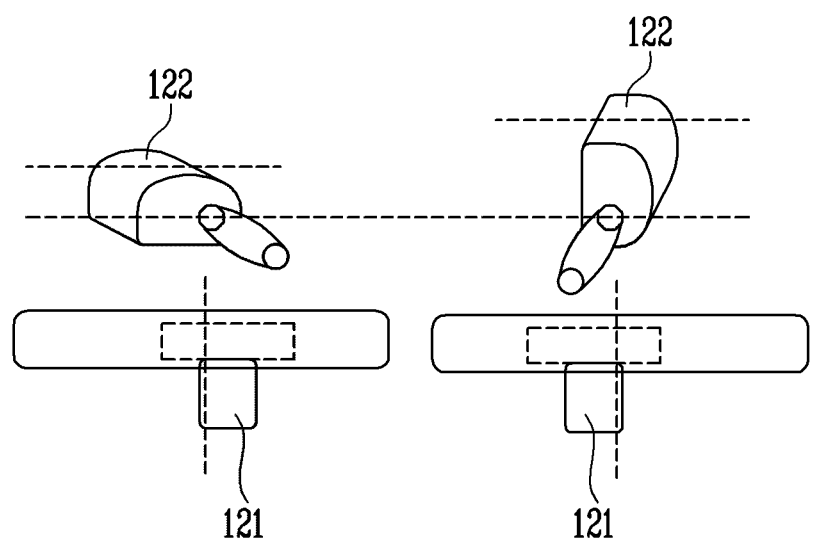
FIG. 21 is a schematic diagram of the portable printer according to the fifth embodiment of the present disclosure.
Figure 22:
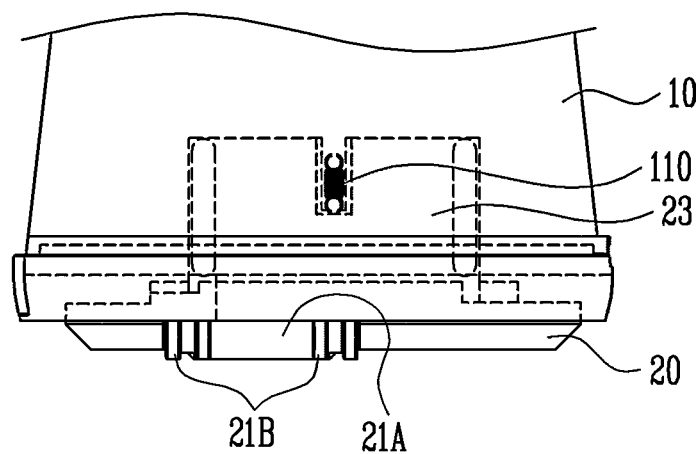
FIG. 22 is a side view of the portable printer according to the fifth embodiment of the present disclosure.

In addition, FIG. 20 is a side view of the portable printer according to the fifth embodiment of the present disclosure that the interior is visible from the outside, FIG. 21 is a schematic diagram of the portable printer according to the fifth embodiment of the present disclosure, and FIG. 22 is a side view of the portable printer according to the fifth embodiment of the present disclosure that the interior is visible from the outside.

Referring to FIGS. 15 to 22, the portable printer 1 according to the fifth embodiment of the present disclosure allows the printing adjustment unit 100 to adjust the height of the seating part 20 (or roller 21) using an elastic member 110 and an operating member 120.

Here, FIGS. 15, 17, 19(A), and 22 show a state in which the seating part 20 is in the protruding position, and FIGS. 16, 19(B), and 20 show a state in which the seating part 20 is in the retracted position.

The elastic member 110 is provided between the main body and the seating part 20, and has an elastic force to maintain the seating part 20 in a restoration position that is either the retracted position or the protruding position with respect to the main body 10.

The seating part 20 may have a wall 23 that is retracted into the inside of the main body 10 and extends to the interior of the upper body 11, and the elastic member 110 may be provided between one point of the wall 23 and a specific point of the main body 10. Therefore, an elastic force is imparted between the main body 10 and the seating part in the height direction.

The elastic member 110 may be a tension spring to maintain the seating part 20 in the retracted position. In other words, the elastic member 110 may be a spring that implements movement in the opposite direction with the elastic force when tensioned. For example, when the seating part 20 protrudes with respect to the main body 10, the elastic member 110 between the main body 10 and the wall 23 is tensioned, so that the seating part 20 is subjected to the elastic force to return to the retracted position in which it is retracted into the main body 10.

In other words, the elastic member 110 may set the retracted position to the restoration position with respect to the seating part 20. Therefore, the printing adjustment unit 100 may retract the seating part 20 using the elastic member 110.

The operating member 120 is provided in the seating part 20 and places the seating part 20 at a change position of one of the retracted position or the protruding position with respect to the main body 10 by external manipulation. When the elastic member 110 sets the retracted position to the restoration position, the operating member 120 may cause the seating part 20 to be placed in the protruding position.

For example, the operating member 120 is deformed to push out the main body 10 from the seating part 20 while tensioning the elastic member 110 by external manipulation, so that the seating part 20 is placed in the protruding position. In other words, the operating member 120 may cause the main body 10 to move up with respect to the seating part 20, or conversely, the seating part 20 may move down with respect to the main body 10.

The operating member 120 may use the operation button 121 exposed to the outside. The operation button 121 may be provided on the seating part 20 and may be disposed to be exposed on the surface of the seating part 20. In addition, the operation button 121 is surrounded by the seating part 20 and is provided so that it does not protrude from the seating part 20 so as not to interfere with printing.

The operation button 121 is provided to be movable in a horizontal direction. In other words, the operation button 121 may be provided so that it does not protrude downward from the seating part 20 regardless of whether it is manipulated or not. The operation button 121 is placed in a first position when the seating part 20 is restored to the retracted position by the elastic member 110, and when it moves to a second position in the horizontal direction, a force for lifting the main body 10 with respect to the seating part 20 may be induced.

The operating member 120 includes a cam 122 connected to the operation button 121. The cam 122 is provided between the seating part 20 and the main body 10, and one end of the cam 122 is rotatably provided by the operation button 121. In other words, the cam 122 is provided in a form of rotating with respect to a rotation shaft (symbol not shown), but one end and the other end may be asymmetrically provided.

When one end of the cam 122 is rotated by the operation button 121, a height of the other end facing the main body 10 may be variable. In other words, when the operation button 121 moves from the first position to the second position, the cam 122 may rotate in a predetermined direction and the height of the other end may increase. The other end of the cam 122 may be provided to come into contact with a predetermined point inside the main body 10, and when the height of the other end of the cam 122 increases, the main body 10 moves up with respect to the seating part 20.

At this time, the elastic member 110 is tensioned while a force greater than the elastic force is applied, and the seating part 20 is placed in a protruding position with respect to the main body 10. In particular, a portion of the cam 122 that pushes up the main body 10 has a planar shape as shown in FIG. 21(B), and therefore, in the state of FIG. 21(B), despite the elastic force of the elastic member 110, the seating part 20 may be maintained in the protruding position.

Hereinafter, a method of using the printing adjustment unit 100 will be described.

First, in this embodiment, when the operating member 120 is in the first position and the seating part 20 is in the retracted position in which it is retracted into the main body 10 by the elastic member 110, the portable printer 1 has the form shown in FIG. 16 and the like. Here, the height of the nozzle 33 compared to the first roller 21A or the second roller 21B is about 2.0 mm.

The user may slide the portable printer 1 in this state against the paper so that the image is printed at an appropriate resolution on the paper or the like. At this time, the seating part 20 may be structurally engaged within the main body 10 so that additional retraction may be restricted, and despite the weight of the seating part 20, protrusion of the seating part 20 is also limited due to the elastic member 110. Therefore, the interval between the roller 21 and the nozzle 33 provided in the seating part 20 may be kept constant.

On the other hand, when the user wants to print on a soft target such as the skin instead of the paper, the user moves the operation button 121 by pushing it in the horizontal direction.

At this time, as the cam 122 associated with the operation button 121 rotates, the other end of the cam 122 pushes up the main body 10 to fix it, and the elastic member 110 provided between the main body 10 and the seating part 20 is tensioned.

The user may slide the portable printer 1 in the state shown in FIG. 17 against the skin so that the image is printed at an appropriate resolution on the skin. At this time, since the flat portion of the other end of the cam 122 comes into contact with the inside of the main body 10, the seating part 20 is restricted from moving inside the main body 10. In addition, further protrusion of the seating part 20 may be strictly limited by the elastic force of the tensioned elastic member 110. Therefore, the gap between the roller 21 and the nozzle 33 provided in the seating part 20 is maintained at about 6.5 mm.

When the user wants to switch the portable printer 1 in the state shown in FIG. 17 and the like to the state of FIG. 16 and the like, the user moves the operation button 121 from the second position to the first position. At this time, when the flat portion of the other end of the cam 122 deviates from the portion that comes into contact with the inside of the main body 10, the seating part 20 and the roller 21 automatically move to the inner side of the main body 10 by the elastic force of the elastic member 110.

In other words, when the operation button 121 needs to move from the first position to the second position to move the seating part 20 from the retracted position to the protruding position, an external force equal to or greater than the elastic force of the elastic member 110 is required. On the other hand, when the operation button 121 needs to move horizontally from the second position to the original position in order to move the seating part 20 from the protruding position to the retracted position, the elastic force of the elastic member 110 may be used auxiliaryly and thus less external force may be required compared to the case of protruding the seating part 20.

Therefore, in the present embodiment, since the seating part may mainly maintain the state of being retracted into the main body 10, the seating part 20 or the roller 21 may be protected from external impact or foreign matter.

Figure 23:
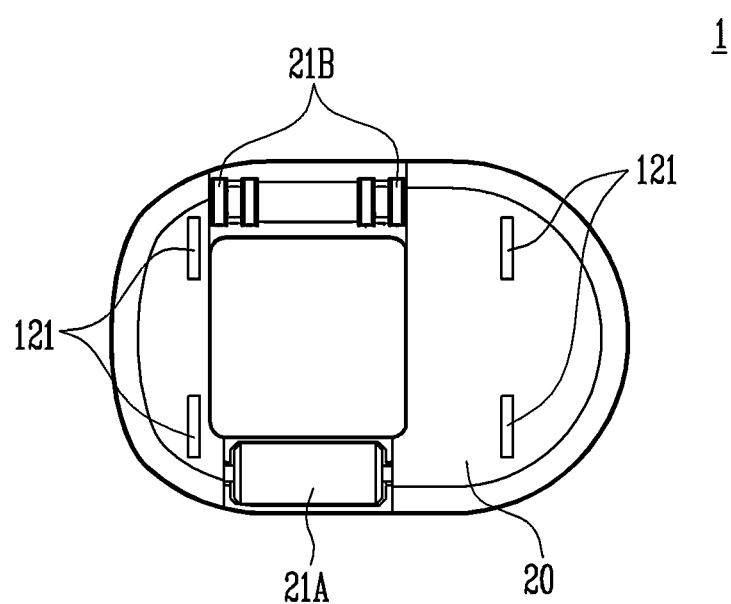
FIG. 23 is a bottom plan view of a portable printer according to a sixth embodiment of the present disclosure.
Figure 24:
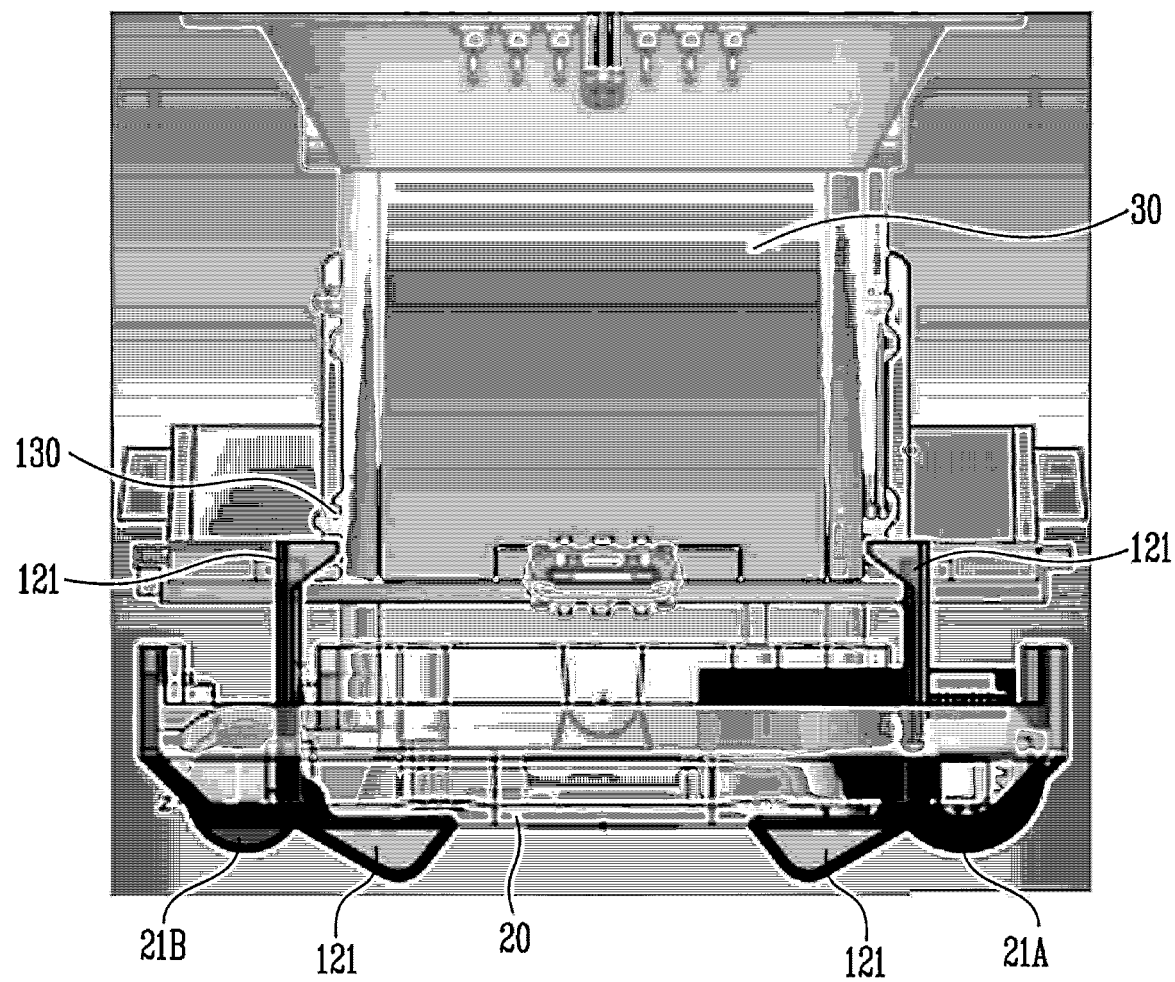
FIG. 24 is a side view of the portable printer according to the sixth embodiment of the present disclosure.
Figure 25:
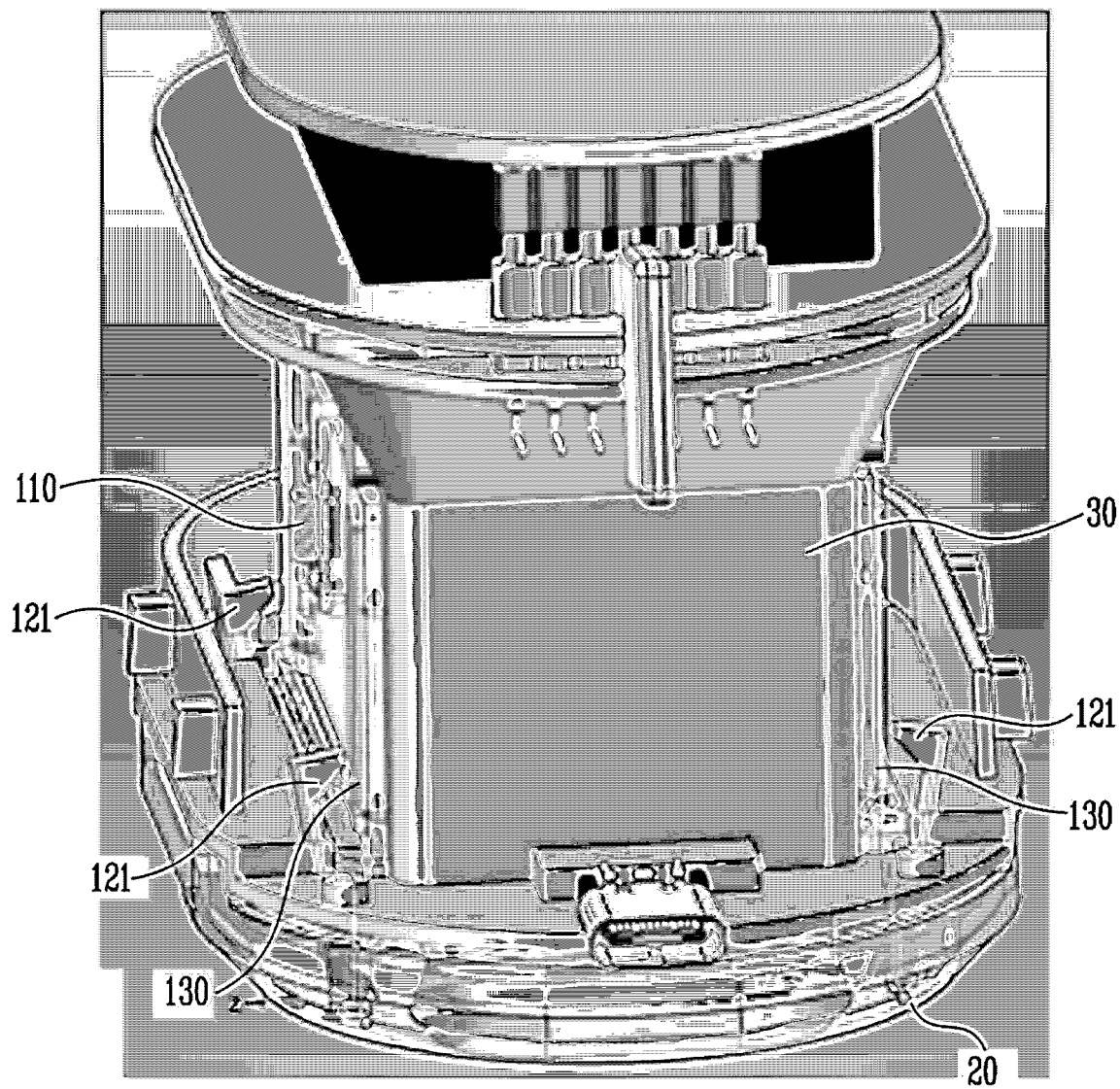
FIG. 25 is an exploded perspective view of the portable printer according to the sixth embodiment of the present disclosure.

FIG. 23 is a bottom plan view of a portable printer according to a sixth embodiment of the present disclosure, FIG. 24 is a side view of the portable printer according to the sixth embodiment of the present disclosure that the interior is visible from the outside, and FIG. 25 is an exploded perspective view of the portable printer according to the sixth embodiment of the present disclosure.

Figure 26:
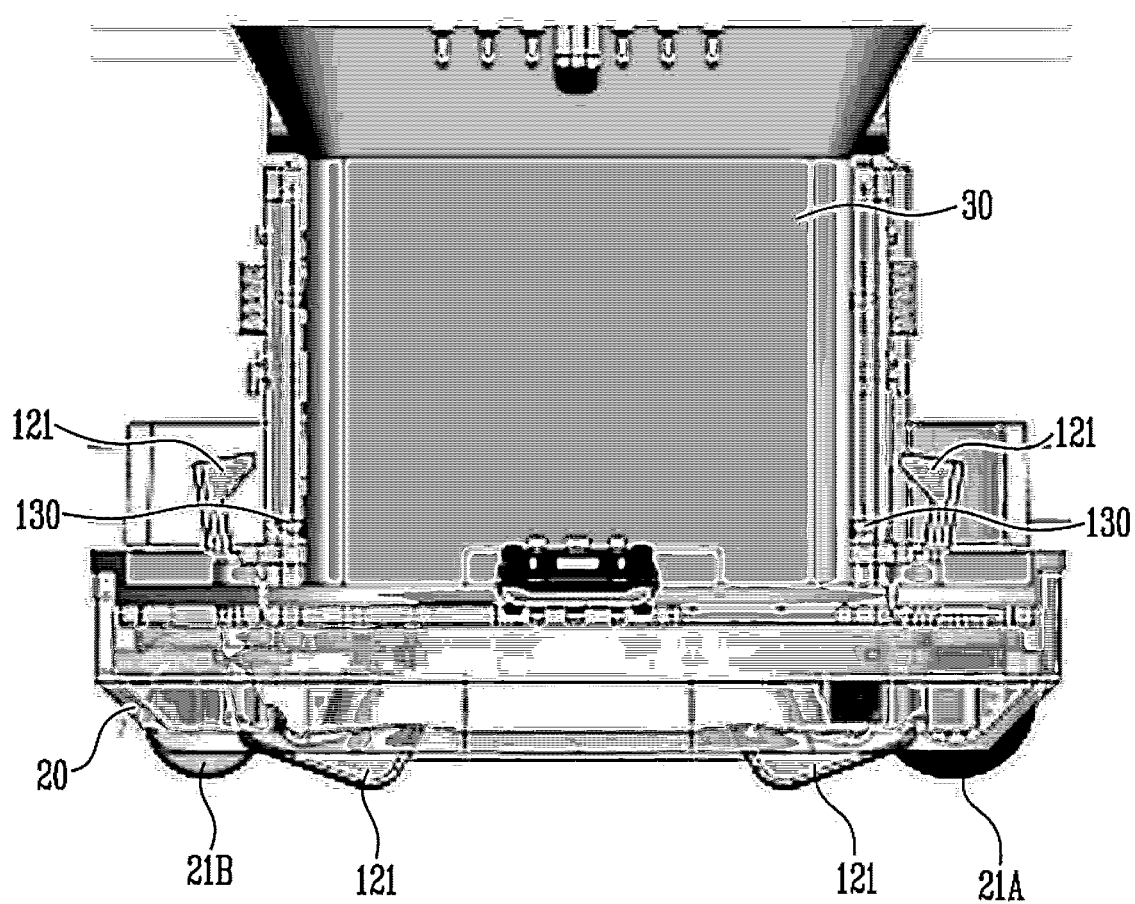
FIG. 26 is a side view of the portable printer according to the sixth embodiment of the present disclosure.
Figure 27:
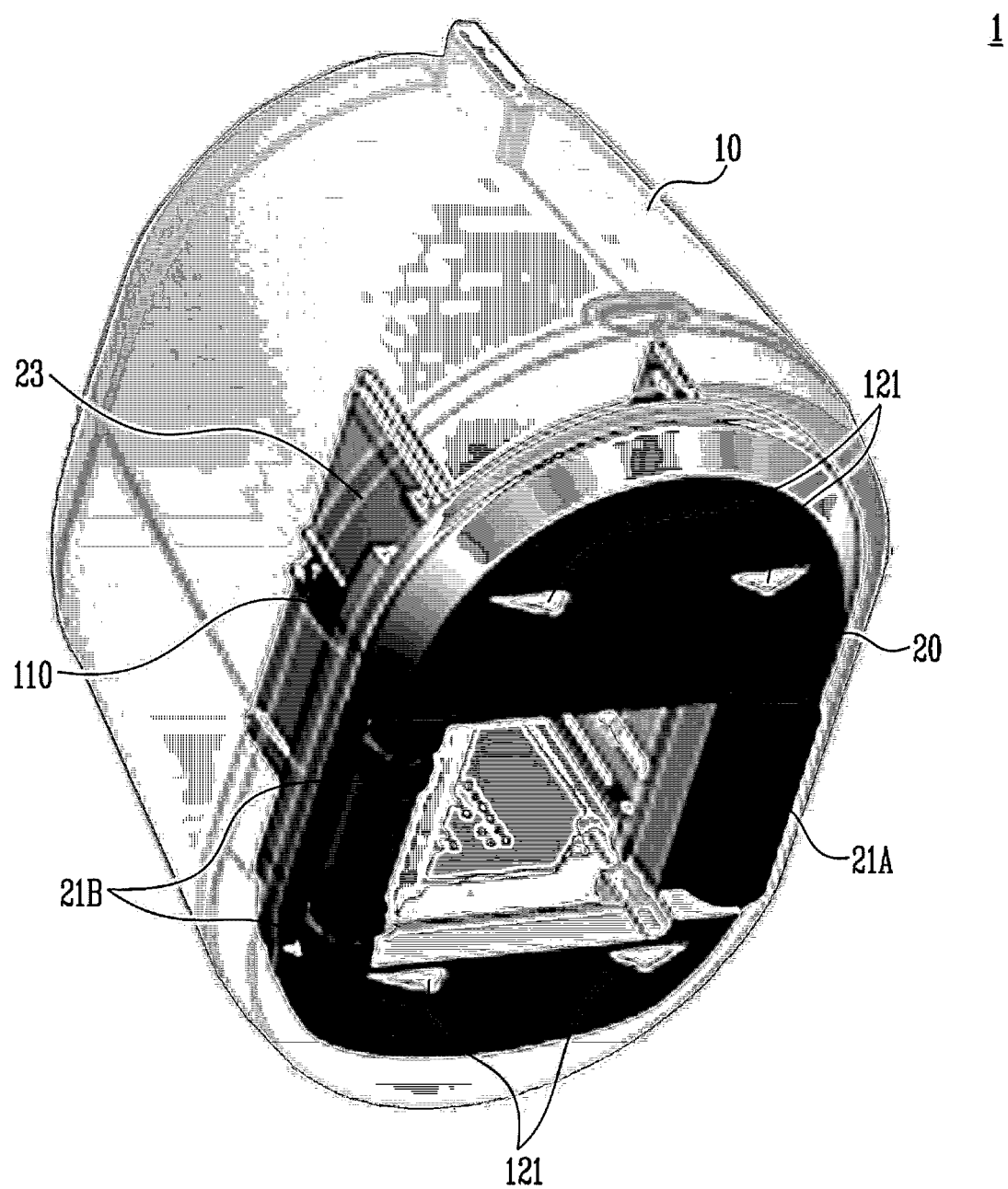
FIG. 27 is a perspective view of the portable printer according to the sixth embodiment of the present disclosure.
Figure 28:
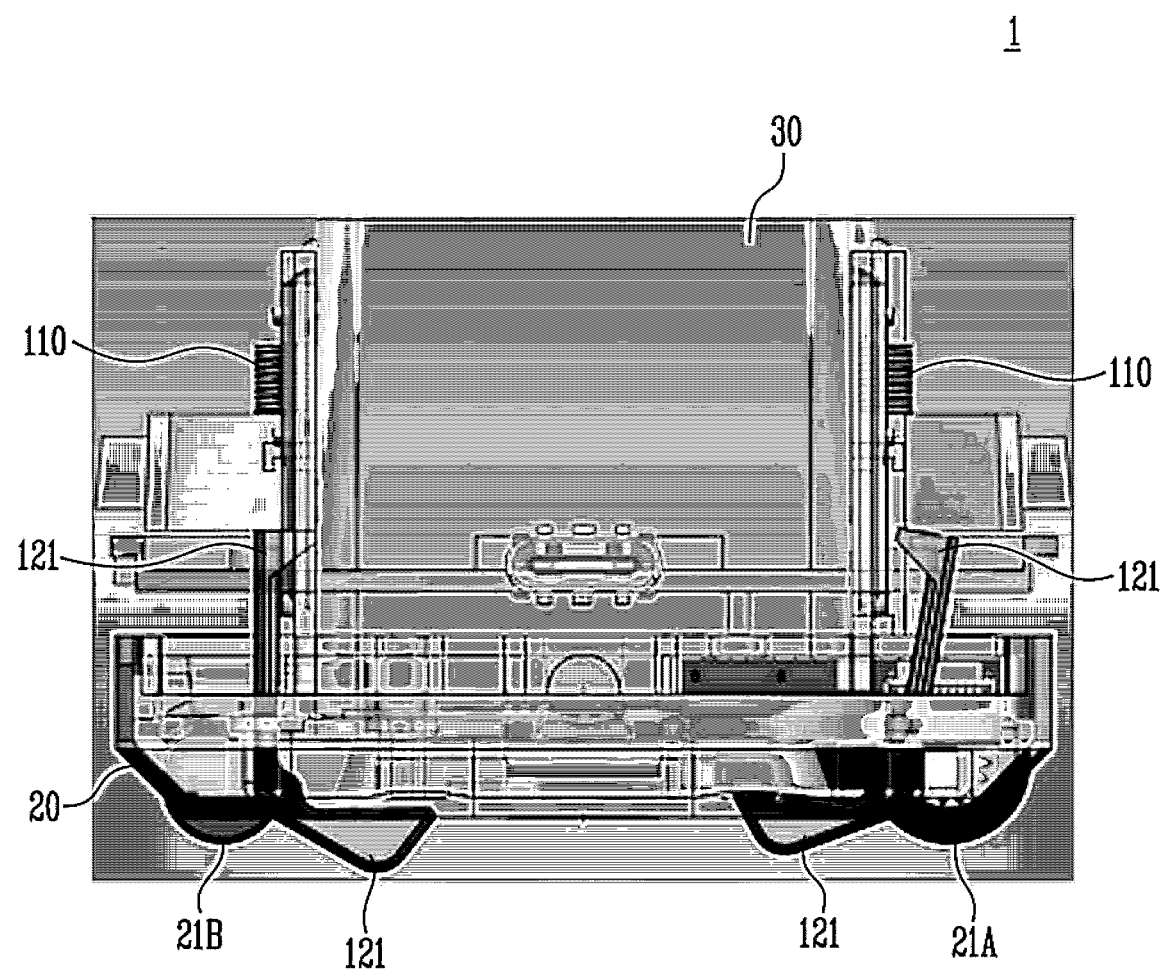
FIG. 28 is a side view of the portable printer according to the sixth embodiment of the present disclosure.

In addition, FIG. 26 is a side view of the portable printer according to the sixth embodiment of the present disclosure that the interior is visible from the outside, and FIG. 27 is a perspective view of the portable printer according to the sixth embodiment of the present disclosure, and FIG. 28 is a side view of the portable printer according to the sixth embodiment of the present disclosure that the interior is visible from the outside.

For reference, FIGS. 24, 27, and 28 show a state in which the cartridge 31 is retracted, and FIGS. 25 and 26 show a state in which the cartridge 31 protrudes.

Referring to FIGS. 23 to 28, the portable printer 1 according to the sixth embodiment of the present disclosure is common in that it includes the printing adjustment unit 100 compared with the fifth embodiment, but the configuration of the printing adjustment unit 100 varies between the embodiments.

The foregoing embodiment is provided to move the seating part 20 in the inner and outer directions with respect to the main body 10, and the present embodiment is also provided to move the seating part 20 in the inner and outer directions with respect to the main body 10.

In addition, the fifth embodiment is provided to maintain a state in which the seating part 20 is retracted through the elastic member 110, which is a tension spring provided in the printing adjustment unit 100, and in this embodiment as well, the retracted position of the seating part 20 may be set to the restoration position through the elastic member 110, which is a tension spring included in the printing adjustment unit 100.

However, in the fifth embodiment above, the seating part 20 protrudes while the operating member 120 tensions the elastic member 110, while in the present embodiment, the operating member 120 may fix a state in which the elastic member 110 is tensioned to maintain the protruding position of the seating part 20.

In other words, in the fifth embodiment, when the seating part 20 is changed from the retracted position to the protruding position, external manipulation by the operating member 120 and forced tension of the elastic member 110 are made. In the present embodiment, when the seating part 20 changes from the retracted position to the protruding position, forced tension of the elastic member 110 is made.

On the other hand, in the fifth embodiment, when the seating part 20 is changed from the protruding position to the retracted position, the manipulation of the operating member 120 and the elastic contraction of the elastic member 110 are made. In the present embodiment, when the seating part 20 is changed from the protruding position to the retracted position, disengagement of the operating member 120 and elastic contraction of the elastic member 110 are made.

Specifically, the printing adjustment unit 100 of the present embodiment includes the elastic member 110 for maintaining the seating part 20 in the retracted position, and the operating member 120 configured to engage with or disengage from the main body 10. The elastic member 110 may be a tension spring that maintains the seating part 20 in the retracted position in the same/similar manner to that described in the fifth embodiment, wherein the tension spring may be provided between the main body 10 and the seating part 20. Alternatively, the tension spring may be provided between the cartridge 31 and the seating part 20.

The operating member 120 is provided to engage with or disengage from a locking protrusion 130 of the main body 10. The seating part 20 may include the wall 23 extending inside the main body 10, and the locking protrusion 130 may be provided in a portion adjacent to the wall 23 in the main body 10. At this time, since the locking protrusion 130 has a triangular cross-section, upward movement with respect to the operating member 120 is easy, while downward movement may be restricted.

Of course, as will be described below, the operating member 120 may also have an inverted triangular cross-sectional form, through which the operating member 120 is restricted from moving upward with respect to the locking protrusion 130, while the movement of the locking protrusion 130 downward may be allowed.

The operating member 120 may be engaged with the locking protrusion 130 of the main body 10 to maintain the seating part 20 in the protruding position. When the seating part 20 protrudes with respect to the main body 10 through external manipulation or operation by an internal configuration, an upper end of the operating member 120 is disposed below a lower end of the locking protrusion 130. In this case, a lower surface of the locking protrusion 130 and an upper surface of the operating member 120 may come into contact with each other.

When the seating part 20 is placed in the protruding position, the elastic member 110 has a force to restore elasticity as a tensioned state. However, as the operating member 120 and the locking protrusion 130 come into contact with each other, the seating part 20 is restricted from moving inside the main body 10.

Therefore, in the present embodiment, the operating member 120 may be engaged with the locking protrusion 130 of the main body 10 while the seating part 20 protrudes, so that the seating part 20 is maintained in the protruding position. Through this, since the height between the head 32 and the roller 21 increases in the present embodiment, damage to the skin due to misuse may be prevented.

On the other hand, when the operating member 120 is disengaged from the locking protrusion 130 of the main body 10 by external manipulation, an elastic restoration force of the elastic member 110 acts on the seating part 20. In this case, the seating part 20 may move inward with respect to the main body 10 and be placed in the retracted position. The seating part 20 disposed in the retracted position may be maintained in the retracted position through the elastic force of the tension spring, which is the elastic member 110.

In other words, the locking protrusion 130 may be engaged with the operating member 120 when the seating part 20 protrudes. A first state in which the operating member 120 is engage with the locking protrusion 130 of the main body 10 may be a state in which the elastic member 110 is tensioned.

On the other hand, the operating member 120 may be switched to a second state in which it is disengaged from the locking protrusion 130 of the main body 10 by external manipulation. When the operating member 120 is disengaged from the main body 10 by external manipulation, the seating part 20 may be moved by the elastic member 110 and placed in the retracted position.

In other words, the elastic member 110 will try to change the seating part 20 to the retracted position, and the operating member 120 may be engaged with the locking protrusion 130 of the main body 10 to hinder the retraction of the seating part 20 or may permit the retraction of the seating part 20 while being deviated from the locking protrusion 130.

Specifically, the operating member 120 includes the operation button having one end exposed to the outside and the other end in contact with the locking protrusion 130. The operation button 121 may restrict retracting movement of the seating part 20 by the elastic member 110 when the other end is engaged with the locking protrusion 130.

On the other hand, one end of the operation button 121 may be exposed to a lower portion of the seating part 20, and the other end may be rotated when the exposed end is pressed. In other words, the operation button 121 may have a rotating bar shape.

The other end of the operation button 121 may rotate in a direction away from the locking protrusion 130 within the main body 10, through which the operation button 121 may be deviated from the locking protrusion 130 to allow movement of the seating part 20 by the elastic member 110.

In other words, the operation button 121 and the locking protrusion 130 are configured for fixing the state in which the seating part protrudes while the elastic member 110 is tensioned, and when the operation button 121 is disengaged from the locking protrusion 130, the seating part 20 is automatically retracted in by the elastic member 110.

The retraction of the seating part 20 means that the vertical height between the roller 21 and the nozzle 33 provided in the seating part 20 is decreased. This indicates that the portable printer 1 is switched to a state suitable for printing on the paper or the like, and may be a state in which it is inappropriate for printing on the skin.

On the other hand, the protrusion of the seating part 20 may increase the vertical height between the nozzle 33 and the roller 21 on the seating part 20 which is suitable for printing an image on the skin. Therefore, in order to prevent misuse on the skin, the seating part 20 may be fixed in the protruding position suitable for skin printing using the operating member 120.

In addition, in the present embodiment, a plurality of the operation buttons 121 of are provided. At this time, one end of each of the plurality of operation buttons 121 protrudes at a uniform height on one surface facing the surface of the target from the seating part 20.

Since each of the operation buttons 121 may be provided so as to be engaged with the locking protrusion 130 provided on the main body 10, only when all the operation buttons 121 are disengaged from the locking protrusions 130, the seating part 20 may be retracted and moved smoothly.

As shown in FIG. 28, when some of the operation buttons 121 are engaged with the locking protrusions 130 and only the rest are disengaged from the locking protrusions 130, the seating part 20 may not move to the retracted position with respect to the main body 10.

In other words, the retracting movement of the seating part is possible only when one end of each of all the operation buttons 121 is pressed at once. The operation button 121 may be manipulated by directly pressing the surface of the target instead of being manipulated by the user's finger or the like. To this end, the plurality of operation buttons 121 are provided so that one end thereof protrudes relatively more than the roller 21 from the seating part 20.

However, when the target is the skin, even if the operation button 121 protrudes downward relative to the roller 21, the operation button 121 may not be pressed by the skin. In other words, the portable printer 1 of the present embodiment may fix the vertical height between the seating part 20 and the head 32 to be suitable for the skin, and the seating part 20 may not be retracted even if the roller 21 slides in close contact with the skin.

On the other hand, when the target is the paper, the operation button 121 may protrude downward relative to the roller 21 and the operation button 121 may be pressed by the hard paper. Therefore, the portable printer 1 of the present embodiment may maintain a state suitable for printing on the skin, and then allow the seating part 20 to be retracted by bringing the seating part 20 against the paper and pressing the operation button 121 by the paper. This allows the user to deform the portable printer 1 so that the vertical height between the roller 21 and the nozzle 33 is decreased.

Hereinafter, in the present embodiment, a method in which the user switches the target on which printing is performed is described.

In this embodiment, the seating part 20 having the roller 21 receives a force to be retracted into the main body 10 by the elastic member 110. However, when the seating part 20 is in the protruding position, the operation button 121 is engaged with the locking protrusion 130, and the seating part 20 maintains the protruding position.

In particular, the operation button 121 may have a shape of returning to a state in which the other end is engaged with the locking protrusion 130 using a spring or the like. In addition, as described above, the operation button 121 is provided in the shape of an inverted triangle with an inclined lower side and a flat upper side. Accordingly, the protrusion 130 may pass from the lower side to the upper side of the operation button 121, but may not pass from the upper side to the lower side.

In view of this, in the portable printer 1 of the present embodiment, when the seating part 20 protrudes due to an external force or the like in a state where the other end of the operation button 121 is located higher than the locking protrusion 130 (the retracted position of the seating part 20), the other end of the operation button 121 may be opened away from the protrusion 130.

Thereafter, when the seating part 20 protrudes above a certain level and the other end of the operation button 121 goes beyond the locking protrusion 130, the flat upper side of the other end of the operation button 121 faces a flat lower side of the locking protrusion 130. Therefore, since the operation button 121 is suppressed from moving up with respect to the protrusion 130, the seating part 20 remains in a protruding state.

In other words, when the seating part 20 protrudes, the elastic member 110 is tensioned, and as the other end of the operation button 121 is opened laterally away from the locking protrusion 130 by the locking protrusion 130, the locking protrusion 130 goes over the other end of the operation button 121.

Thereafter, the other end of the operation button 121 is switched to a state where it is engaged with the locking protrusion 130 by its own elastic force, and the operation button 121 and the locking protrusion 130 are engaged.

Therefore, despite the elastic force by which the elastic member 110 is compressed, the seating part 20 may stably maintain the protruding position as shown in FIG. 24.

For reference, the seating part 20 may be changed from the retracted position to the protruding position by the user directly grasping and pulling, or as an engagement structure with the seating part 20 is applied to the printer cover 70, it is possible to move the seating part 20 to the protruding position using the printer cover 70. In other words, in this embodiment, the method of moving the seating part 20 to the protruding position is not limited.

On the other hand, when the user wants to print on the hard target such as paper, the user may simultaneously press the other end of each of the plurality of operation buttons 121 to release all engagements between the operation buttons 121 and the locking protrusions 130. In this case, by the elastic restoration force of the elastic member 110, the seating part 20 is retracted toward the main body 10 and is in the state shown in FIG. 26.

Alternatively, the user may close the seating part 20 to the target such as the paper and allow the operation button 121 to be pressed directly by the surface of the target. At this time, since the seating part 20 is changed from the protruding position to the retracted position only when all of the operation buttons 121 are pressed, the present embodiment may allow the user to induce a state in which the head 32 and the surface of the target are horizontal.

Figure 29:
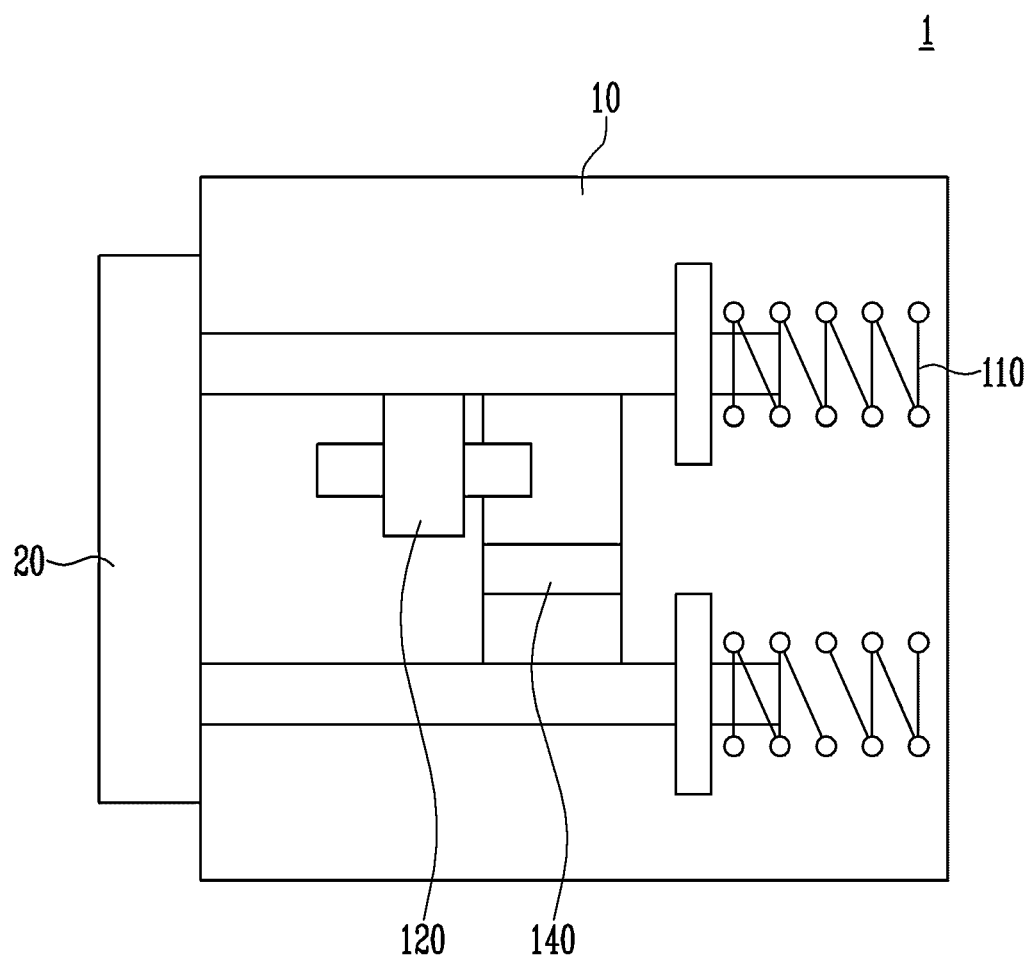
FIG. 29 is a cross-sectional view of a portable printer according to a seventh embodiment of the present disclosure.
Figure 30:
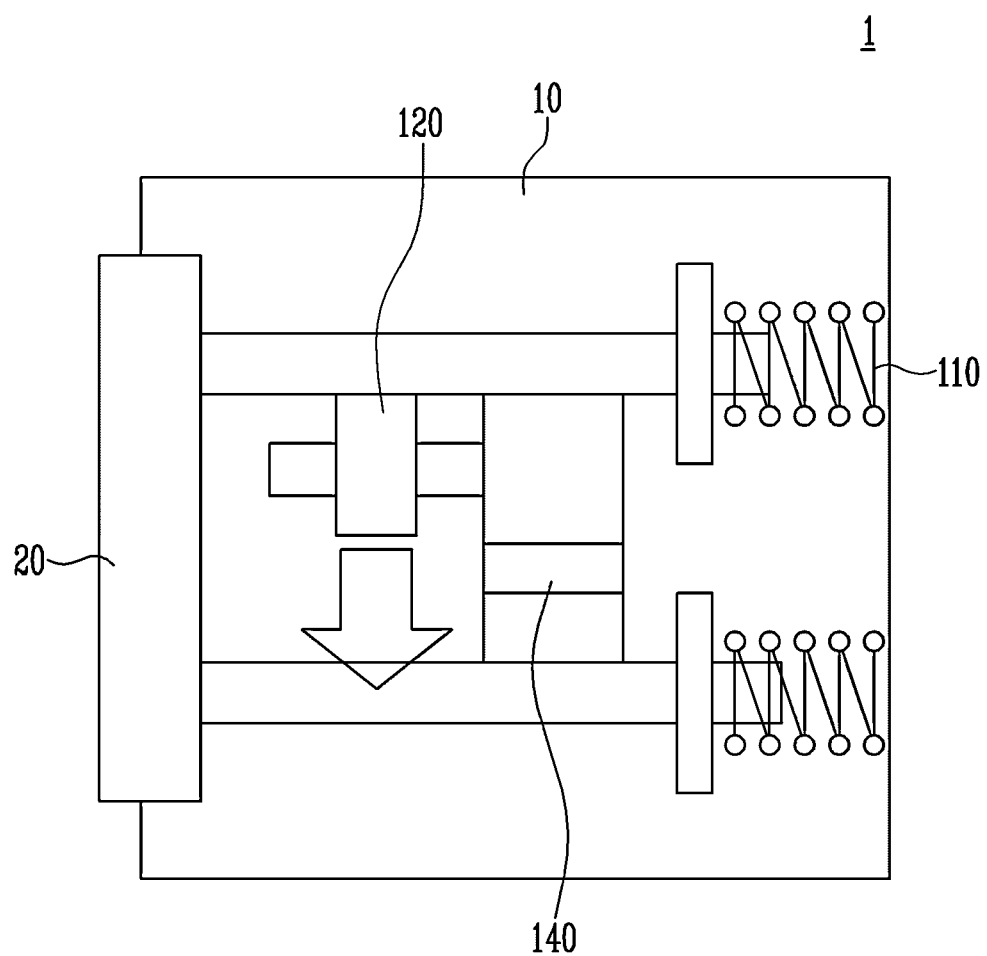
FIG. 30 is a cross-sectional view of the portable printer according to the seventh embodiment of the present disclosure.
Figure 31:
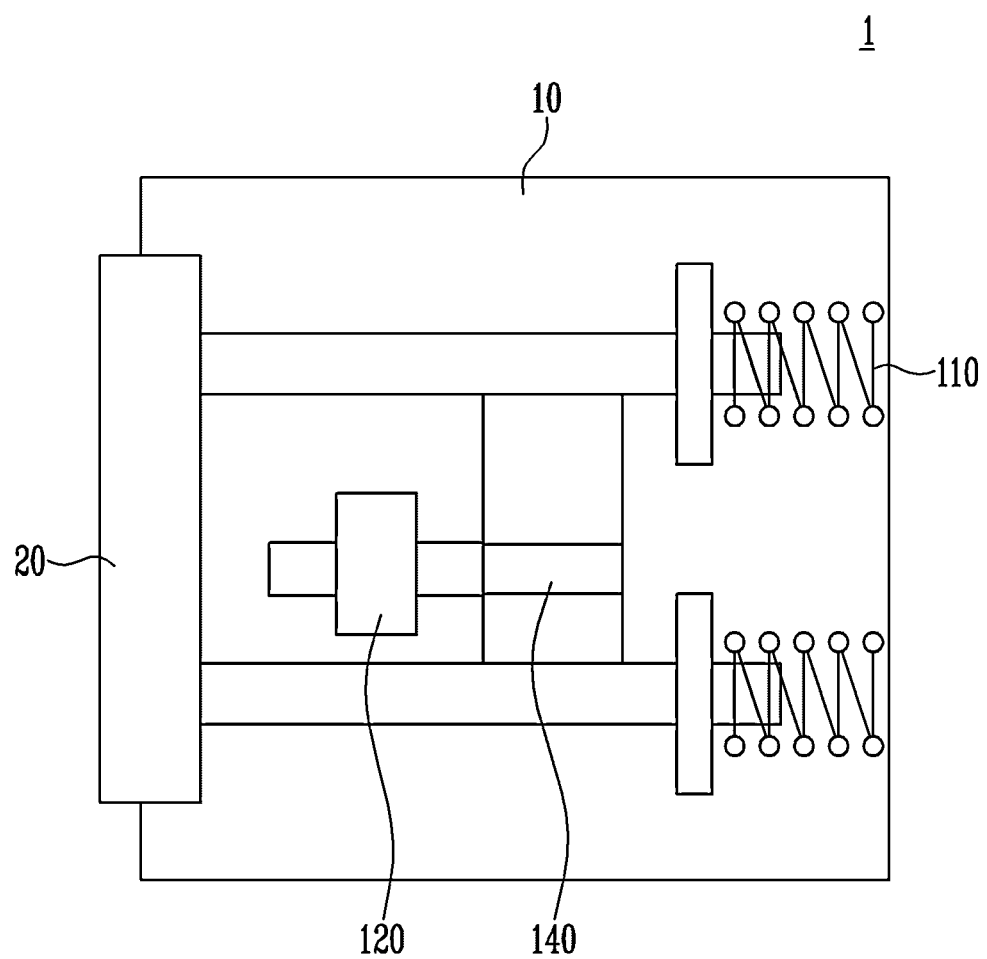
FIG. 31 is a cross-sectional view of the portable printer according to the seventh embodiment of the present disclosure.

FIGS. 29 to 31 are cross-sectional views of a portable printer according to a seventh embodiment of the present disclosure.

For reference, FIG. 29 shows a state in which the seating part 20 protrudes from the portable printer 1, FIG. 30 shows a state in which the seating part 20 is being retracted, and FIG. 31 shows a state in which the seating part 20 is retracted.

According to FIGS. 29 to 31, the portable printer 1 according to the seventh embodiment of the present disclosure differs in the configuration of the printing adjustment unit 100 compared to the above fifth and sixth embodiments.

The elastic member 110 included in the printing adjustment unit 100 of the present embodiment is the same as the previous embodiment in that it is provided between the main body 10 and the seating part 20, and that the elastic member 110 has an elastic force to maintain the seating part 20 in the restoration position of the retracted position or the protruding position with respect to the main body 10.

However, the elastic member 110 of the present embodiment may differ from the fifth and sixth embodiments using the tension spring in that it is a compression spring for maintaining the seating part 20 in the protruding position. In other words, the portable printer 1 of the present embodiment may cause the seating part 20 to protrude with respect to the main body 10 by an elastic force by using the compression spring. In other words, the seating part 20 of the present embodiment may maintain the protruding position as a restoration position based on the elastic force of the elastic member 110.

In this case, the portable printer 1 of the present embodiment may have a vertical height of about 6.5 mm between the head 32 and the roller 21 when the seating part 20 is placed in a protruding position. At this time, in the process of sliding the roller 21 to the skin, the elastic member 110 provides sufficient elastic force to the seating part 20, so that the vertical height between the head 32 and the roller 21 may be appropriately maintained.

The operating member 120 of the present embodiment is the same as the fifth and sixth embodiments in that the seating part 20 is placed at a change position of one of the retracted position or the protruding position by external manipulation.

On the other hand, the operating member 120 of the present embodiment may be provided in the main body 10 rather than the seating part 20. In other words, the portable printer 1 of the previous embodiment performs an operation on the seating part 20 so that the seating part 20 is placed in the change position, and the portable printer 1 of the present embodiment performs an operation on the main body 10 to place the seating part 20 in the change position.

The change position of the present embodiment may be the retracted position in which the seating part 20 is retracted, as in the fifth and sixth embodiments. The operating member 120 may be provided in the main body 10 and operably through the appearance of the main body 10. For example, the operating member 120 may be exposed to the outside of the main body 10, or a manipulation portion outside the main body 10 may be connected to an end of the operating member 120 accommodated inside the main body 10.

The operating member 120 has a structure in which it is engaged to limit the protrusion of the seating part 20 while the seating part 20 is retracted. To this end, a locking protrusion 140 may be provided on one side of the seating part 20 facing the operating member 120. When the locking protrusion 140 and the operating member 120 touch each other, movement in the inner and outer directions may be restricted.

The operating member 120 may include the operation button 121, and one end of the operating button 121 may be exposed to the outside or operable from the outside, and the other end may be in contact with the locking protrusion 140 to limit the movement of the seating part by the elastic member 110. However, before the seating part 20 is placed in the retracted position, the operation button 121 may not be engaged with the locking protrusion 140. On the other hand, when the seating part 20 is placed in the retracted position, the operation button 121 may be moved to the position where it is engaged with the locking protrusion 140, and the operation button 121 is placed in a position where it faces the locking protrusion 140 in the inner and outer directions by movement of the operation button 121. In this case, despite the elastic force of the elastic member 110, the seating part 20 cannot protrude and maintains the retracted position.

On the other hand, when the other end of the operation button 121 is moved by a manipulation of one end and the operation button 121 is deviated from the locking protrusion 140, the seating part is subjected to an elastic force moving in the outward direction by the elastic member 110, and the seating part 20 is allowed to move.

In other words, this embodiment may include an operation contrary to the sixth embodiment. While the retraction of the seating part 20 is made by the disengagement of the operation button 121 and the locking protrusion 130 and the elastic force of the elastic member 110 in the sixth embodiment, the entrance of the seating part 20 may be made by pressurization of the seating part 20 in this embodiment. In addition, in the sixth embodiment, the seating part 20 maintains the retracted position by the elastic member 110, which is accomplished by engagement of the operation button 121 with the locking protrusion 140.

On the other hand, in the sixth embodiment, the protrusion of the seating part 20 may be achieved by artificial manipulation, while in the present embodiment, the protrusion of the seating part 20 is achieved by the disengagement of the operation button 121 and the locking protrusion and the elastic force of the elastic member 110. In addition, while the seating part 20 maintains the protruding position by engagement of the operation button 121 with the locking protrusion 130 in the sixth embodiment, it is achieved by the elastic member 110 in the present embodiment.

Therefore, compared with the sixth embodiment, the present embodiment may be implemented in a manner contrary to the retraction, protrusion, maintenance of position, and the like of the seating part 20. Of course, the present embodiment and the sixth embodiment may be combined.

Hereinafter, in the present embodiment, a method in which the user retracts/protrudes the seating part 20 will be described.

The portable printer 1 of the present embodiment may first be in a state where the seating part 20 protrudes as shown in FIG. 29. In this case, the height between the nozzle 33 and the roller 21 may be an appropriate value for printing an image on the skin.

When the user wishes to print on the hard target such as paper, the user may move the seating part 20 in the inner direction of the main body 10. In this case, the movement of the seating part 20 may be made by direct manipulation of the seating part 20, or various configurations described herein may be used.

When the seating part 20 is retracted to a predetermined level, the user manipulates the operation button 121 so that the operation button 121 is placed in a position facing the locking protrusion 140. At this time, even if the force to retract the seating part 20 is removed, the operation button 121 may contact the locking protrusion 140 to suppress the protrusion of the seating part 20. Therefore, in this case, the elastic member 110 may remain compressed.

Thereafter, when the user wants to print on the soft target such as skin, the user manipulates the operation button 121 in a direction deviated from the locking protrusion 140. At this time, since the seating part 20 automatically protrudes by the elastic force of the elastic member 110, the vertical height of the nozzle 33 and the roller 21 may be restored to about 6.5 mm again.

The present disclosure may cover a case in which the operation button 121 and the locking protrusion 140 in the seventh embodiment are mutually reversed. For example, as a modified embodiment, a portion corresponding to the operation button 121 of the seventh embodiment may be a locking portion fixed in the main body 10, and a portion corresponding to the locking protrusion 140 of the seventh embodiment may be a movable operation portion provided on the seating part 20.

In other words, the present disclosure includes a modified example in which the relative movement between the operation button 121 and the locking protrusion 140 in the present embodiment is used as it is, and the operation button 121 is provided in the seating part 20 and the locking protrusion 140 is provided in the seating part 20.

FIGS. 32 to 35 are cross-sectional views of a portable printer according to an eighth embodiment of the present disclosure.

Figure 32:
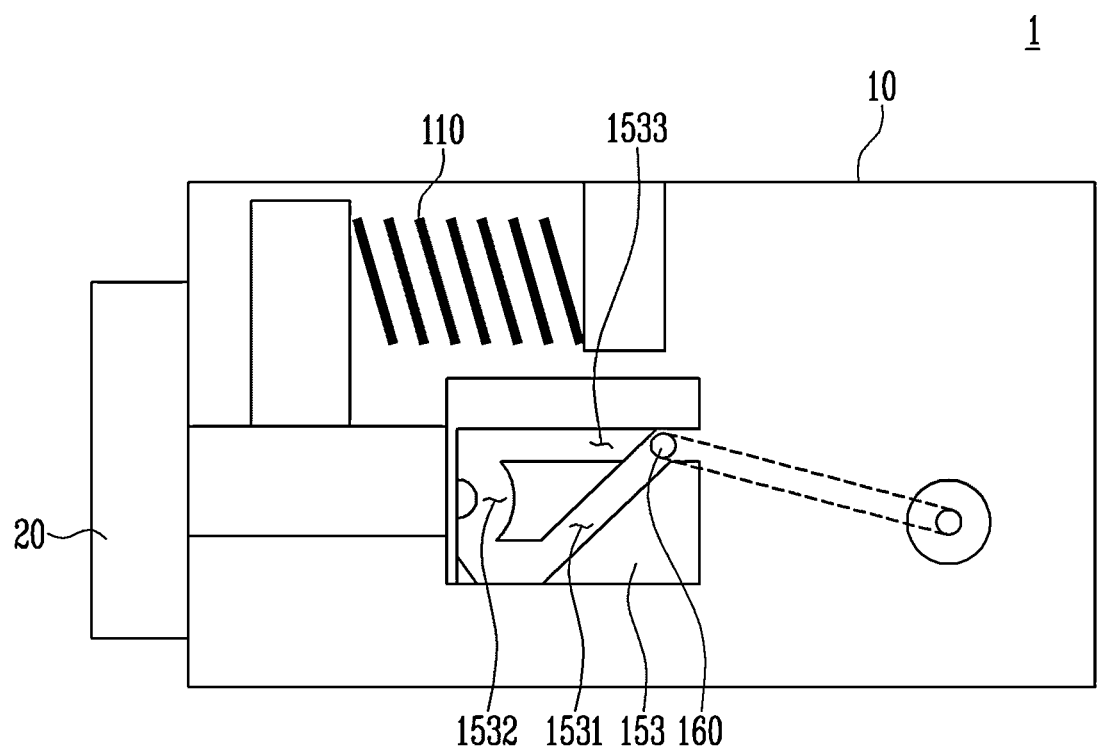
FIG. 32 is a cross-sectional view of a portable printer according to an eighth embodiment of the present disclosure.
Figure 33:
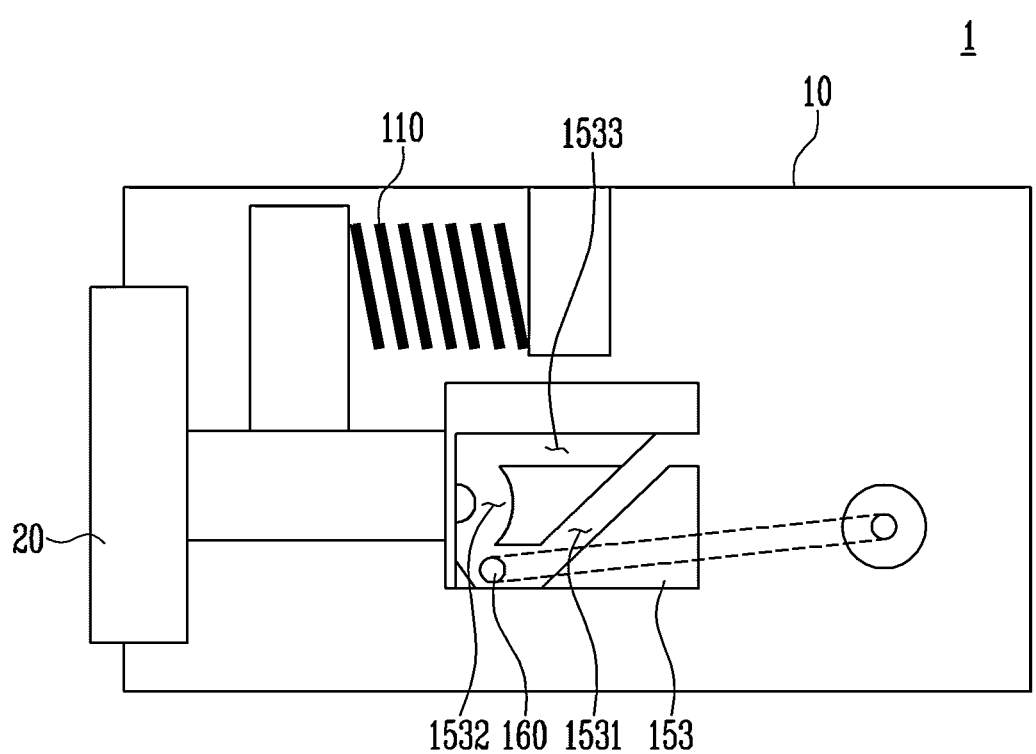
FIG. 33 is a cross-sectional view of the portable printer according to the eighth embodiment of the present disclosure.
Figure 34:
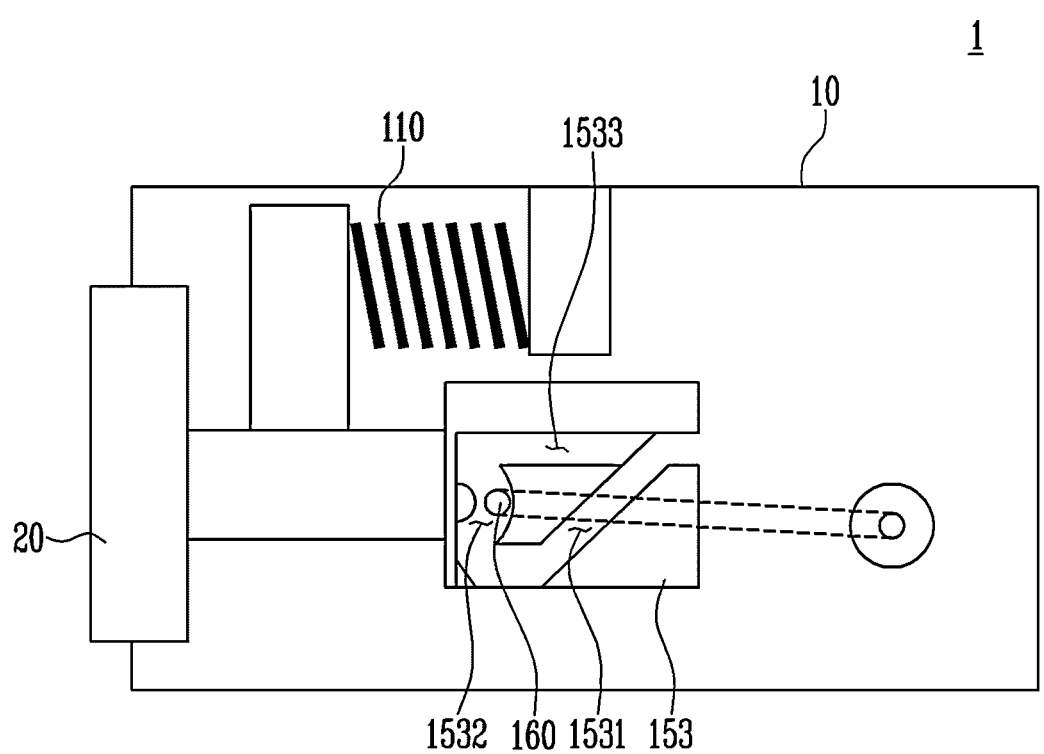
FIG. 34 is a cross-sectional view of the portable printer according to the eighth embodiment of the present disclosure.
Figure 35:
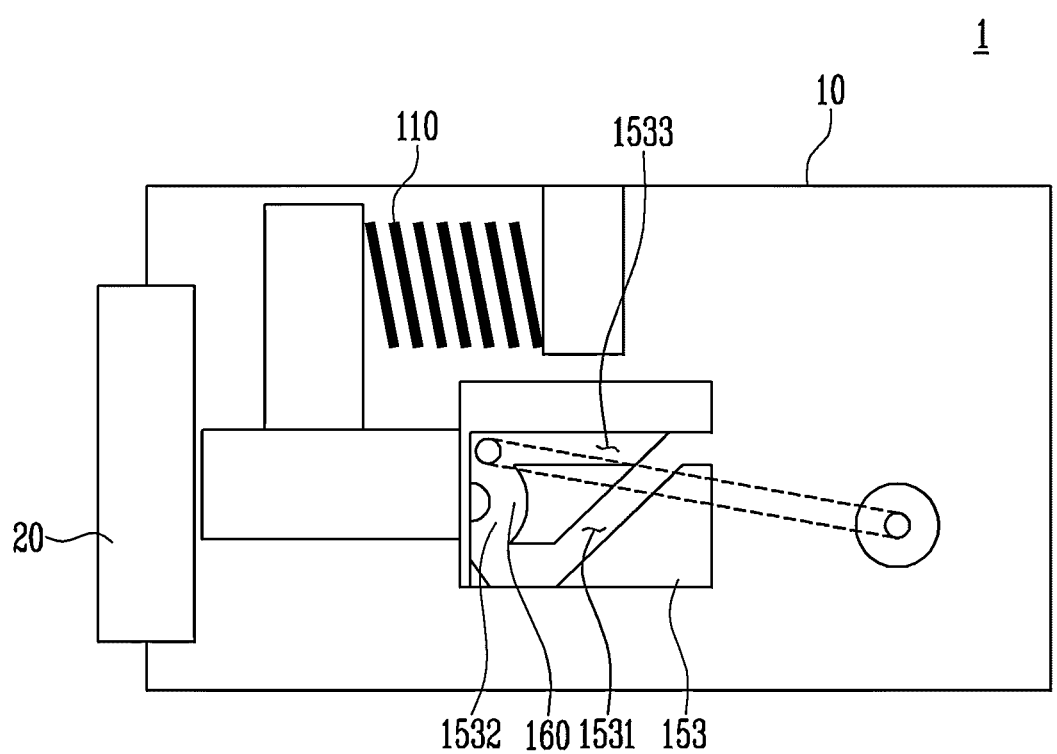
FIG. 35 is a cross-sectional view of the portable printer according to the eighth embodiment of the present disclosure.

In this case, FIG. 32 shows a state in which the seating part protrudes, FIG. 33 shows a state in which the seating part 20 is retracted, and FIG. 34 shows a state in which the seating part 20 is fixed in the retracted position. On the other hand, FIG. 35 shows a state in which the seating part 20 is changed from the retracted position to the protruding position.

The present embodiment may borrow a configuration (pop-up button, etc.) applied to a product pertaining to a different technical field from the present disclosure. It will be explained in detail below.

In this embodiment, the printing adjustment unit 100 may be used to change/maintain the protruding position or the retracted position of the seating part 20. At this time, the printing adjustment unit 100 has an adjustment piece 153 and the elastic member 110.

The adjustment piece 153 includes a path through which a locking pin 160 provided in the main body 10 moves or a groove 1532 with which the locking pin 160 engages. The adjustment piece 153 may move in the inner and outer directions of the main body 10, wherein the locking pin 160 moves along the path and the groove 1532 provided in the adjustment piece 153 to change or fix the position of the seating part 20.

The adjustment piece 153 may be provided to be fixed to the seating part 20 and may move in the inner and outer directions of the main body 10 together with the seating part 20. The adjustment piece 153 has a first path 1531 through which the locking pin 160 moves when the seating part 20 moves in the direction of being retracted into the main body 10.

The first path 1531 may be provided inclined, and for this purpose, the locking pin 160 may have a rotatable structure within the main body 10. For example, the locking pin 160 may be provided in a ⊂-shape, its upper end is rotatably fixed in position within the main body 10, and the other end may be seated on the adjustment piece 153.

The adjustment piece 153 has the groove 1532 connected to an end of the first path 1531 and in which the locking pin 160 is seated. The groove 1532 may have a convex shape toward the inside of the main body 10. When the locking pin 160 is located on the groove 1532, the adjustment piece 153 and the seating part 20 may be restricted from movement in the direction of protruding from the main body 10.

The adjustment piece 153 also has a second path 1533 connecting an end of the groove 1532 with one end of the first path 1531. The second path 1533 may form a straight line and may cause the locking pin 160 leaving the groove 1532 to return to the first path 1531.

The printing adjustment unit 100 of the present embodiment may include the elastic member 110 between the seating part 20 and the main body 10. In this case, the elastic member 110 may be provided between the main body 10 and the adjustment piece 153 in addition to the seating part 20 and the main body 10.

Hereinafter, in the present embodiment, a method of the seating part 20 moving inner and outer directions will be described.

In FIG. 32, the seating part 20 is placed in the protruding position. At this time, the protrusion of the seating part 20 is supported by the elastic force of the elastic member 110, and additional protrusion may be limited by a locking structure between the seating part 20 and the lower body 12.

As shown in FIG. 33, when the seating part 20 moves in the direction in which it is retracted into the main body 10 by external manipulation, the locking pin 160 moves obliquely along the first path 1531 of the adjustment piece 153. Thereafter, when the seating part 20 is sufficiently retracted into the main body 10, the locking pin 160 may be seated in the groove 1532 as shown in FIG. 34 beyond the end of the first path 1531 provided in the adjustment piece 153.

As such, in order for the locking pin 160 to pass from the first path 1531 to the groove 1532, between the first path 1531 and the groove 1532, an inclined surface/curved surface structure or the like that induces the movement of the locking pin 160 may be applied.

Since the locking pin 160 is seated in the groove 1532 in the state shown in FIG. 34, the adjustment piece 153 may not move in the outer direction of the main body 10 despite the elastic force of the elastic member 110. Therefore, the seating part 20, which is integrally fixed with the adjustment piece 153, also may not protrude compared to the main body 10 and may maintain the retracted position.

Thereafter, when the seating part 20 is further retracted into the main body 10 by the user's manipulation, the locking pin 160 exits the groove 1532 and enters the second path 1533, resulting in a state shown in FIG. 35. In FIG. 35, since the elastic member 110 may push the seating part 20, the seating part 20 moves in the protruding direction with respect to the main body 10 and changes to the protruding position, and the locking pin 160 passes through the second path 1533 and returns to one end of the first path 1531.

In other words, in this embodiment, the seating part 20 may alternately maintain the protruding position or the retracted position through a manipulation of pressing the seating part 20 in the inner direction, so that adjustment of the height of the seating part 20 is easy.

Figure 36:
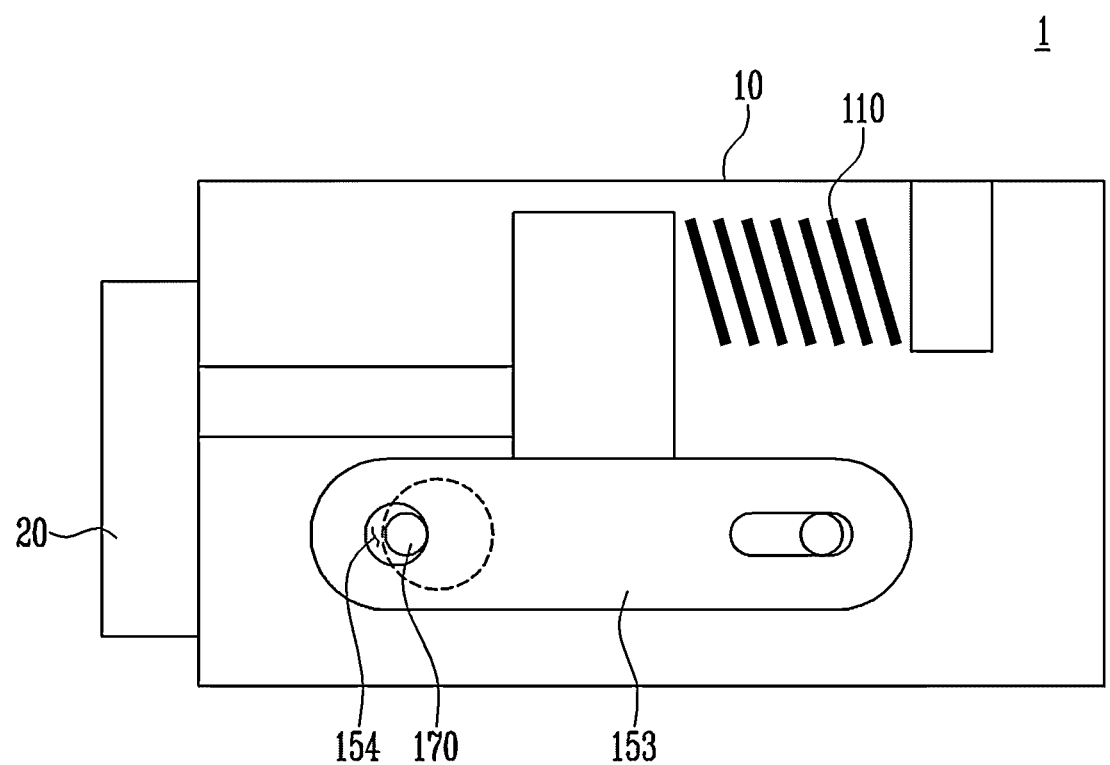
FIG. 36 is a cross-sectional view of a portable printer according to a ninth embodiment of the present disclosure.
Figure 37:
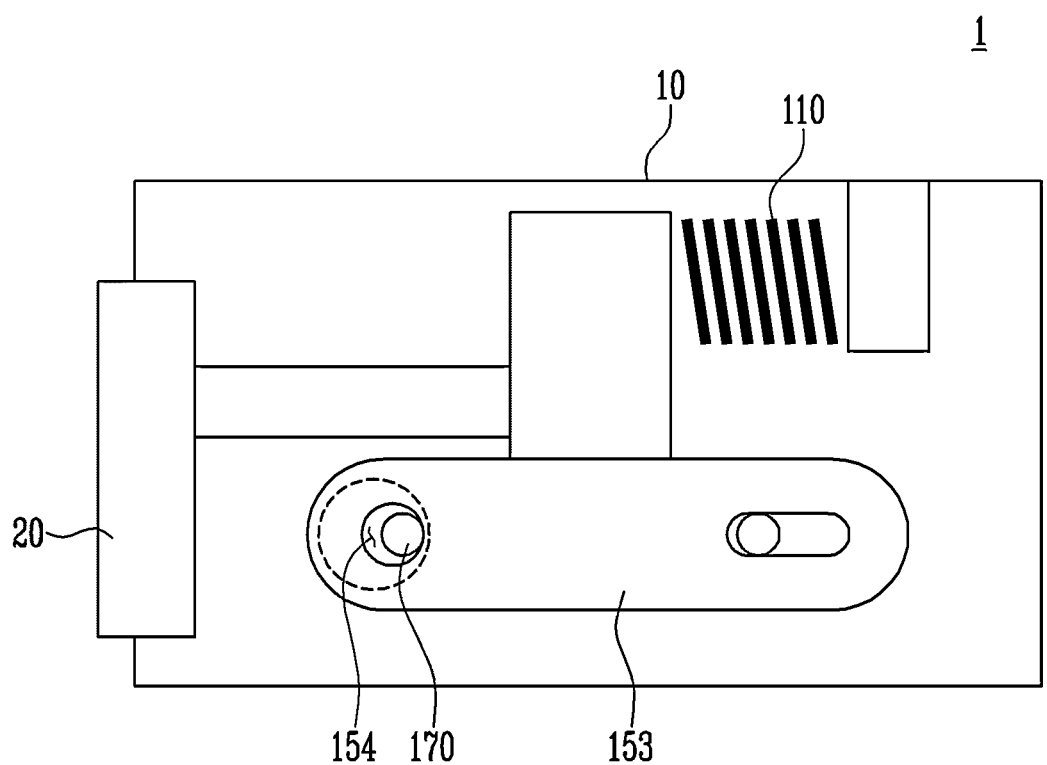
FIG. 37 is a cross-sectional view of the portable printer according to the ninth embodiment of the present disclosure.

FIGS. 36 and 37 are cross-sectional views of a portable printer according to a ninth embodiment of the present disclosure.

In this case, FIG. 36 shows a state in which the seating part protrudes, and FIG. 37 shows a state in which the seating part 20 is retracted.

The printing adjustment unit 100 of the present embodiment may be similar to the eighth embodiment in that it includes the adjustment piece 153 and the elastic member 110. However, the adjustment piece 153 of the present embodiment differs from the previous embodiment in terms of shape.

The adjustment piece 153 of the present embodiment may be connected to the seating part 20 and may be provided to move in the inner and outer directions integrally with the seating part 20. At this time, the adjustment piece 153 has a groove for accommodating a rotating protrusion 170 provided in the main body 10.

The rotating protrusion 170 rotatable by a driving source including a motor or an external manipulation may be provided inside the main body 10, and the rotating protrusion 170 has a shape of rotating eccentrically. In other words, a rotation shaft (not shown) for rotating the rotating protrusion 170 is arranged so that it is not parallel with the center of the rotating protrusion 170. Therefore, the rotating protrusion 170 may change its position in the inner and outer directions of the main body 10 when the rotation shaft is rotated.

The adjustment piece 153 accommodates the rotating protrusion 170 in a hole 154 and has a form of translational movement by eccentric rotation of the rotating protrusion 170. The rotating protrusion 170 may move along a predetermined circular path in the main body 10 as it rotates eccentricly. At this time, the hole 154 accommodates the circular movement of the rotating protrusion 170, but is pushed by the movement of the rotating protrusion 170 in the inner and outer directions to induce movement of the adjustment piece 153.

The printing adjustment unit 100 of the present embodiment includes the elastic member 110, which is provided between the main body 10 and the seating part 20 or between the main body 10 and the adjustment piece 153. The elastic member 110 may be at least one of a tension spring or an elastic spring, and may have an elastic force in the direction of pushing the seating part 20 out of the main body 10. In this case, the rotating protrusion 170 accommodated in the hole 154 may always face an inner end of the hole 154.

Hereinafter, with reference to the drawings, the movement of the seating part 20 in the inner and outer directions will be described.

According to FIG. 36, the rotating protrusion 170 is located at the outermost end on an eccentric rotating circular path. Since the inner end of the hole 154 comes into contact with the rotating protrusion 170 by the elastic force of the elastic member 110, the adjustment piece 153 is moved outward. Therefore, in FIG. 36, the seating part 20 may be placed in the protruding position.

On the other hand, in the case of FIG. 37, the rotating protrusion 170 is located at the innermost end on the eccentric rotating circular path. At this time, since the hole 154 has to move inward with its inner end in contact with the rotating protrusion 170, the adjustment piece 153 moves inward. Therefore, in FIG. 37, the seating part 20 may be placed in the retracted position.

When the seating part 20 is placed in the protruding position, the seating part 20 is maintained in a constant position by the elastic force of the elastic member 110 and the contact between the rotating protrusion 170 and the hole 154. In addition, when the seating part 20 is placed in the retracted position, the seating part 20 may also maintain a constant position by the elastic force of the elastic member 110 and the contact between the rotating protrusion 170 and the hole 154.

The present embodiment may further include a guide path (symbol not shown) and a guide pin (symbol not shown) for guiding the adjustment piece 153 to move vertically in the inner and outer directions. The guide path has a width corresponding to the diameter of the guide pin and is made in a vertically extended form. Since the guide pin may be fixed to the main body 10, the position of the guide pin in the guide path is constantly changed when the adjustment piece 153 is moved, thereby suppressing shaking of the adjustment piece 153.

FIG. 38 is a cross-sectional view of a portable printer 1 according to a tenth embodiment of the present disclosure.

Figure 38A:
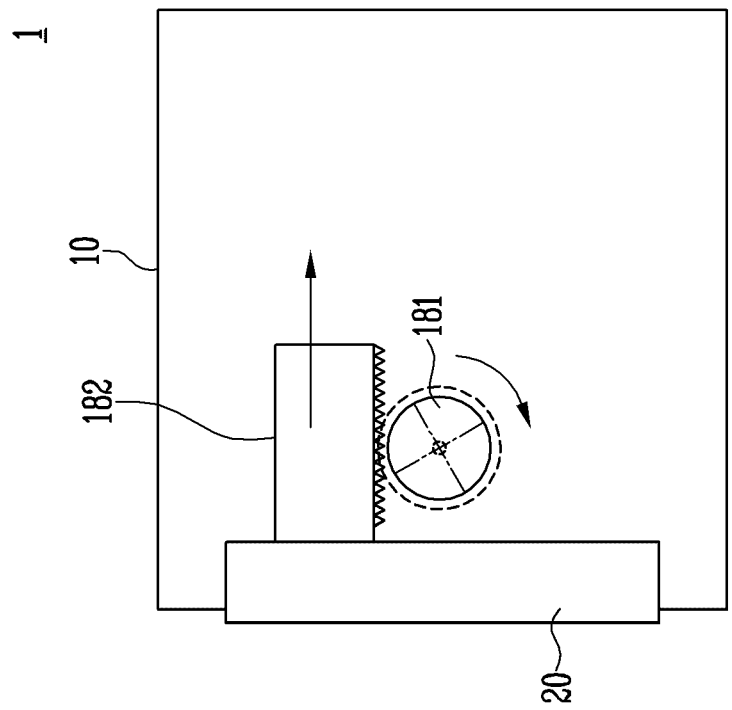
FIG. 38 is a cross-sectional view of a portable printer according to a tenth embodiment of the present disclosure.
Figure 38B:
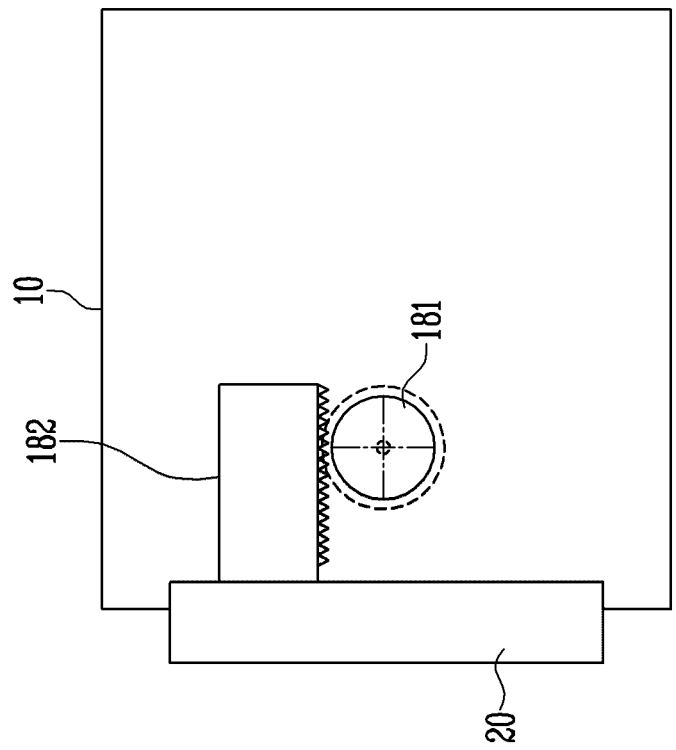

Here, FIG. 38(A) shows a state in which that the seating part 20 protrudes, and FIG. 38(B) shows a state in which the seating part is retracted.

Referring to FIG. 38, the portable printer 1 according to the tenth embodiment of the present disclosure includes the printing adjustment unit 100 includes an operation gear 181 and a rack 182.

The rack 182 is provided to extend from the seating part 20 toward the inner side of the main body 10 and may be provided perpendicular to the seating part 20. In this case, movement of the seating part 20 by the rack 182 is performed along the inner and outer directions of the main body 10.

The rack 182 may be engaged with the operation gear 181. The operation gear 181 may be operated by external manipulation, internal manipulation, automatic/manual manipulation, or the like, and may be rotated at a predetermined angle or a predetermined number of wheels by manipulation.

The operation gear 181 and the rack 182 are engaged with each other through gear teeth (symbol not shown). In this case, when the operation gear 181 rotates, the rack 182 engaged with the operation gear 181 moves translationally. Since the seating part 20 may be provided integrally with the rack 182, the seating part 20 moves in the inner and outer directions of the main body 10 when the rack 182 moves.

In this embodiment, the user inputs an unrestricted manipulation such as a button to the main body 10, and the operation gear 181 is rotated and operated by this input. When the control gear 181 rotates, the rack 182 may move and the seating part 20 may move up and down.

Of course, as described above, in addition to manual manipulation by the user, automatic manipulation according to detection of the surface of the target may also be possible.

In addition, since the present embodiment uses the rack 182 and rack 182 gear, the elastic member 110 may be omitted. In addition, in the present embodiment, the seating part 20 may be used at an intermediate height in addition to the heights when the surface of the target is soft and hard.

FIG. 39 is a cross-sectional view of a portable printer 1 according to an eleventh embodiment of the present disclosure.

In this case, FIG. 39(A) shows a state in which the seating part 20 protrudes, and FIG. 39(B) shows a state in which the seating part is retracted.

Referring to FIG. 39, in the portable printer 1 according to the eleventh embodiment of the present disclosure, the printing adjustment unit 100 includes the elastic member 110 and a link arm 183.

The elastic member 110 may be a compression spring that pushes the seating part 20 in a protruding direction. one or more of the elastic members 110 are provided and provide uniform elastic force for the entire surface of the seating part 20 facing the target.

The link arm 183 consists of a joint structure having one or more bending points. The link arm 183 has a fixed point and an operation point fixed to the seating part 20, and has a bending point between the operation point and the fixed point. The link arm 183 may have a form of a plurality of bars being rotatable connected at a point.

The link arm 183 may refer to a bar connected to the operation point as an operation bar (symbol not shown), a bar connected to the fixed point of the seating part 20 as a lifting bar (symbol not shown), and the operation bar and the lifting bar may be directly connected as shown in the drawings, or one or more connecting bars may be added thereto. In this case, when the operation bar rotates with the operation point as the starting point by internal/external/automatic/manual manipulation, the lifting bar connected to the operation bar through the bending point also rotates.

At this time, the lifting bar is connected between the bending point and the fixed point, and when the operation bar rotates, the bending point moves in the inner and outer directions. Therefore, the lifting bar also moves in the inner and outer directions, and the lifting bar rotates partially, causing the fixed point and the bending point to be slightly deviated in the inner and outer directions.

In other words, the link arm 183 is a configuration capable of connecting a rotation operation at the operation point to the lifting operation at the fixed point, and when rotation of the operation bar is performed by the user or internally in the main body 10, moving up and down of the seating part 20 is implemented.

At this time, the elastic member 110 is used to smooth the rotation of the link arm 183 and to maintain a stable protrusion or retraction state of the seating part 20, and the elastic member 110 may use or add an elastic spring in addition to the compression spring if necessary.

FIG. 40 is a cross-sectional view of the portable printer 1 according to a twelfth embodiment of the present disclosure.

Figure 40A:
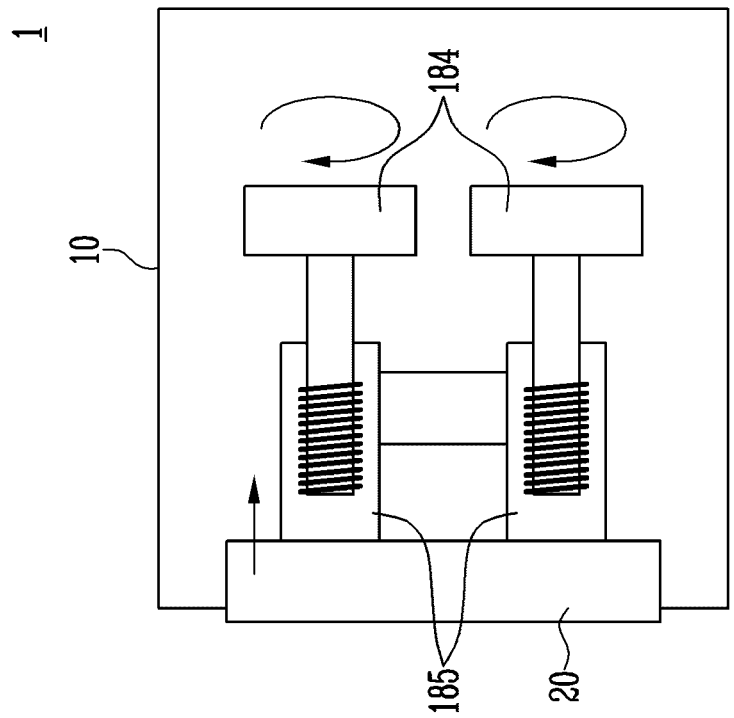
FIG. 40 is a cross-sectional view of a portable printer according to a twelfth embodiment of the present disclosure.
Figure 40B:
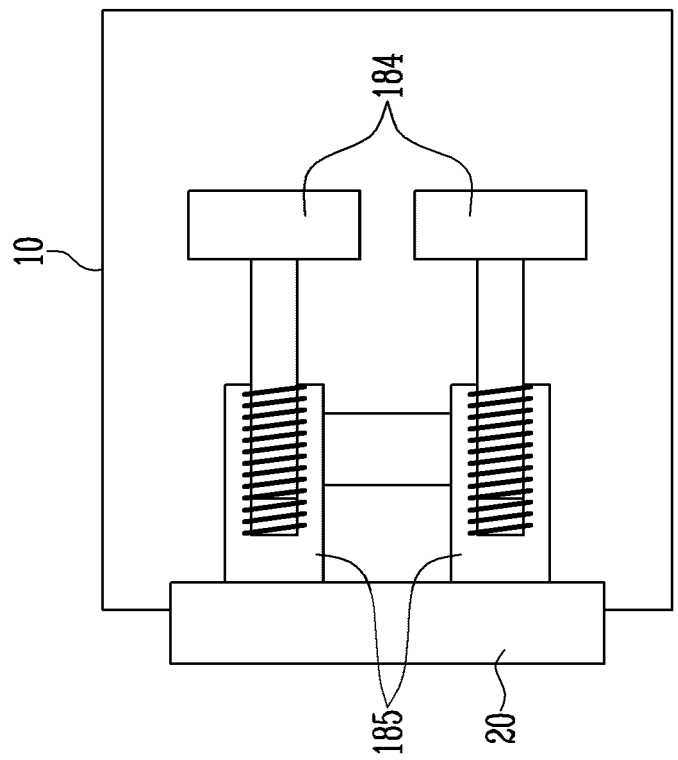

In this case, FIG. 40(A) shows a state in which the seating part 20 protrudes, and FIG. 40(B) shows a state in which the seating part is retracted.

Referring to FIG. 40, in the portable printer 1 according to the twelfth embodiment of the present disclosure, the printing adjustment unit 100 includes a driving bolt 184 and a driven nut 185.

The driving bolt 184 may be provided in the main body 10 and one side may be provided externally operable. The driving bolt 184 may be provided in a form in which its head is provided outside the main body 10 and can implement rotation of the driving bolt 184 outside the main body 10. In this case, a concave-convex structure for increasing manipulation convenience may be applied to at least a portion of the head of the driving bolt 184 for receiving the user's manipulation.

The driven nut 185 may be provided in the inner direction of the main body 10 in the seating part 20. The driven nut 185 is screwed with the driving bolt 184, and rotation of the driven nut 185 is limited when the driving bolt 184 is screwed. Therefore, when the driving bolt 184 rotates, the driven nut 185 may have a form of moving up and down along a screw thread without rotating. To this end, the driving bolt 184 may be provided in a structure that is rotatable but cannot be moved up and down.

Two driving bolts 184 and two driven nuts 185 may be provided, and when two driven nuts 185 are provided in one seating part 20, the driven nut 185 may naturally be restricted from rotating. Alternatively, an interference structure that limits the rotation of the driven nut 185 may be provided around the driven nut 185 in the main body 10.

In this embodiment, when the user manipulates the driving bolt 184, the driven nut 185 moves up and down along the screw thread of the driving bolt 184 in a state where rotation is restricted while the driving bolt 184 rotates. At this time, the seating part 20 having the driving bolt 184 moves in the inner and outer directions of the main body 10.

Since the present embodiment uses the screw lifting method as in the tenth embodiment, the elastic member 110 may be omitted. In addition, using the screw lifting method, it is possible to move up and down the seating part 20 finely, and the height of the seating part 20 may be adjustable in a plurality of steps rather than two steps.

However, since it is preferable to set the seating part 20 at an optimal height according to a case where the target is soft or hard, an identification factor capable of identifying an optimal position along the surface of the target may be added to the driving bolt 184 or the main body 10.

Alternatively, a structure that generates a tactile sensation or sound when the seating part 20 reaches a height for paper printing or skin printing is applied to the seating part 20 or the driven nut 185, etc., thereby increasing the reliability of printing quality.

As described above, the method of limiting or proposing the height of the seating part 20 to a predetermined value may be sufficiently applied to other embodiments in addition to the present embodiment.

FIG. 41 is a cross-sectional view of the portable printer 1 according to a thirteenth embodiment of the present disclosure.

Figure 41A:
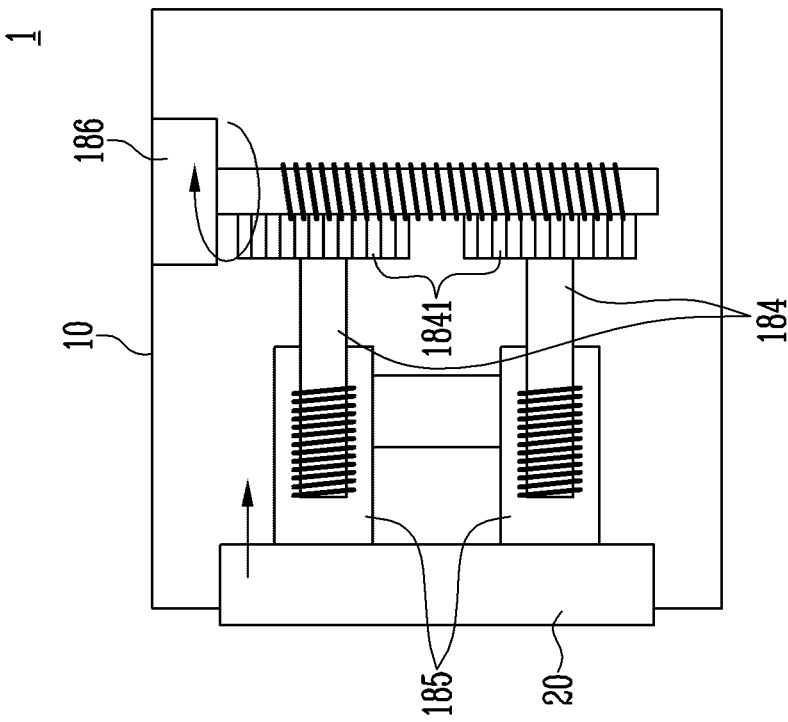
FIG. 41 is a cross-sectional view of a portable printer according to a thirteenth embodiment of the present disclosure.
Figure 41B:
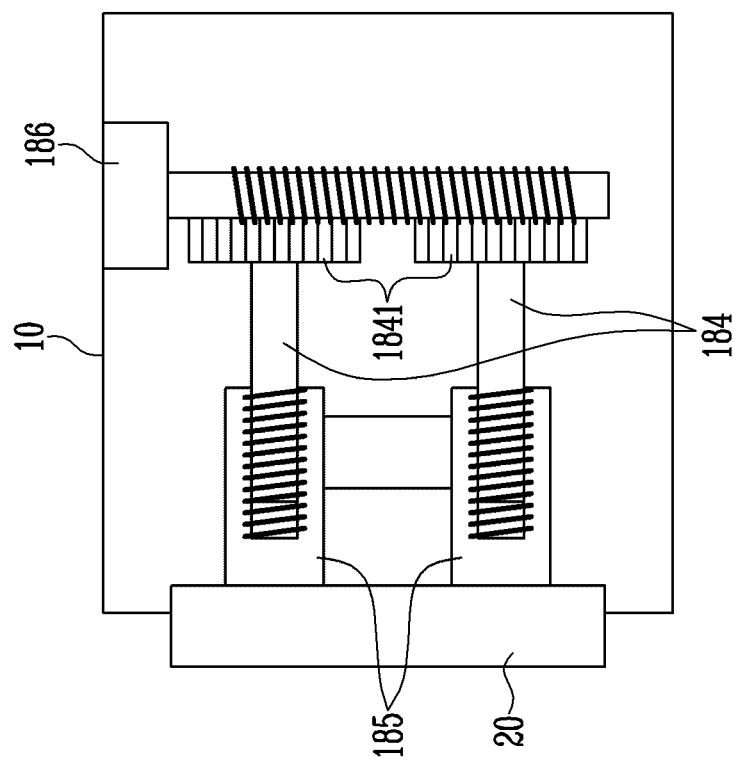

In this case, FIG. 41(A) shows a state in which the seating part 20 protrudes, and FIG. 41(B) shows a state in which the seating part is retracted.

Referring to FIG. 41, in the portable printer 1 according to the thirteenth embodiment of the present disclosure, the printing adjustment unit 100 may further include an operation bolt 186 compared to the twelfth embodiment.

This embodiment includes the driving bolt 184 and the driven nut 185, and in the case of the preceding embodiment, when there are a plurality of the driving bolts 184, the user should simultaneously manipulate the plurality of driving bolts 184 to move up and down the seating part 20 in parallel.

In other words, in the case that the user manipulates the plurality of driving bolts 184 differently in the previous embodiment, a problem may occur in lifting as the seating part 20 is tilted. Therefore, in the present embodiment, when there are a plurality of the driving bolts 184, all of the plurality of driving bolts 184 are operated by one operation bolt 186.

At this time, the driving bolt 184 provides a worm gear 1841 at the head, and the worm gear 1841 engages with a screw thread of the operation bolt 186, so that when the operation bolt 186 rotates, the driving bolt 184 may rotate in a direction different from the operation bolt 186.

In other words, in the present embodiment, when a plurality of the driving bolts 184 are provided for stably moving up and down the seating part 20, the plurality of driving bolts 184 are operated at once with one operation bolt 186 to allow the seating part 20 to be moved up and down while uniformly maintaining a state parallel to the surface of the target.

FIG. 42 is a cross-sectional view of the portable printer 1 according to a fourteenth embodiment of the present disclosure.

In this case, FIG. 42(A) shows a state in which the seating part 20 protrudes, and FIG. 42(B) shows a state in which the seating part is retracted.

Referring to FIG. 42, in the portable printer 1 according to the fourteenth embodiment of the present disclosure, the printing adjustment unit 100 may include the elastic member 110 and an operation lever 187.

The elastic member 110 may be a tension spring as a configuration for elastically moving the seating part 20 in the inner direction of the main body 10. In other words, the elastic member 110 may be a configuration of restoring the seating part 20 to FIG. 42(B) when there is no external force.

One end of the operation lever 187 may be provided to be operable from the outside. At this time, the operation lever 187 is rotatable based on a rotation center provided at the other end, and an eccentric pin 1871 may be provided at the other end of the operation lever 187.

The eccentric pin 1871 may come into contact with the seating part 20 and may restrict the seating part 20 from moving in the inner direction of the main body 10. Furthermore, the eccentric pin 1871 may push the seating part 20 in the outer direction of the main body 10.

The eccentric pin 1871 may be provided at a position spaced apart from the rotation center of the operation lever 187. In this case, when the operation lever 187 is rotated, the eccentric pin 1871 provided at the other end of the operation lever 187 moves inward and outward with respect to the seating part 20 while moving eccentrically.

When the eccentric pin 1871 is in the state of FIG. 42(A), the seating part 20 may be placed in the protruding position from the main body 10, whereas when the eccentric pin 1871 is in the state of FIG. 42(B), the seating part 20 may be retracted into the inner side of the main body 10 by the elastic member 110.

Conversely, when the eccentric pin 1871 moves from the state of FIG. 42(B) to the state of FIG. 42(A) by rotation of the operation lever 187, the eccentric pin 1871 may push the seating part 20 to the outside of the main body 10 while overcoming the tensile elastic force of the elastic member 110. This method may be similar to the cam method in FIG. 21 to some extent, but operation convenience may be increased in that it can be operated from the side of the main body 10.

FIG. 43 is a cross-sectional view of the portable printer 1 according to a fifteenth embodiment of the present disclosure.

Figure 43B:
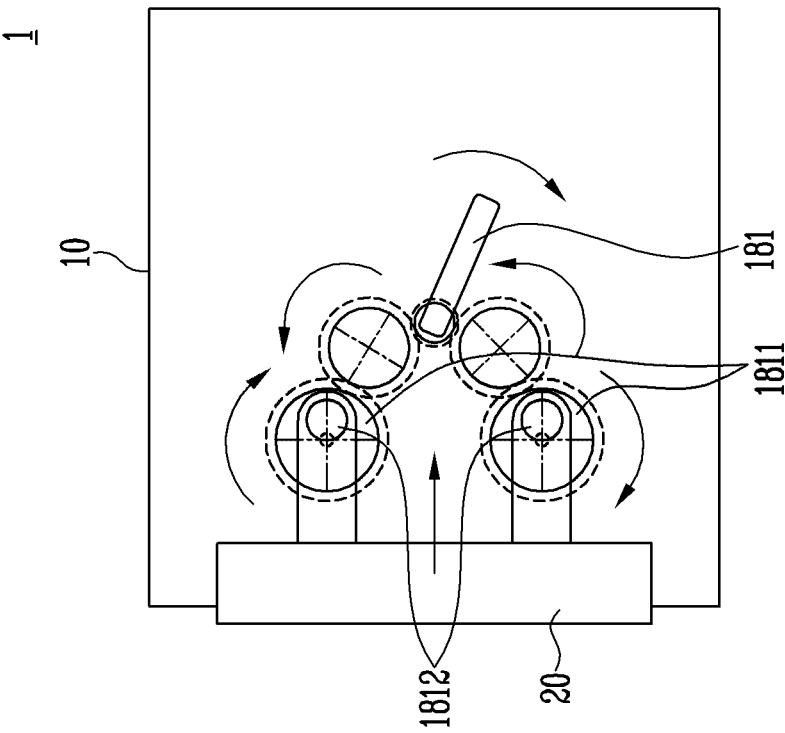
FIG. 43 is a cross-sectional view of a portable printer according to a fifteenth embodiment of the present disclosure.
Figure 43A:
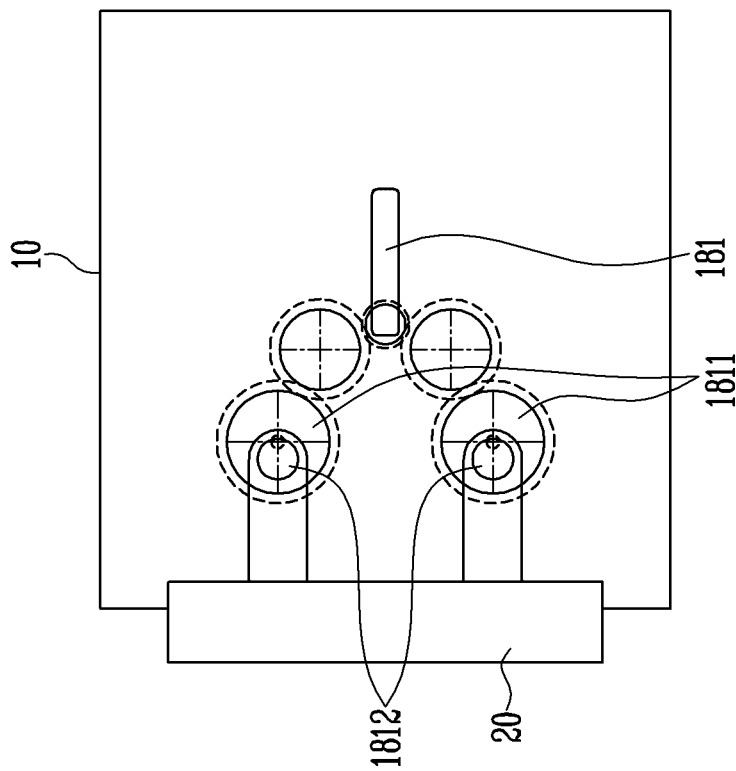

In this case, FIG. 43(A) shows a state in which the seating part 20 protrudes, and FIG. 43(B) shows a state in which the seating part is retracted.

Referring to FIG. 43, in the portable printer 1 according to the fifteenth embodiment of the present disclosure, the printing adjustment unit 100 includes the operation gear 181, a driven gear 1811, and an eccentric shaft 1812.

The operation gear 181 is similar to that described in FIG. 38, and in this embodiment, a lever for manipulation of the operation gear 181 may be integrally provided in the operation gear 181 as shown in the drawing. Of course, on the contrary, in the case of the embodiment shown in FIG. 38, a lever may also be added.

The operation gear 181 may be connected to the driven gear 1811. The driven gear 1811 engages with the operation gear 181 through gear teeth, and rotates along a predetermined direction by rotation of the operation gear 181.

An eccentric shaft 1812 may be provided in the driven gear 1811, and the eccentric shaft 1812 is connected to the seating part 20. The seating part 20 may have a structure in which the eccentric shaft 1812 rotates idle. For example, the seating part 20 is provided to surround the eccentric shaft 1812 with a bearing or the like, and rotation of the eccentric shaft 1812 may not generate movement of the seating part 20. The seating part 20 may be provided in a structure of moving together with the eccentric shaft 1812 when the eccentric shaft 1812 moves in inner or outer directions.

Since the eccentric shaft 1812 may move along an arc-shaped path by rotation of the driven gear 1811 in addition to moving in the inner and outer directions of the main body 10, there is a risk of causing horizontal movement with respect to the seating part 20.

To prevent this, the seating part 20 may be connected to a bearing portion that covers the eccentric shaft 1812 so that it rotates idle in a hinged rotatable structure. In other words, when the eccentric shaft 1812 rotates along a circle, the seating part 20 has a structure that changes a revolution motion of the eccentric shaft 1812 to a translational motion. Therefore, the portion in which the bearing is provided in the seating part 20 may be tilted within a predetermined angle in the process of moving up and down the seating part 20.

The driven gear 1811 in which the eccentric shaft 1812 is provided may directly engage with the operation gear 181, or at least one connection gear (symbol not shown) may be provided between the driven gear 1811 provided with the eccentric shaft 1812 and the operation gear 181 in consideration of manipulability of the operation gear 181 (manipulation angle, manipulation direction, etc.).

In FIG. 43(A), when the user rotates the operation gear 181 through a lever or the like, the operation gear 1811 engaged with the operation gear 181 rotates. At this time, the eccentric shaft 1812 rotates to the inner side of the main body 10 as shown in FIG. 43(B).

The eccentric shaft 1812 may move in a circular arc, but the seating part 20 may not receive any movement of the eccentric shaft 1812 except for movement toward the inside of the main body 10. In other words, the seating part 20 may prevent a portion of the seating part 20 facing the surface of the target from rotating horizontally or tilting despite the revolution of the eccentric shaft 1812 through a bearing, a hinge rotating structure, or the like.

In other words, the seating part 20 may move in the inner and outer direction by using the eccentric shaft 1812 moving in the inner and outer directions of the main body 10 when the eccentric shaft 1812 revolves.

This embodiment may not use screw coupling, and as in the previous tenth embodiment, the elastic member 110 may be omitted. On the other hand, the elastic member 110 (at least one of a compression spring and a tension spring) may be added for stable contact between the seating part 20 and the surface of the target.

FIG. 44 is a cross-sectional view of the portable printer 1 according to an sixteenth embodiment of the present disclosure.

Figure 44A:
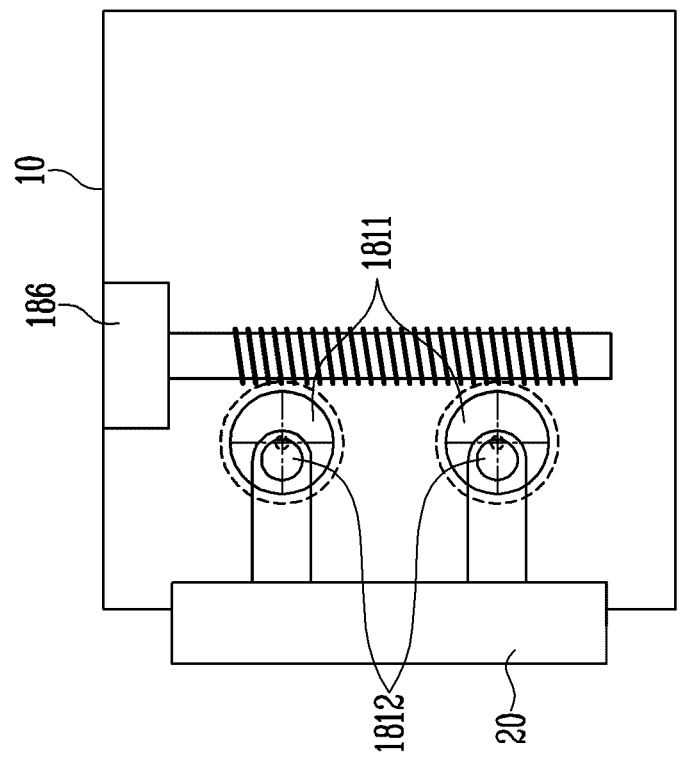
FIG. 44 is a cross-sectional view of a portable printer according to a sixteenth embodiment of the present disclosure.
Figure 44B:
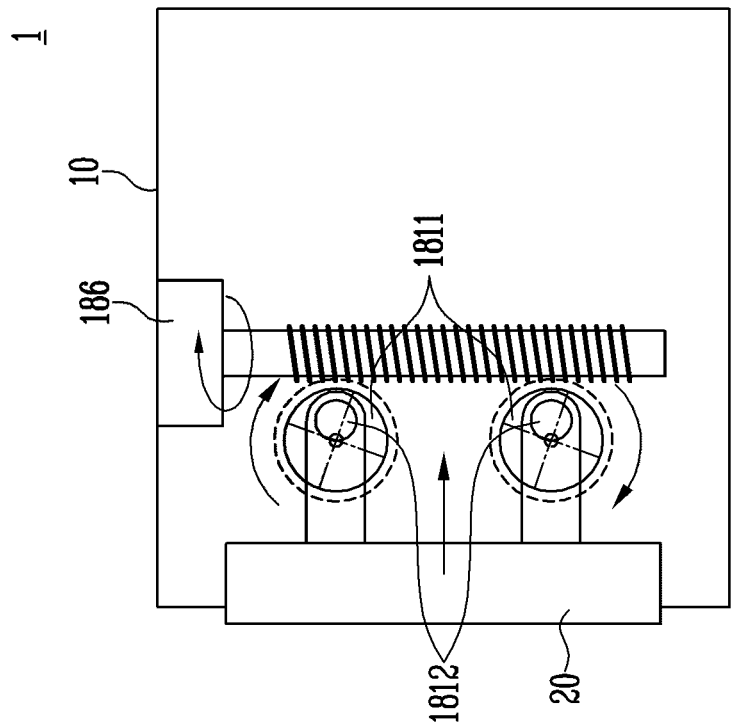

In this case, FIG. 44(A) shows a state in which the seating part 20 protrudes, and FIG. 44(B) shows a state in which the seating part is retracted.

Referring to FIG. 44, in the portable printer 1 according to the sixteenth embodiment of the present disclosure, the printing adjustment unit 100 may include the driven gear 1811 and the eccentric shaft 1812, and be provided with the operation bolt 186.

In this embodiment, moving up and down of the seating part is implemented through the driven gear 1811 and the eccentric shaft 1812 described in the previous fifteenth embodiment, and for rotation of the driven gear 1811, the operation bolt 186 may be used instead of the operation gear 181.

The operation bolt 186 may be engaged with the driven gear 1811, and in the case of a drawing in which the central axis of the operation bolt 186 is perpendicular to the central axis of the driven gear 1811, the driven gear 1811 may be provided in the form of a worm gear. Alternatively, when the central axis of the operation bolt 186 and the central axis of the driven gear 1811 are parallel, the driven gear 1811 may be provided in the form of a general sun gear.

In this embodiment, the operation gear 181 of the previous embodiment is replaced with the operation bolt 186, and in this embodiment, when the operation bolt 186 is rotated, the driven gear 1811 rotates, and only the moving up and down of the seating part 20 may be implemented through the eccentric shaft 1812. More specific details with respect to the eccentric shaft 1812 and the like will be replaced by the descriptions of the previous embodiments.

FIG. 45 is a cross-sectional view of the portable printer 1 according to a seventeenth embodiment of the present disclosure.

Figure 45A:
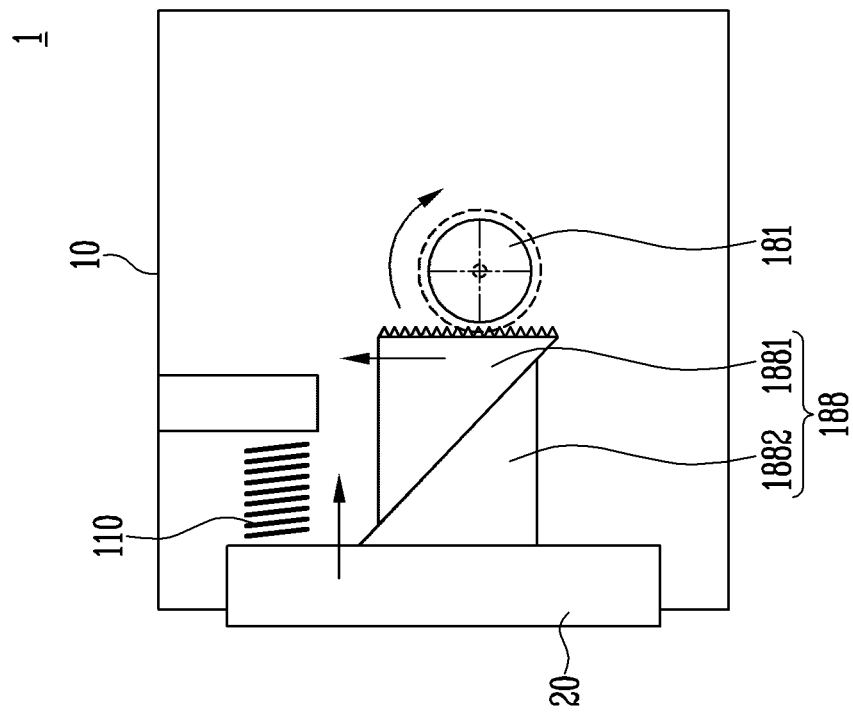
FIG. 45 is a cross-sectional view of a portable printer according to a seventeenth embodiment of the present disclosure.
Figure 45B:
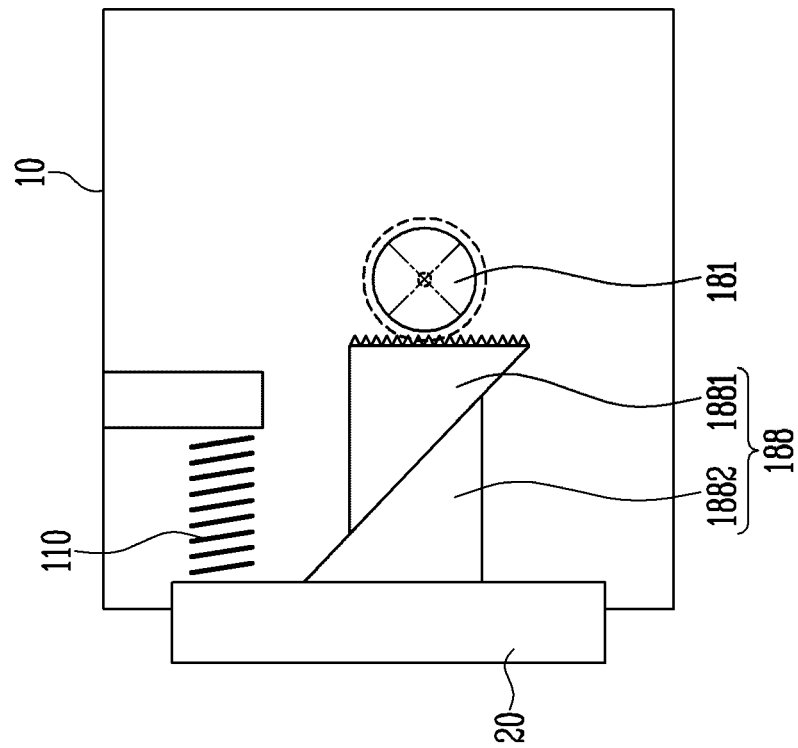

In this case, FIG. 45(A) shows a state in which the seating part 20 protrudes, and FIG. 45(B) shows a state in which the seating part is retracted.

Referring to FIG. 45, in he portable printer 1 according to the seventeenth embodiment of the present disclosure, the printing adjustment unit 100 includes the elastic member 110, the operation gear 181, and a slider 188.

The elastic member 110 is a configuration for moving the seating part 20 in the inner direction of the main body 10, and may be a tension spring.

The operation gear 181 may be rotated by external or internal manipulation. In addition, as mentioned above, the operation gear 181 may be automatically manipulated by the user manually or through sensing.

The slider 188 may include a driving slider 1881 that comes into contact with the operation gear 181 and a driven slider 1882 fixed to the seating part 20. A rack (not shown) may be formed in a portion of the driving slider 1881 in contact with the operation gear 181, and when the operation gear 181 rotates, the driving slider 1881 moves up and down with respect to the drawing.

The driving slider 1881 and the driven slider 1882 may come into contact with each other through an inclined surface. In this case, the inclined surface may be formed of a material (HDPE, etc.) that reduces friction force or may be coated with the material, and may be inclined compared to the translational motion of the driving slider 1881.

When the driving slider 1881 moves up and down with respect to the drawing, the driven slider 1882 that comes into contact with the driving slider 1881 through the inclined surface may move left and right with respect to the drawing. In this case, the movement of the driven slider 1882 to the right in the drawing may be caused by the elastic member 110, and conversely, the movement of the driven slider 1882 to the left in the drawing may be caused by the driving slider 1881.

The driven slider 1882 is provided integrally in the seating part 20, and as the driven slider 1882 moves left and right with respect to the drawing, the seating part 20 may move up and down in the inner and outer directions of the main body 10.

In other words, in the present embodiment, since the slider 188 includes the driving slider 1881 and the driven slider 1882 that come into contact with an inclined surface, the driven slider 1882 may convert a horizontal movement of the driving slider 1881 into a vertical movement and transmit the converted movement to the seating part 20.

In this case, the inclination angle of the inclined surface may be variously determined according to a range of moving up and down the seating part 20, a degree of manipulation, and the like. When the moving up and down of the seating part 20 is to be slowly adjusted, an inclination angle of the inclined surface relative to the translational movement direction of the driving slider 1881 may be 45 degrees or less, and conversely, when the moving up and down of the seating part 20 is to be rapidly switched, the inclination angle of the inclined surface relative to the translational movement direction of the driving slider 1881 may be 45 degrees or more.

FIG. 46 is a cross-sectional view of the portable printer 1 according to an eighteenth embodiment of the present disclosure.

Figure 46A:
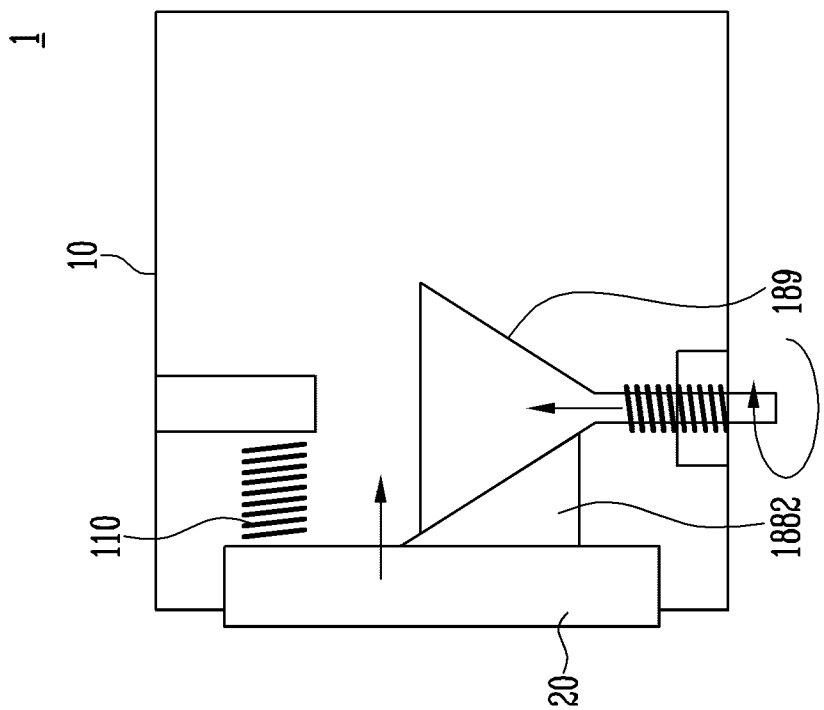
FIG. 46 is a cross-sectional view of a portable printer according to an eighteenth embodiment of the present disclosure.
Figure 46B:
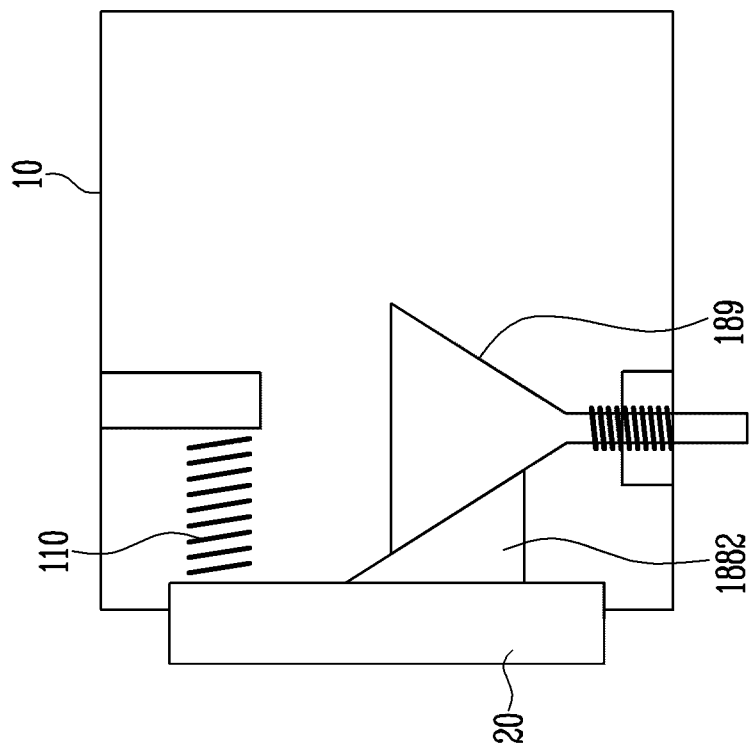

In this case, FIG. 46(A) shows a state in which the seating part 20 protrudes, and FIG. 46(B) shows a state in which the seating part is retracted.

Referring to FIG. 46, in the portable printer 1 according to the eighteenth embodiment of the present disclosure, the printing adjustment unit 100 includes the elastic member 110 and an operation roller 189. In addition, the printing adjustment unit 100 may include the driven slider 1882 of the slider 188.

Similar to the previous embodiment, the present embodiment may implement the moving up and down of the seating part through the inclined surface of the driven slider 1882. However, in the present embodiment, instead of using the driving slider 1881, the operation roller 189 may be used.

One end of the operation roller 189 may be provided to be operable by the user or automatically, and the operation roller 189 may be provided in a form capable of moving up and down with respect to the drawing. For example, in the drawing, the operation roller 189 is screwed with a nut (not shown) provided in the main body 10, so that when the operation roller 189 rotates, the operation roller 189 may move up and down with respect to the main body 10.

Alternatively, the operation roller 189 may be pressurized by an external force and moved up and down with respect to the drawing. In other words, the operation roller 189 may be manipulated by a rotating method or a push method.

The other end of the operation roller 189 comes into contact with the inclined surface of the driven slider 1882. To this end, a cone or a truncated cone having an inclined surface may be formed at the other end of the operation roller 189. When the operation roller 189 moves up and down with respect to the drawing, an action similar to the movement of the driving slider 1881 in the seventeenth embodiment may be performed.

Therefore, when the operation roller 189 moves upward with respect to the drawing while contacting the driven slider 1882 on the inclined surface, the driven slider 1882 moves in the inner direction of the main body 10 by the elastic member 110 and thus the seating part 20 is placed in the retracted position. Conversely, when the operation roller 189 moves downward with respect to the drawing while contacting the driven slider 1882 on the inclined surface, the driven slider 1882 may pushed in the outer direction of the main body 10 by the operation roller 189 to place the seating part 20 in the protruding position.

FIG. 47 is a cross-sectional view of the portable printer 1 according to a nineteenth embodiment of the present disclosure.

In this case, FIG. 47(A) shows a state in which the seating part 20 protrudes, and FIG. 47(B) shows a state in which the seating part is retracted.

Referring to FIG. 47, in the portable printer 1 according to the nineteenth embodiment of the present disclosure, the printing adjustment unit 100 may include an electromagnet 190.

The electromagnet 190 may be attached to an attachment piece 1901 provided in the seating part 20 through mutual magnetism, and the attachment piece 1901 may be formed of a material such as metal or a magnet.

The electromagnet 190 may be provided on one side with respect to the attachment piece 1901 and may change the polarity of the magnet. In other words, the electromagnet 190 may receive power conversion by an external or internal signal and have a repulsive or attractive force with respect to the attachment piece 1901.

The attachment piece 1901 is fixed and installed in the seating part 20 and moves integrally with the seating part 20. At this time, since the electromagnet 190 has the repulsive or attractive force with respect to the attachment piece 1901, the attachment piece 1901 may move in a predetermined direction with respect to the electromagnet 190.

However, in order to move the seating part 20 stably based on the repulsive force and the attractive force, the electromagnet 190 may be provided on both sides of the attachment piece 1901 based on the inner and outer directions of the main body 10.

According to FIG. 47(A), one end of the electromagnet 190 located on the inner side of the attachment piece 1901 may have the repulsive force, and the other end located on the outside of the attachment piece 1901 may have the attractive force. Thereafter, the polarity of the electromagnet 190 may be reversed by a signal input, and one end of the electromagnet 190 located on the inner side of the attachment piece 1901 may have the attractive force, and the other end located on the outside of the attachment piece 1901 may have the repulsive force.

As described above, when the electromagnet 190 is provided on both sides of the attachment piece 1901, the repulsive force and the attractive force may be utilized at the same time to rapidly and accurately induce the movement of the attachment piece 1901. However, in this embodiment, the degree of magnetism applied by the electromagnet 190 to the attachment piece 1901 may be set to a degree that allows movement of the attachment piece 1901 but does not affect the operation of peripheral components of the main body 10.

In the present embodiment, through switching of the polarity of the electromagnet 190, the seating part 20 may be selectively switched only to either the protruding position or the retracted position. This is different from the case of using the screw coupling in the previous tenth embodiment and the like. Since the tenth embodiment and the like use the screw coupling, the seating part 20 moves continuously between the protruding position and the retracted position, and may be stopped even in the intermediate position. On the other hand, in the present embodiment, the switching of the seating part 20 may be rapidly performed, but the seating part 20 may not be stopped in the intermediate position.

FIG. 48 is a cross-sectional view of the portable printer 1 according to a twentieth embodiment of the present disclosure.

Figure 48A:
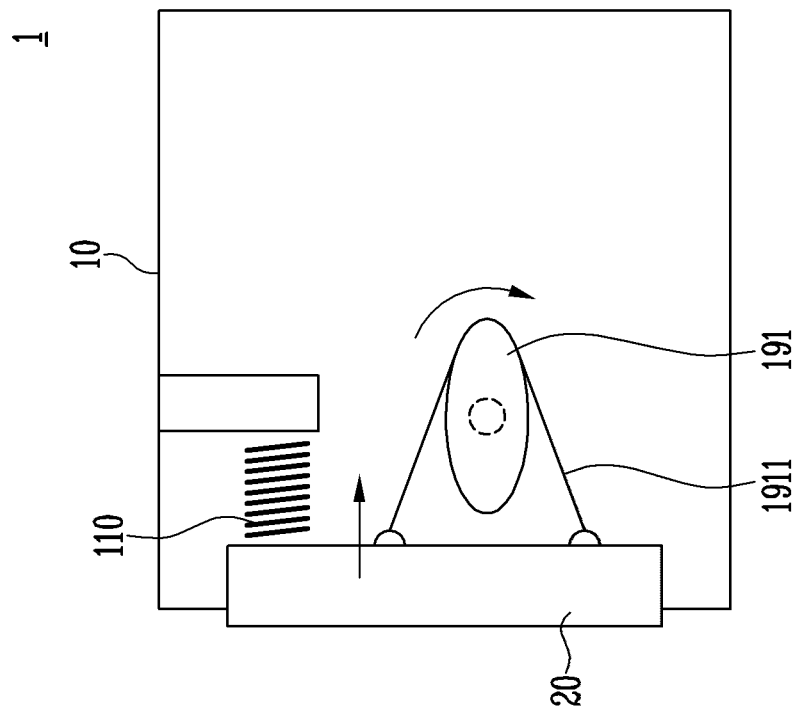
FIG. 48 is a cross-sectional view of a portable printer according to a twentieth embodiment of the present disclosure.
Figure 48B:
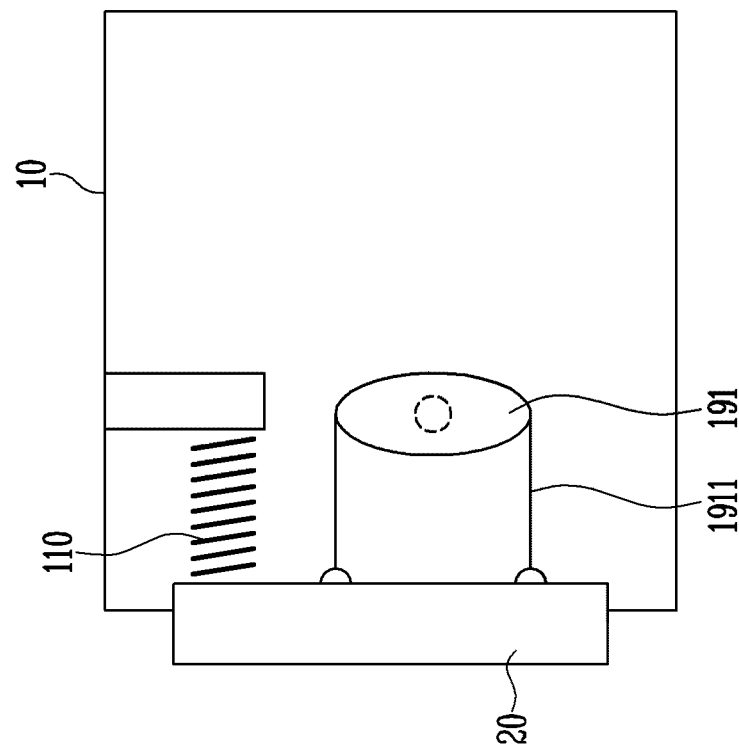

In this case, FIG. 48(A) shows a state in which the seating part 20 protrudes, and FIG. 48(B) shows a state in which the seating part is retracted.

Referring to FIG. 48, in the portable printer 1 according to the twentieth embodiment of the present disclosure, the printing adjustment unit 100 may include the elastic member 110 and an asymmetric roller 191.

The elastic member 110 is a configuration of pushing the seating part 20 in the outer direction of the main body 10, and may be a compression spring.

The asymmetrical roller 191 may be noncircular in cross section and in a radial asymmetric form. For example, the asymmetrical roller 191 has an elliptical cross-section. The asymmetric roller 191 may rotate by external or internal manipulation, and the asymmetric roller 191 may be connected to a belt 1911 fixed to the seating part 20.

The belt 1911 is a configuration including a chain, a band, a wire, or the like, and may be wound on at least a portion of the asymmetric roller 191. A central portion of the belt 1911 may be wound around the asymmetric roller 191 while both ends of the belt 1911 are fixed to the seating part 20.

The asymmetrical roller 191 is rotatably provided, and when the asymmetrical roller 191 rotates, the length of a portion of the belt 1911 in contact with the asymmetrical roller 191 as well as the position of the innermost point in the main body 10 that comes in contact with the asymmetrical roller 191 may be changed.

As the central portion of the belt 1911 is pulled or released by the asymmetrical roller 191, both ends of the belt 1911 may move in the inner and outer directions of the main body 10. In other words, based on the method in which the asymmetrical roller 191 further winds or unwinds the belt 1911 using the elliptical cross-sectional shape, the belt 1911 may allow the seating part 20 to move in the inner direction or in the outer direction of the main body 10.

As such, the present embodiment may allow the seating part to be placed in the protruding position or the retracted position by assistance of the elastic member 110 and rotation of the asymmetric roller 191. In addition, since the present embodiment may provide the elastic force of the elastic member 110 to the seating part 20 in both the protrusion position and the retracted position, the seating part 20 may be made elastically contact with the surface of the hard or soft target.

FIG. 49 is a portable printer according to a 21st embodiment of the present disclosure, and FIGS. 50 and 51 are cross-sectional views of the portable printer according to the 21st embodiment of the present disclosure.

In addition to the configuration as described in the previous embodiments, the present embodiment may further include a component for replacing the cartridge 31.

The cartridge 31 is accommodated inside the main body 10, and the cartridge 31 may be seated in the carriage 30 having a shape in which the head 32 and the nozzle 33 may be exposed to the outside. The cartridge 31 is replaceably mounted within the main body 10, and the carriage 30 may also be removable within the main body 10.

Since the cartridge 31 is detachably coupled to the carriage provided inside the main body 10, the portable printer 1 may be in a state in which printing through the nozzle 33 is possible by providing the carriage 30 in the main body 10 and fastening the cartridge 31 into the carriage 30.

The portable printer 1 includes the cartridge replacement unit 200 that allows the cartridge 31 to be easily replaced by moving at least the cartridge 31 of the carriage 30 or the cartridge 31.

The cartridge replacement unit 200 is provided in the main body 10, and the carriage 30 or the cartridge 31 may be pushed up toward the outside of the main body 10. For example, the cartridge replacement unit 200 includes a replacement button 210 and a cam 220. The replacement button 210 is exposed to the outside and movable in a horizontal direction, and may have a form similar to the operation button 121 in the previous fifth embodiment.

The cam 220 is provided between the carriage 30 and the main body 10. Previously, the cam 122 has been mentioned in the fifth embodiment, and in the case of the fifth embodiment, it is provided between the seating part 20 and the main body 10, which is different from the present embodiment.

The cam 220 of the present embodiment is provided between the carriage 30 and the main body 10 to push up the carriage 30 or the like with respect to the main body 10, and the cam 122 of the fifth embodiment is provided between the seating part 20 and the main body to push up the main body 10 with respect to the seating part 20.

The cam 220 of the present embodiment may borrow at least a part of the shape of the cam 122 described in the previous fifth embodiment, and the cam 220 may additionally include a pressing protrusion 230.

The cam 220 provided between the carriage 30 and the main body 10 may be in a state where one end is connected to the replacement button 210 and the other end faces the bottom of the carriage 30. One end of the cam 220 is rotatable by the replacement button 210, and when one end of the cam 220 rotates, a height of the other end of the cam 220 is varied. In other words, when the other end of the cam 220 moves up when the cam 220 rotates, the carriage 30 may also move up.

In this case, the carriage 30 rises relative to the main body 10, but since the cartridge 31 mounted in the carriage 30 rises with the carriage 30, it may be difficult to replace only the cartridge 31.

Cam 220 may use the pressing protrusion 230 to separate the cartridge 31 from the carriage 30. The cartridge replacement unit 200 may have the pressing protrusion 230 on another side of the cam 220, and the carriage 30 has a slit 240 that allows penetration of the pressing protrusion 230.

The slit 240 is provided to have a position and size through which the pressing protrusion 230 can be penetrated in consideration of the direction of rotation of the cam 220, and the lower portion of the cartridge 31 may be disposed adjacent to the upper portion of the slit 240.

The cam 220 may be rotated by the replacement button 210 in a first state that does not push up the carriage 30 to a second state in which the carriage 30 is pushed up from the main body 10. Thereafter, the cam 220 can be further rotated, and if the cam 220 rotates further by further operation of the replacement button 210, the pressing protrusion 230 provided in the cam 220 may push up the cartridge 31 relative to the carriage 30 through the slit 240.

In other words, the pressing protrusion 230 pushes only the cartridge 31 in the carriage 30 through the slit 240 in a third state in which the cam 220 rotates above a predetermined angle, facilitating the exchange of the cartridge 31.

Hereinafter, a method of replacing the cartridge 31 will be described through the drawings.

First, as shown in FIGS. 49(A) and 50(A), the cartridge 31 is housed in the carriage 30 and the carriage 30 is mounted in the main body 10, and the cam 220 is in a first state that is not rotated.

At this time, the cam 220 may be located in the main body 10, and only the replacement button 210 may be provided outside the main body 10 to rotate the cam 220 through operation outside the main body 10.

When the user rotates the cam 220 to a second state using the replacement button 210, as shown in FIGS. 49(B) and 50(B), the other end of the cam 220 may push up the carriage 30 within the main body 10 as the height increases.

However, in this case, since there is no great need to keep the carriage 30 pushed up, the other end of the cam 220 may have a curved or inclined form unlike the drawing.

Looking at the state of FIG. 49(B), the carriage 30 is separated from the main body 10, but the cartridge 31 remains seated in the carriage 30. At this time, the user further pushes the replacement button 210 in the horizontal direction to further rotate the cam 220 to a third state. In this case, as shown in FIGS. 49(C) and 50(C), the pressing protrusion 230 provided in the cam 220 passes through the slit 240 of the cartridge 31 and pushes up only the carriage 30.

However, for upward removal of the cartridge 31, the upper body 11 may be a structure in which the upper side is opened and closed. Alternatively, if the cartridge 31 and the carriage 30 are fastened to the lower body 12, during the process of switching the cam 220 from the first state to the third state, the upper side of the cartridge 31 may be in an open state as the upper body 11 is separated relative to the lower body 12.

The user confirms that the cartridge 31 is separated from the carriage 30 by further rotation of the cam 220, and at least the cartridge 31 of the cartridge 31 and the carriage 30 can be easily exchanged through the upper portion open in the main body 10.

On the other hand, if the user wishes to install a new cartridge 31, the user pushes the cartridge 31 into the carriage 30 and pressurizes the cartridge 31 to cause the carriage 30 to fall. In this case, the pressing protrusion 230 may be pressed by the cartridge 31 and the cam 220 may be pressed by the carriage 30 so that the cartridge replacement unit 200 may be restored to its original state.

Alternatively, the user may return the cam 220 to a first state using the replacement button 210 and then mount the cartridge 31 into the main body 10.

Figure 52A:
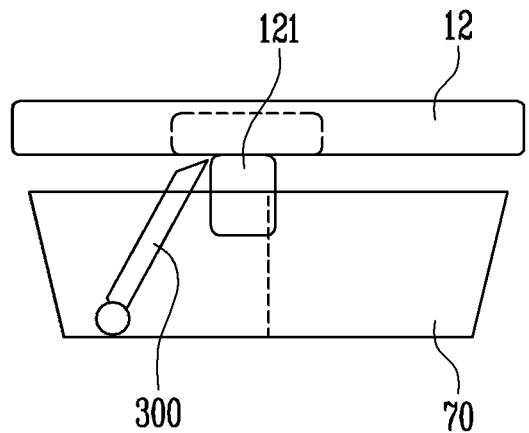
FIG. 52 is a side view of a portable printer according to a 22nd embodiment of the present disclosure.
Figure 52B:
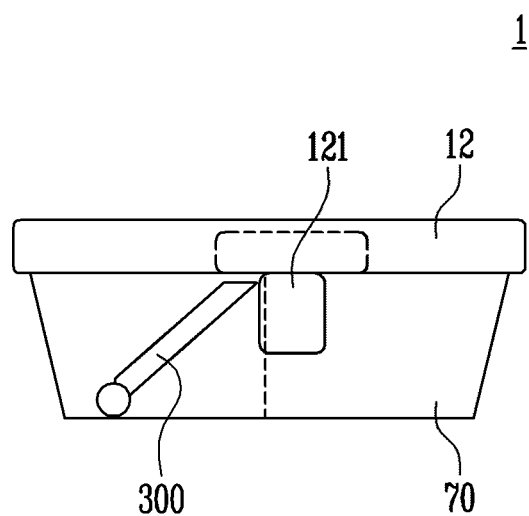
Figures 53A, 53B:
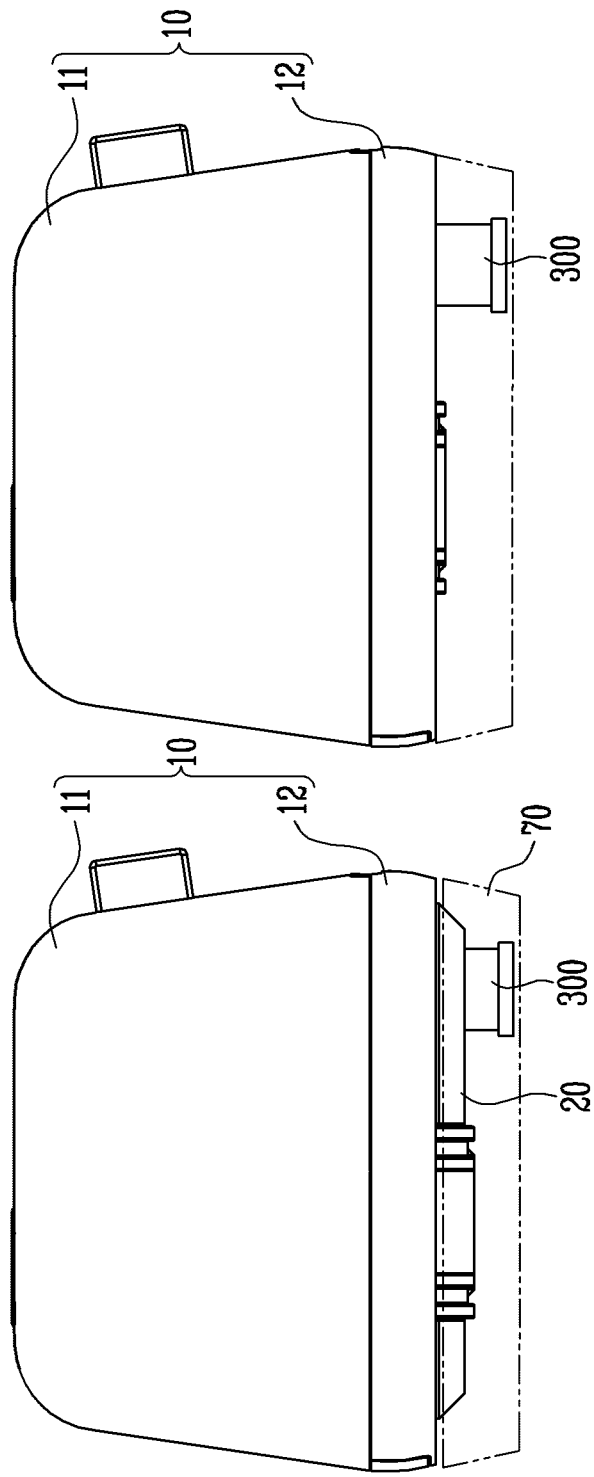
FIG. 53 is a side view of the portable printer according to the 22nd embodiment of the present disclosure.

FIGS. 52 and 53 are side views of a portable printer according to a 22nd embodiment of the present disclosure.

Referring to FIGS. 52 and 53, the portable printer 1 according to the 22nd embodiment of the present disclosure may adjust the position of the seating part 20 using the printer cover 70 compared to the previous embodiment.

However, the present embodiment and the 23rd and 24th embodiments which will be described below may be premised to include the printing adjustment unit 100 described in the fifth embodiment.

The printer cover 70 of the present embodiment may include an interference member 300 that interferes with the operating member 120. The printer cover 70 is coupled to the lower body 12 or the seating part 20 to protect the head 32 and the nozzle 33 from the outside, and in particular, when the printer cover 70 is coupled to the main body 10, etc., the height of the seating part 20 may be automatically retracted.

Referring again to the fifth embodiment, when considering the operation method of the operating member 120 and the elastic member 110, the operation button 121 overcomes the elastic force of the elastic member 110 when the seating part 20 protrudes, and conversely, may receive help from the elastic force of the elastic member 110 when the seating part 20 is retracted.

In other words, in the fifth embodiment, with the operation button 121, an operation of retracting the seating part 20 may be easily performed with relatively little force, compared to an operation of protruding the seating part 20.

In view of this, the operation button 121 is operated in the direction of changing the seating part 20 from the protruding position to the retracted position by the interference member 300 provided in the printer cover 70 when the printer cover 70 is coupled.

In other words, when the interference member 300 is deformed to push the main body 10 from the seating part 20 while the operating member 120 tensions the elastic member 110, the printer cover 70 pushes the operation button 121 in the horizontal direction in the process of sealing the nozzle 33.

Therefore, when the operation button 121 is moved by the interference member 300, the cam 220 is rotated to a state where the main body 1 is no longer pushed up, so that the seating part 20 may be restored to the retracted position by the elastic member 110.

In this case, the interference member 300 may be a pusher having its own elastic force having a spring inside, and the inclined pusher pushes the operation button 121 in the horizontal direction so that the seating part 20 is switched to the retracted position.

The printer cover 70 may be coupled to the lower body 12, and when the seating part 20 is placed in the protruding position, the seating part 20 between the printer cover 70 and the lower body 12 may interfere with the coupling of the printer cover 70. Therefore, in the present embodiment, when the printer cover 70 is coupled, the seating part 20 is automatically restored to the retracted position, so that it is possible to prevent insufficient fastening between the printer cover 70 and the lower body 12 due to the seating part 20.

FIG. 54 is a side view of a portable printer according to a 23rd embodiment of the present disclosure.

Referring to FIG. 54, in the portable printer 1 according to the 23rd embodiment of the present disclosure, the interference member 300 may be provided in a fixed form compared to the previous embodiment. In other words, the interference member 300 may be in the form of an inclined protrusion provided inside the printer cover 70, and when the printer cover 70 is coupled to the lower body 12, the inclined protrusion may come into contact with the operation button 121.

Figure 54A:
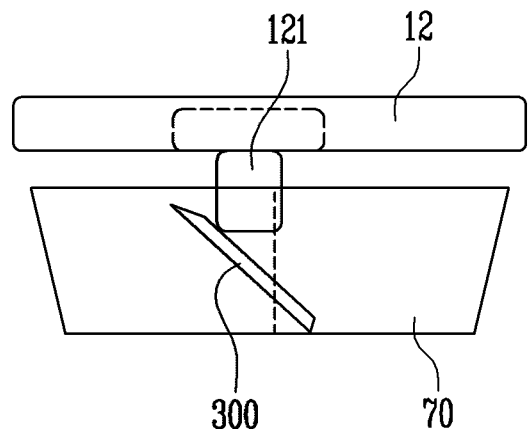
FIG. 54 is a side view of a portable printer according to a 23rd embodiment of the present disclosure.
Figure 54B:
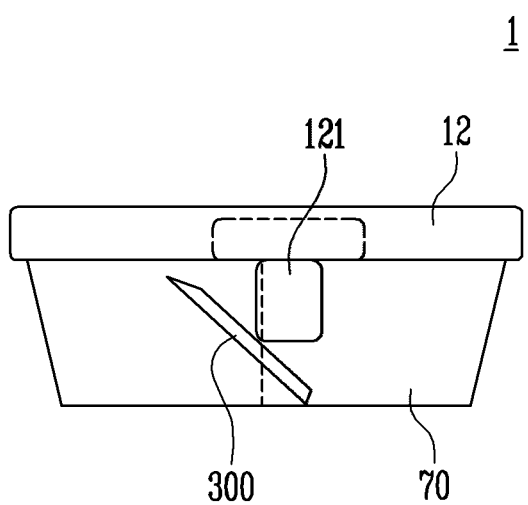

At this time, since the operation button 121 may be naturally pushed by the inclined protrusion and moved in the horizontal direction, the operation button 121 may switched from the state of FIG. 54(A) to the state of FIG. 54(B) so that the seating part 20 can be retracted.

Figure 55A:
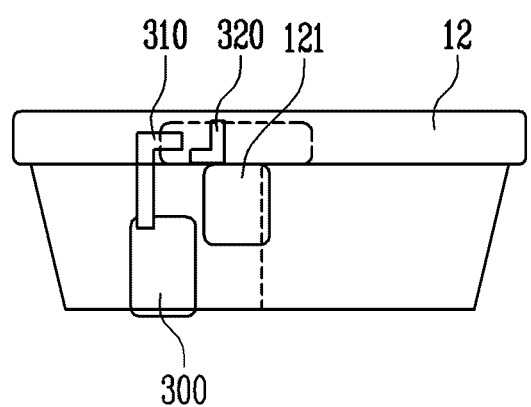
FIG. 55 is a side view of a portable printer according to a 24th embodiment of the present disclosure.
Figure 55B:
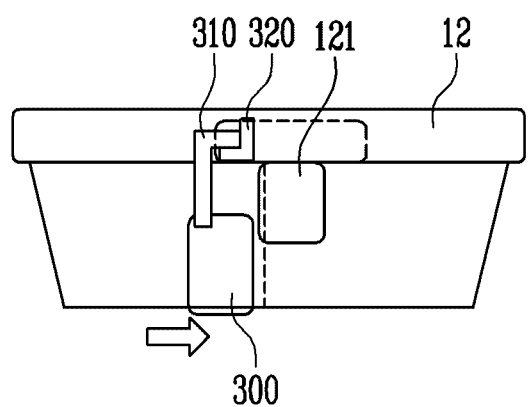

FIG. 55 is a side view of a portable printer according to a 24th embodiment of the present disclosure.

Referring to FIG. 55, in the portable printer 1 according to the 24th embodiment of the present disclosure, instead of the operation button 121 moving horizontally in the process of coupling the printer cover 70, the operation button 121 may move horizontally by manual operation after coupling the printer cover 70 to retract the seating part 20.

For example, one end of the interference member 300 is provided to be operable from the outside of the printer cover 70, and the other end is provided adjacent to the operation button 121. At this time, the other end of the interference member 300 may face the operation button 121 while the printer cover 70 is coupled to the lower body 12.

In a state in which the operation button 121 changes the seating part 20 to the protruding position while tensioning the elastic member 110, the other end of the interference member 300 may move the operation button 121 by manipulation of one end. In other words, the user engages the printer cover 70 with the lower body 12, and then pushes one end of the interference member 300 to move the operation button 121 by the other end. Therefore, the seating part 20 may be restored to the retracted position by the elastic member 110.

In this case, in order to eliminate fastening interference caused by the seating part 20 between the printer cover 70 and the lower body 12, a locking member 310 is provided in the interference member 300, and a locking ring 320 is provided in the lower body 12. Therefore, when the interference member 300 is moved by the user, the seating part is retracted while the operation button 121 moves horizontally, and at the same time, the locking member 310 of the interference member 300 and the locking ring 320 of the lower body 12 are engaged.

In this case, the locking member 310 and the locking ring 320 may have "¬" and "L" shapes, respectively, as shown in the drawing, and may also have a partially inclined shape to induce an upward movement of the locking member 310 with respect to the locking ring 320 in the engagement process.

In this case, the user may change the seating part 20 to the retracted position using the interference member 300 while the printer cover 70 is placed adjacent to the lower body 12 without being completely mounted thereto. At this time, as the interference member 300 moves and the locking member 310 moves slightly upward with respect to the locking ring 320 to be caught, the printer cover 70 may move up slightly and be completely fastened to the lower body 12.

On the other hand, in the present embodiment, unlike the previous 22nd and 23rd embodiments, since the printer cover 70 is engaged with the lower body 12, it will be possible to remove the printer cover 70 after manipulation of the interference member 300.

Figure 56:
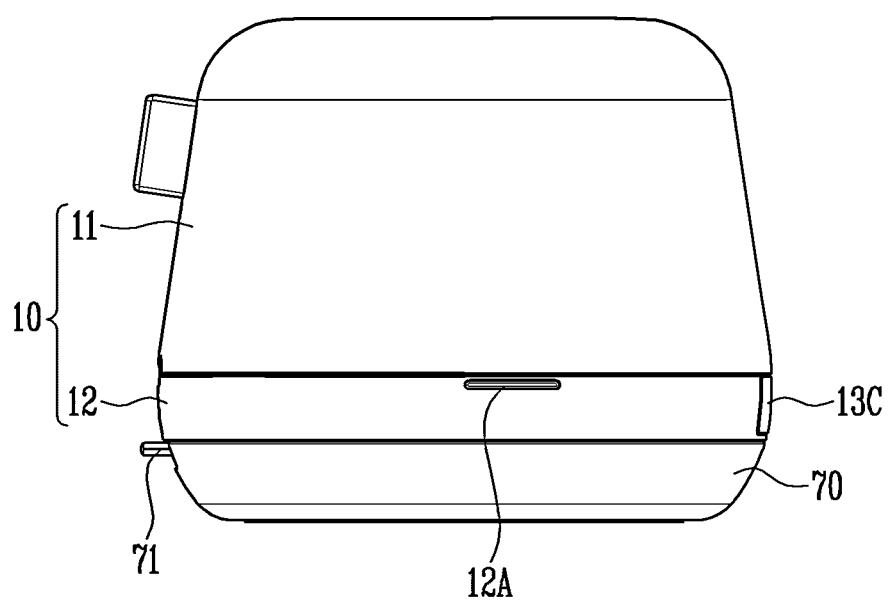
FIG. 56 is a side view of a portable printer according to a 25th embodiment of the present disclosure.
Figure 57:
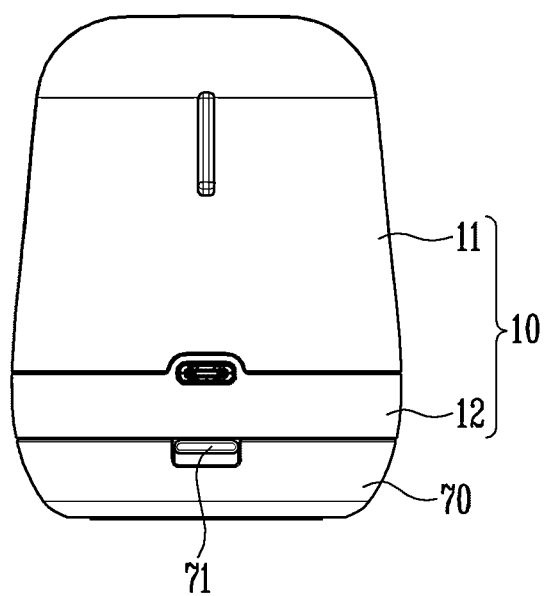
FIG. 57 is a side view of the portable printer according to the 25th embodiment of the present disclosure.
Figure 58:
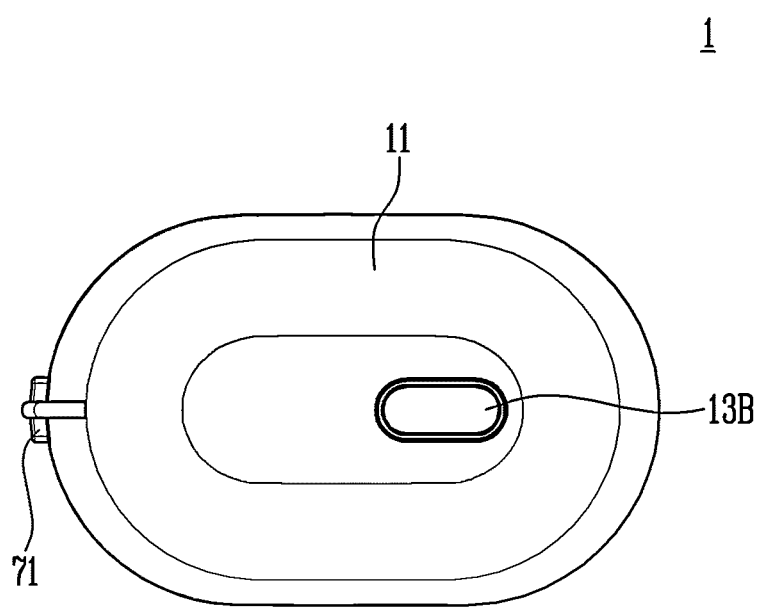
FIG. 58 is a plan view of the portable printer according to the 25th embodiment of the present disclosure.
Figure 59:
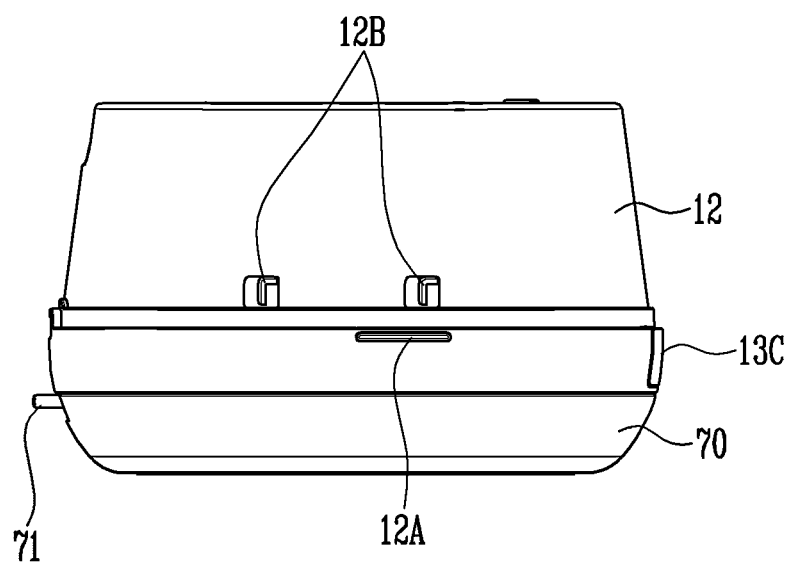
FIG. 59 is a side view of the portable printer according to the 25th embodiment of the present disclosure.
Figure 60:
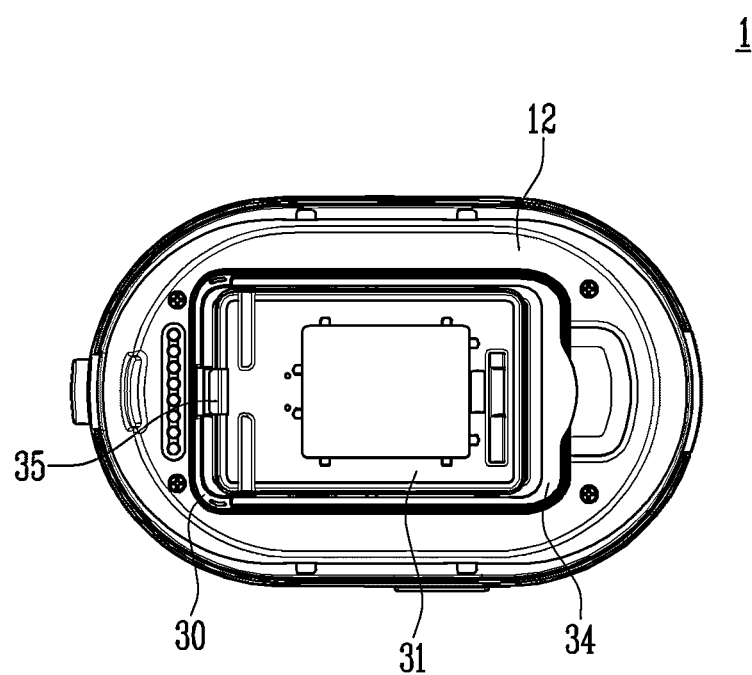
FIG. 60 is a plan view of the portable printer according to the 25th embodiment of the present disclosure.
Figure 61:
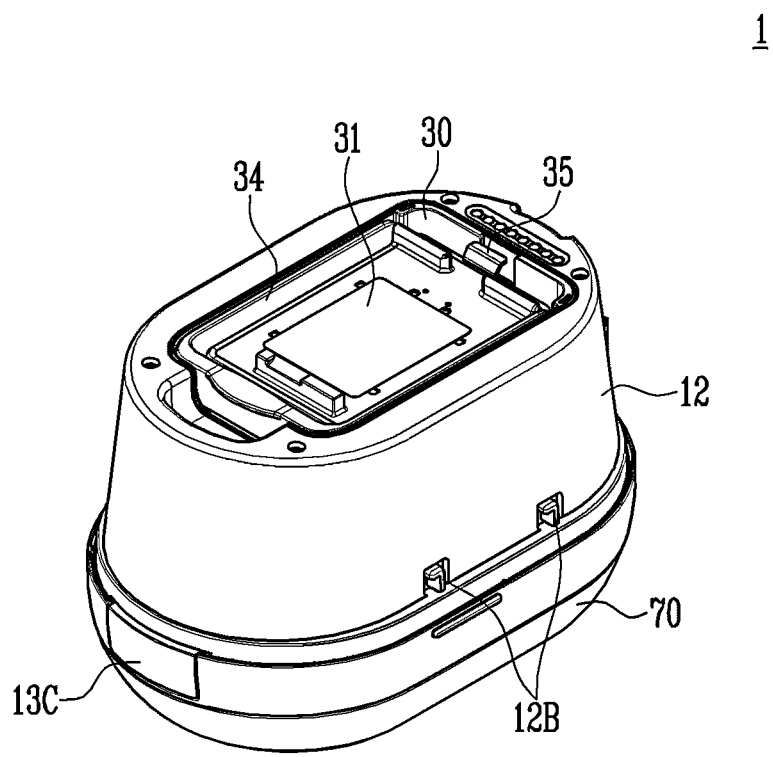
FIG. 61 is a perspective view of the portable printer according to the 25th embodiment of the present disclosure.
Figure 62:
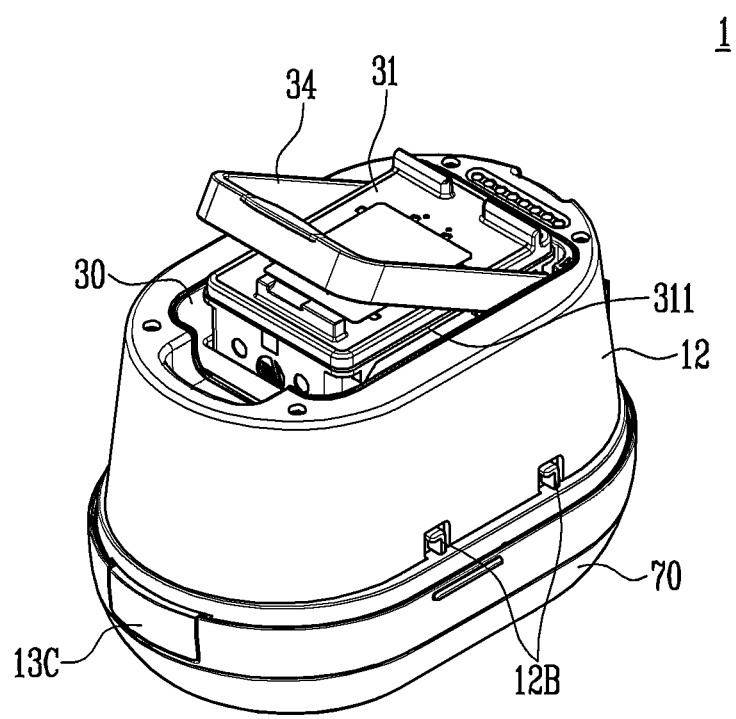
FIG. 62 is a perspective view of the portable printer according to the 25th embodiment of the present disclosure.
Figure 63:
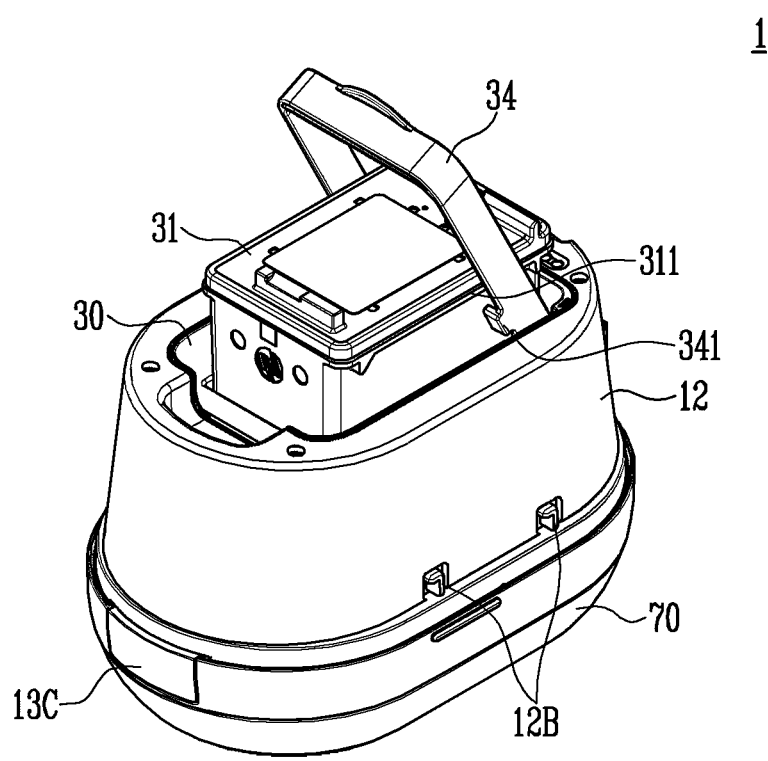
FIG. 63 is a perspective view of the portable printer according to the 25th embodiment of the present disclosure.

FIGS. 56 and 57 are side views of a portable printer according to a 25th embodiment of the present disclosure, and FIG. 58 is a top view of the portable printer according to the 25th embodiment of the present disclosure. In addition, FIG. 59 is a side view of the portable printer according to the 25th embodiment of the present disclosure, FIG. 60 is a plan view of the portable printer according to the 25th embodiment of the present disclosure, and FIGS. 61 to 63 are perspective views of the portable printer according to the 25th embodiment of the present disclosure.

For reference, FIGS. 56 to 58 show a state in which the upper body 11 is coupled to the lower body 12, and FIGS.

Figure 64:
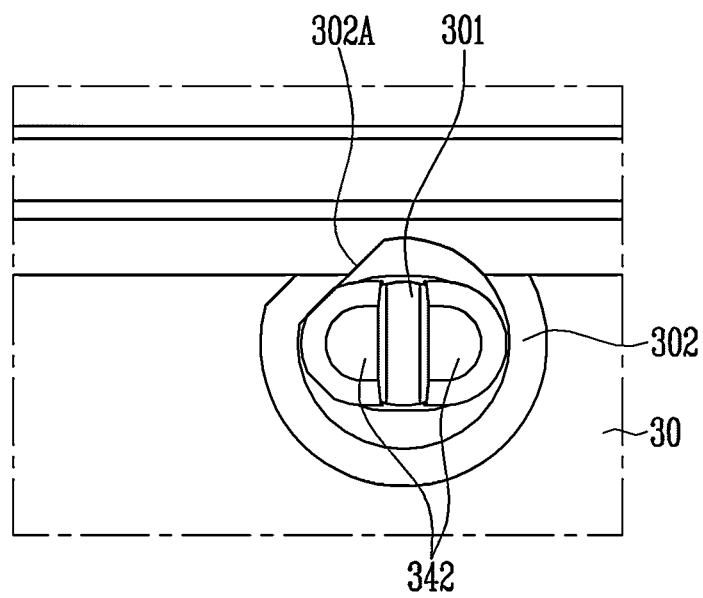
FIG. 64 is a partial side view of a carriage of the portable printer according to the 25th embodiment of the present disclosure.

59 to 63 show a state in which the upper body 11 is removed. Further, FIG. 64 is a partial side view of a carriage of the portable printer according to the 25th embodiment of the present disclosure.

Figure 65:
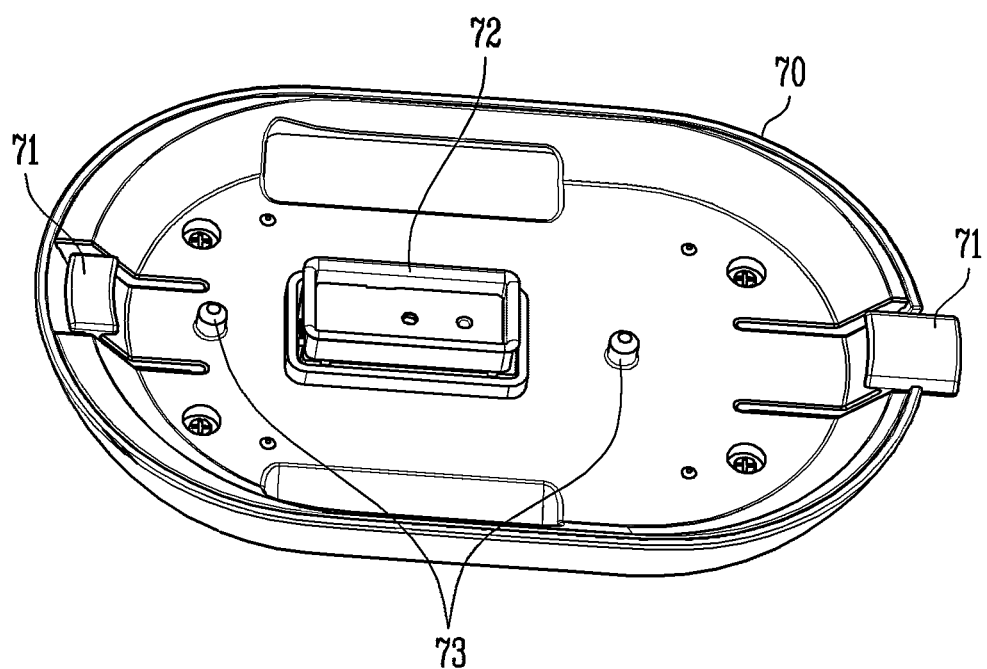
FIG. 65 is a perspective view of a printer cover of the portable printer according to the 25th embodiment of the present disclosure.
Figure 66:
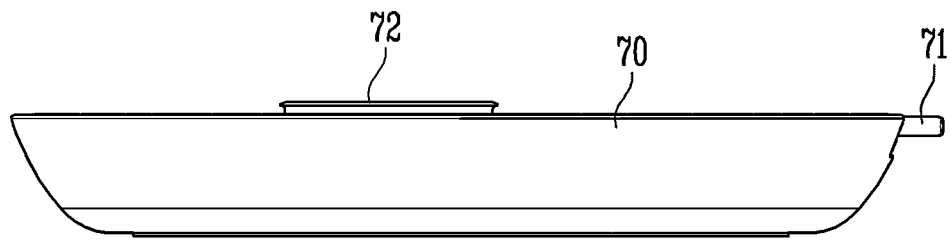
FIG. 66 is a side view of the printer cover of the portable printer according to the 25th embodiment of the present disclosure.
Figure 67:
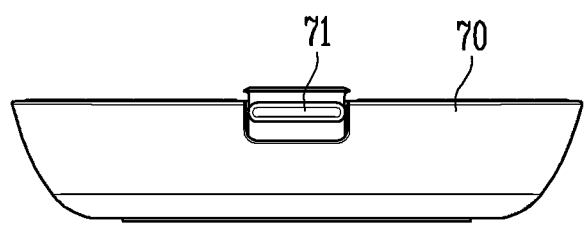
FIG. 67 is a side view of the printer cover of the portable printer according to the 25th embodiment of the present disclosure.

In addition, FIG. 65 is a perspective view of a printer cover of the portable printer according to the 25th embodiment of the present disclosure, and FIGS. 66 and 67 are side views of the printer cover of the portable printer according to the 25th embodiment of the present disclosure.

Figure 69:
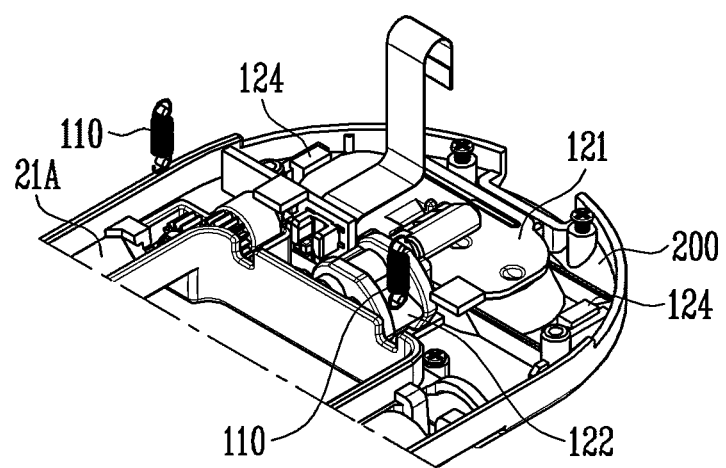
FIG. 69 is an internal perspective view of the portable printer according to the 25th embodiment of the present disclosure.
Figure 70:
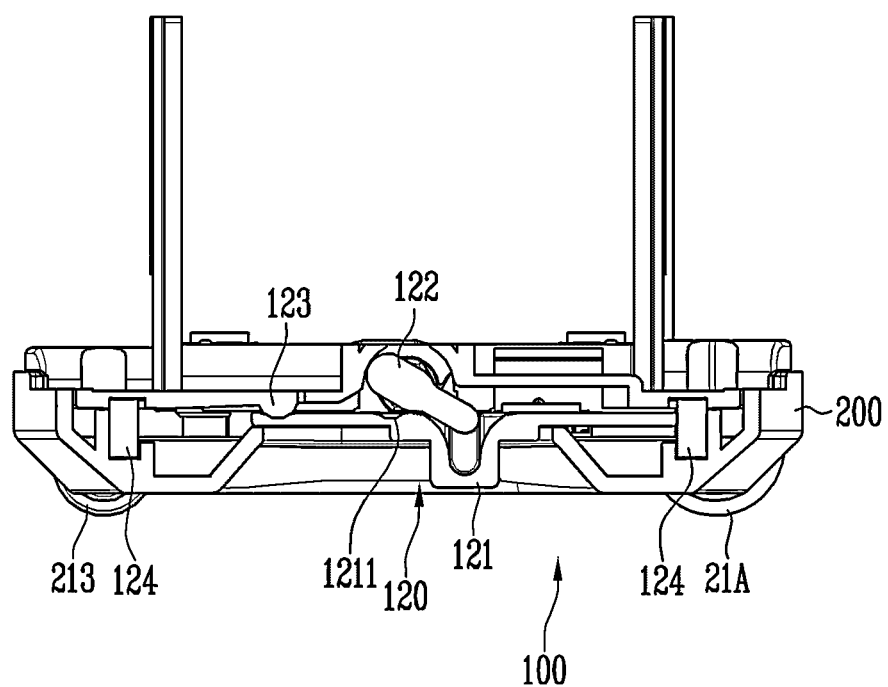
FIG. 70 is an internal side view of the portable printer according to the 25th embodiment of the present disclosure.

In addition, FIG. 68 is a partial perspective view of the portable printer according to the 25th embodiment of the present disclosure, FIG. 69 is an internal perspective view of the portable printer according to the 25th embodiment of the present disclosure, and FIG. 70 is an internal side view of the portable printer according to the 25th embodiment of the present disclosure.

Referring to FIGS. 56 to 70, the portable printer 1 according to the 25th embodiment of the present disclosure further includes an identification unit 12A in the main body 10 compared to the previous embodiments.

The identification unit 12A may be a configuration that implements some functions described through the separation button 13C in the first embodiment above. For example, the identification unit 12A guides a movement direction of the main body 10, and a printing start position of the main body 10 may be visually identified.

In particular, the identification unit 12A may be formed to correspond to a portion of the nozzle 33 from which the printing material is sprayed to guide the printing start position and a printing area. In other words, the identification unit 12A may be provided to have the same or similar width as the nozzle 33, and may have a size corresponding to the width of the area on which the printing material is printed. Therefore, the user may use the portable printer while anticipating the position and size of printing based on the position and size of the identification unit 12A.

The identification unit 12A may protrude outward from the lower body 12 or the like by a predetermined height, and the user may touch the identification unit 12A with a finger or the like when grasping the main body 10 to recognize a printing start point and a printing direction.

As mentioned in the first embodiment above, the identification unit 12A may implement guidance through light-emitting. In other words, the identification unit 12A is provided with a structure or material that transmits light generated from a light source such as an LED provided inside to the outside, and may guide a printing state using light emission at the beginning of printing or during printing.

The function of the identification unit 12A guiding the printing state by light emission may also be implemented by the power button 13B. Considering that the identification unit 12A may be covered by the finger or the like while the user is grasping the main body 10, the power button 13B or the like may be provided to assist the identification unit 12A.

In addition, in this embodiment, when referring to FIG. 59, at least one of the lower body 12 or the upper body 11 may have a snag 24. The snag 24 has a cross-section such as a "¬" shape to limit movement in the separation direction.

The snag 24 may be integrally connected to the separation button 13C, and the snag 24 may move horizontally with respect to FIG. 59 by pressing the separation button 13C. A snag (not shown) may be provided in the upper body 11 to correspond to the snag 24 provided in the lower body 12, and the snag of the upper body 11 has the form of an inverted triangle, so that when the upper body 11 is fastened to the lower body 12, a declined surface of the snag of the upper body 11 may elastically push the snag 24 of the lower body 12.

Thereafter, when the snag of the upper body 11 exceeds the snag 24 of the lower body 12, the fastening of the upper body 11 and the lower body 12 is completed. At this time, when the separation button 13C provided on the lower body 12 is pressed, the snag 24 of the lower body 12 may be vertically displaced from the snag of the upper body 11 while moving horizontally, so that the upper body 11 may be separated from the lower body 12 without being locked.

Hereinafter, with reference to FIGS. 60 to 64, a method in which the cartridge 31 is separated in the present embodiment will be described.

As described in other embodiments above, the carriage 30 for accommodating the cartridge 31 may be embedded in the main body 10. For example, the cartridge 31 may be inserted and fitted into the carriage 30 through a concave-convex structure, so that the nozzle 33 may be aligned in an appropriate position on the seating part 20.

The cartridge 31 may also be provided detachably from the carriage 30. For example, in the present embodiment, the detachment of the cartridge 31 may be implemented using a lever 34. The lever 34 may be provided rotatably within the carriage 30. The lever 34 may have an enlarged area so that one side far from a center point of rotation can be easily lifted by the user. The carriage 30 and the lower body 12 have a partially recessed form to accommodate at least a portion of the lever 34.

The lever 34 may be provided with a lifting part 341. In relation to the lifting part 341, the cartridge 31 may be provided with a step 311, and the lifting part 341 is disposed below the step 311. The lifting part 341 is provided at a position spaced apart from the center point of rotation of the lever 34, and when the lever 34 is rotated by the user, the lifting part 341 may move upward. In this case, since the lifting part 341 pushes the step 311 of the cartridge 31 upward, the cartridge 31 rises upward in the carriage 30.

However, in order to stably move up the carriage 30, the lever 34 has a ⊂-shape or a ▢-shape surrounding at least both sides of the cartridge 31, and a pair of the lifting parts 341 may be provided to correspond to the step 311 of the cartridge 31.

With reference to the drawings, a method of removing the cartridge 31 is described. First, FIGS. 60 and 61 show a state in which the lever 34 is housed and the cartridge 31 is fully fastened in the carriage 30. On the other hand, FIG. 62 shows a state in which the lever 34 is rotated upward at a predetermined angle, and the lifting part 341 not visible in FIG. 62 moves up the cartridge 31 by a predetermined height.

Thereafter, when the user further rotates the lever 34 as shown in FIG. 63, the lifting part 341 moves up the cartridge 31 sufficiently, and the cartridge 31 is placed in a state where it is easy to separate from the carriage 30.

Conversely, when mounting the cartridge 31, the user may seat a new cartridge 31 in the carriage 30 and rotate the lever 34. At this time, the lever 34 may have a structure that presses down at least a part of an upper surface circumference of the cartridge 31. Alternatively, the user may press the cartridge 31 instead of rotating the lever 34, and at this time, the lever 34 may be rotated by the moving down of the cartridge 31 while the step 311 of the cartridge 31 interferes with the lifting part 341 of the lever 34.

When the cartridge 31 is fully retracted into the carriage 30, the cartridge 31 may be caught by a locking piece 35 provided on the carriage 30. The locking piece 35 may be provided at a position opposite to or other than the center of rotation of the lever 34, and may be provided in an elastically deformable material or shape.

The locking piece 35 may be a configuration that restricts the removal of the cartridge 31, while the lever 34 may be a configuration that induces the removal of the cartridge 31. When the lever 34 rotates, the cartridge 31 may move up and push the locking piece 35 so that engagement with the locking piece 35 may be released naturally. Conversely, when the cartridge 31 is retracted into the carriage 30, the cartridge 31 may move down and push the locking piece 35 and get caught by the locking piece 35.

Moreover, in the present embodiment, convenience for rotation of the lever 34 may be increased through a rotating pin 342 of the lever 34. The rotating pin 342 of the lever 34 has a head with a cross-section of an enlarged nail-like shape, and penetrates the carriage to form the center point of rotation of the lever 34. In this case, in the carriage 30, a first portion 301 through which the rotating pin 342 passes is circular, and a second portion 302 surrounding the head of the rotating pin 342 is a combination of a noncircular portion 302A in an arc (such as a partially truncated circle).

As shown in FIG. 64, the rotating pin 342 is provided in a form in which the head is at least open. Here, the head of the rotating pin 342 may have an elastic force to be opened.

FIG. 64 shows a state in which the lever 34 is housed in the lower body 12 and the cartridge 31 is coupled to the carriage 30. At this time, the head of the rotating pin 342 is opened by the elastic force, and the elastic force of the rotating pin 342 is not interfered with the noncircular portion 302A in the second portion 302 of the carriage 30.

On the other hand, when the lever 34 is rotated to remove the cartridge 31, at least one side of the open head of the rotating pin 342 is pressed by the noncircular portion 302A of the second portion 302, so that the open head of the rotating pin 342 becomes narrower, and rotation is somewhat suppressed. Thereafter, when the lever 34 is sufficiently rotated, the rotating pin 342 passes the noncircular portion 302A of the second portion 302 and returns to the open state due to the elastic force.

As such, in the present embodiment, the rotating pin 342 of the lever 34 is interfered with by the carriage 30 during rotation of the lever 34. In other words, the lever 34 is interfered with by the carriage when lifted in the state where it is housed, and conversely, the lever 34 is interfered with by the carriage 30 when it rotates from the state where it is sufficiently lifted back toward the state where it is housed.

This allows the lever 34 to most stably maintain the housed state or a sufficiently rotated state to remove the cartridge 31, thereby preventing unnecessary rotation of the lever 34.

Hereinafter, with reference to FIGS. 65 to 68, the printer cover 70 of the present embodiment will be described. For reference, FIG. 68(A) is a view of the portable printer 1 with the printer cover 70 removed viewed from one side, and FIG. 68(B) is a view of the portable printer 1 with the printer cover 70 removed viewed from the other side.

The printer cover 70 of the present embodiment may be provided detachably with respect to the main body 10, and may be manufactured in a double structure including an inner cover (symbol not shown) and an outer cover (symbol not shown).

Here, the inner cover is provided with a hook 71. The hook 71 may be engaged with the main body 10 or the seating part 20 so that the printer cover 70 is coupled to the main body 10. The hooks 71 may be provided at both ends of the printer cover 70, but one or more hooks may be provided at locations not limited. For fastening with the hook 71, the seating part 20 may have a locking groove 12B at a position facing the hook 71.

The hook 71 is provided in the form of an elastic arm to realize elastic fastening. The hook 71 is elastically deformed to open outwards by the seating part 20 in the process of coupling the printer cover 70 to the main body 10, and is restored to the original state at the position of the locking groove 12B and caught in the locking groove 12B.

At this time, at least one side of the hook 71 is provided to protrude outwards and is provided to be changeable by the user. Therefore, when the printer cover 70 coupled to the main body 10 is to be removed, the user may detach the hook 71 from the locking groove 12B by elastically deforming the hook 71 protruding outward. In this case, since one side of the printer cover 70 in which the hook 71 deformed is located is separated from the seating part 20, separation from the other side of the printer cover 70 may be easily made thereafter.

For secure fastening of the printer cover 70, a pair of the hooks 71 and a pair of the locking grooves 12B may be provided. However, the pair of hooks 71 are asymmetrical and thus the coupling direction of the printer cover 70 to the main body 10 may be guided. Through this, a sealing part 72 provided in the printer cover 70 appropriately covers the nozzle 33. This will be described below.

The printer cover 70 includes the sealing part 72 for sealing the nozzle 33 or the like. The nozzle 33 is a place where the printing material for printing is discharged, and is preferably sealed to prevent the printing material from drying out.

Therefore, the printer cover 70 may place the sealing part 72 so that the nozzle 33 is primarily sealed when the printer cover 70 is fastened to the main body 10. To this end, the sealing part 72 may be at least partially made of an elastic material, and may receive an elastic force in the direction toward the nozzle 33 by an elastic body (not shown) such as a spring.

The nozzle 33 provided in the seating part 20 may be provided in left and right asymmetrical positions on the outer surface of the seating part 20. Then, the sealing part 72 for sealing the nozzle 33 is also provided in an asymmetrical position on the plane of the printer cover 70.

At this time, in order to make the nozzle 33 and the sealing portion 72 meet each other, the pair of hooks 71 may be asymmetrically arranged as described above. In other words, since the coupling direction of the printer cover 70 to the main body 10 is limited to one direction by the hooks 71 provided asymmetrically, when the printer cover 70 is coupled to the main body 10, the sealing part 72 may always face the nozzle 33.

The printer cover 70 is provided with a pin 73. The pin 73 may be inserted into a hole 25 provided in the seating part 20. Through this, the printer cover 70 may be suppressed from shaking while being fastened to the seating part 20 with the hook 71. Of course, the hole 25 may be provided in the printer cover 70 and the pin 73 may be provided in the seating part 20. In addition, both the pin 73 and the hole 25 are provided in the printer cover 70, and the opposite components may be disposed in the seating part 20. Using both the pin 73 and the hole 25 may limit the fastening direction of the printer cover 70 and the seating part 20.

Hereinafter, with reference to FIGS. 69 and 70, the printing adjustment unit 100 of the present embodiment will be described.

The present embodiment may include the printing adjustment unit 100 as described above in the fifth embodiment and the like. In other words, the printing adjustment unit 100 includes the elastic member 110 and the operating member 120, and the operating member 120 may include the operation button 121 and the cam 122 connected to the operation button 121.

Moreover, in the present embodiment, a groove 1211 may be provided in the operation button 121 and an elastic protrusion 123 may be provided in contact with the groove 1211. A plurality of the grooves 1211 may be provided in the operation button 121, and the grooves 1211 may cooperate with the elastic protrusion 123 to constrain the state of the operation button 121.

The elastic protrusion 123 may be fixed and installed at a predetermined position in the main body 10, and whenever the operation button 121 switches the seating part 20 to the protruding position or retracted position, the groove 1211 and the elastic protrusion 123 may be selectively engaged.

Therefore, the groove 1211 and the elastic protrusion 123 maintain the position of the operation button 121 when the seating part is in the protruding position or when the seating part 20 is in the retracted position. In other words, the groove 1211 and the elastic protrusion 123 may set a lower limit of the external force required when manipulating the operation button 121 for moving up and down the seating part 20.

However, when the operation button 121 moves while overcoming the locking of the groove 1211 and the elastic protrusion 123, the operation button 121 may collide with a part of the seating part 20 and generate noise. In order to solve this, the present embodiment may include an elastic pad 124 around the operation button 121.

When the elastic pad 124 moves the operation button 121 to switch the seating part 20 to the protruding position or the retracted position, it touches the end of the operation button 121 to reduce impact. To this end, the elastic pad 124 may be provided with an elastic material such as silicone, and the noise generated during manipulation of the operation button 121 may be reduced, and the collision between the operation button 121 and the seating part 20 may be suppressed to improve durability.

The elastic pad 124 is installed in the seating part 20 and is provided on both sides of the operation button 121 to protect the operation button 121 from impact when the operation button 121 moves to one side or the other side.

The present disclosure is not limited to the embodiments described above, and may include a combination of at least two or more of the above embodiments or a combination of at least one of the above embodiments and a known technology as a new embodiment.

While the present disclosure has been described in detail with reference to specific embodiments thereof, they are only to specifically explain the present disclosure and the present disclosure is not limited thereto. It will be apparent that variations or improvements are possible by those skilled in the art within the technical spirit of the present disclosure.

All simple variations or modifications of the present disclosure fall within the scope of the present disclosure, and the specific scope of protection of the present disclosure will be clarified by the appended claims.

The invention claimed is:

1. A portable printer comprising:
a main body in a portable form which is capable of accommodating a cartridge having a nozzle configured to deliver a printing material to a target having a soft or hard surface;
a seating part which is provided to be exposed to an outside from a lower portion of the main body to face the surface of the target and at least partially surrounds the nozzle;
a roller provided respectively at the front and rear of the nozzle at the lower portion of the main body with respect to a direction in which the main body moves along the surface of the target to deliver the printing material to the target; and
a printing adjustment unit configured to adjust a height difference between the nozzle and the roller to adjust a height difference between the nozzle and the surface of the target,
wherein the roller is provided in the seating part and moves integrally with the seating part by the printing adjustment unit, and
wherein the printing adjustment unit comprises:
an elastic member which is provided between the main body and the seating part and has an elastic force to maintain the seating part in a restoration position that is one of a retracted position and a protruding position with respect to the main body; and
an operating member which is provided in the seating part and places the seating part in a change position of the other one of the retracted position and the protruding position with respect to the main body by external manipulation.

2. The portable printer of claim 1, wherein the height difference between the nozzle and the roller is adjusted by moving at least the roller of the seating part and the roller in inner and outer directions of the main body.

3. The portable printer of claim 2, wherein the portable printer is provided for both skin and paper use by adjusting the height difference between the nozzle and the surface of the target by the printing adjustment unit.

4. The portable printer of claim 1, wherein the portable printer is provided for both skin and paper use by adjusting the height difference between the nozzle and the surface of the target by the printing adjustment unit.

5. The portable printer of claim 1, wherein the nozzle is disposed closer to an inside of the main body compared to the roller, and
wherein the printing adjustment unit is configured to move the roller to a protruding position to adjust a height between the nozzle and the roller to 6.0 mm to 7.0 mm when delivering the printing material to soft skin, and
move the roller to a retracted position to adjust the height between the nozzle and the roller to 0.5 mm to 2.5 mm when delivering the printing material to hard paper.

6. The portable printer of claim 1, wherein the roller comprises:
a first roller provided at the front of the nozzle with respect to the direction of movement of the main body; and
a second roller provided at the rear of the nozzle with respect to the direction of movement of the main body, and
the first roller and the second roller maintain the same height difference with the nozzle when moving the roller by the printing adjustment unit.

7. The portable printer of claim 1, wherein the elastic member is a tension spring to maintain the seating part in the retracted position, and
the operating member is deformed to push the main body out of the seating part while tensioning the elastic member by external manipulation so that the seating part is placed in the protruding position.

8. The portable printer of claim 7, wherein the operating member comprises:
an operation button exposed to the outside and movable in a horizontal direction; and
a cam provided between the seating part and the main body, wherein, when one end of the cam is rotated by the operation button, a height of the other end facing the main body is varied.

9. The portable printer of claim 1, wherein the elastic member is a tension spring to maintain the seating part in the retracted position, and
the operating member engages with a locking protrusion of the main body to maintain the seating part in the protruding position, or when the operating member is disengaged from the locking protrusion of the main body by external manipulation, the seating part is moved by the elastic member to be placed in the retracted position.

10. The portable printer of claim 9, wherein the operating member comprises an operation button configured to limit movement of the seating part by the elastic member with its one end exposed to the outside and the other end in contact with the locking protrusion, and allow movement of the seating part by the elastic member when the one end of the operation button is pressed and the other end is rotated so as to be deviated from the locking protrusion.

11. The portable printer of claim 10, wherein a plurality of the operation buttons are provided, and
one end of each of the plurality of operation buttons protrudes at a uniform height from one surface of the seating part facing the surface of the target.

12. The portable printer of claim 10, wherein the operation button
is provided so that its one end protrudes relatively more than the roller from the seating part, and is pressed by the target having the hard surface to be disengaged from the locking protrusion.

13. The portable printer of claim 1, further comprising:
a carriage provided inside the main body and in which the cartridge is detachably coupled; and
a cartridge replacement unit configured to move at least the cartridge of the carriage and the cartridge within the main body.

14. The portable printer of claim 13, wherein the cartridge replacement unit comprises:
a replacement button exposed to the outside and movable in a horizontal direction; and
a cam provided between the carriage and the main body, wherein when one end of the cam is rotated by the replacement button, a height of the other end facing the carriage is varied.

15. The portable printer of claim 14, wherein the cartridge replacement unit further comprises a pressing protrusion provided on another side of the cam,
the carriage has a slit that allows penetration of the pressing projection, and
the pressing protrusion penetrates the slit and pushes the cartridge with respect to the carriage when the cam rotates at a predetermined angle or more.

16. The portable printer of claim 1, wherein the printing material is a printing solution having a viscosity of 4 mPa*s to 6 mPa*s.

* * * * *